US011046949B2

(12) United States Patent
Birnboim et al.

(10) Patent No.: US 11,046,949 B2
(45) Date of Patent: Jun. 29, 2021

(54) METHOD AND SYSTEM FOR MICROBIAL LYSIS USING PERIODATES

(71) Applicant: DNA GENOTEK INC., Kanata (CA)

(72) Inventors: H. Chaim Birnboim, Ottawa (CA); Olle Maarten De Bruin, Ottawa (CA)

(73) Assignee: DNA GENOTEK INC., Kanata (CA)

( * ) Notice: Subject to any disclaimer, the term of this patent is extended or adjusted under 35 U.S.C. 154(b) by 0 days.

(21) Appl. No.: 15/302,591

(22) PCT Filed: Apr. 10, 2015

(86) PCT No.: PCT/CA2015/050292
§ 371 (c)(1),
(2) Date: Oct. 7, 2016

(87) PCT Pub. No.: WO2015/154189
PCT Pub. Date: Oct. 15, 2015

(65) Prior Publication Data
US 2017/0130219 A1 May 11, 2017

Related U.S. Application Data

(60) Provisional application No. 61/977,953, filed on Apr. 10, 2014, provisional application No. 62/014,795, filed on Jun. 20, 2014.

(51) Int. Cl.
C12N 1/06 (2006.01)
C12N 15/10 (2006.01)
C12Q 1/6806 (2018.01)

(52) U.S. Cl.
CPC .......... *C12N 15/1003* (2013.01); *C12N 1/06* (2013.01); *C12Q 1/6806* (2013.01)

(58) Field of Classification Search
CPC .................................................. C12N 15/1003
See application file for complete search history.

(56) References Cited

U.S. PATENT DOCUMENTS

| 4,999,288 | A | * | 3/1991 | deCastro | C12Q 1/28 435/18 |
| 5,849,890 | A | * | 12/1998 | Gold | B82Y 5/00 536/23.1 |
| 5,935,804 | A | * | 8/1999 | Laine | C07K 14/001 435/18 |
| 6,190,875 | B1 | | 2/2001 | Ben-Artzi | A61L 27/34 435/18 |
| 6,313,286 | B1 | * | 11/2001 | Brown | C07H 19/06 536/27.1 |
| 7,041,484 | B1 | * | 5/2006 | Baga | C12N 9/107 435/193 |
| 2002/0037512 | A1 | * | 3/2002 | Baker | C12N 15/1003 435/6.12 |
| 2003/0008379 | A1 | * | 1/2003 | Bhosle | C12P 21/02 435/253.3 |
| 2004/0209332 | A1 | * | 10/2004 | Marciacq | C07H 19/00 435/91.2 |
| 2005/0070109 | A1 | | 3/2005 | Feller et al. | |
| 2005/0091706 | A1 | * | 4/2005 | Klimyuk | C12N 15/8222 800/278 |
| 2005/0227292 | A1 | * | 10/2005 | Sunderasan | C07K 14/415 435/7.1 |
| 2006/0154307 | A1 | * | 7/2006 | Milligan | C07K 14/70571 435/7.2 |
| 2006/0206946 | A1 | * | 9/2006 | Hamza | A01K 67/033 800/3 |
| 2007/0006390 | A1 | * | 1/2007 | Clamen | C08F 8/14 8/115.51 |
| 2008/0026375 | A1 | * | 1/2008 | Chen | B01J 39/26 435/6.16 |
| 2010/0081279 | A1 | * | 4/2010 | Palmer | C09G 1/02 438/667 |
| 2011/0239717 | A1 | * | 10/2011 | Fuentes | C05D 9/02 71/27 |
| 2012/0070830 | A1 | * | 3/2012 | Eshoo | C07D 521/00 435/6.11 |

FOREIGN PATENT DOCUMENTS

| EP | 0 265 519 B1 | 5/1988 |
| EP | 2075824 A1 | 7/2009 |
| WO | 87/06706 A1 | 11/1987 |
| WO | 9412881 A2 | 6/1994 |
| WO | 00/78150 A1 | 12/2000 |
| WO | 01/40277 A2 | 6/2001 |

(Continued)

OTHER PUBLICATIONS

Ruzin (1999) Plant Microthechnique and Microscopy (Year: 1999).*
International Search Report and Written Opinion of corresponding application No. PCT/CA2015/050292 dated Jul. 8, 2015. 9 pgs.
Partial Supplementary European Search Report dated Aug. 22, 2017, in connection with corresponding European Application No. 15777094.2 (10 pgs.).
N.N. Greenwood and A. Earnshaw, "The Halogens: Fluorine, Chlorine, Bromine, Iodine and Astatine", Chemistry of the Elements, 2nd Edition, Butterworth Heinemann, Oxford, Chapter 17, 1988, pp. 789-887 (99 pgs.).
Neel R. Gandhi, et al., "Extensively drug-resistant tuberculosis as a cause of death in patients co-infected with tuberculosis and HIV in a rural area of South Africa", Lancet, Nov. 4, 2006, vol. 368, pp. 1575-1580 (6 pgs.).
"Report of Expert Consultations on Rapid Molecular Testing to Detect Drug-Resistant Tuberculosis in the United States," Centers for Disease Control and Prevention, pp. 1-26 (26 pgs.).

(Continued)

Primary Examiner — Marcos L Sznaidman
(74) Attorney, Agent, or Firm — Maier & Maier, PLLC

(57) ABSTRACT

The present application provides a composition comprising periodates or persulfates for extracting nucleic acid from a microorganism, and a corresponding method of using the composition for nucleic acid extraction. The composition and method are particularly useful in extracting nucleic acid from microorganisms that are generally resistant to standard nucleic extraction techniques, such as, one or more species of the *Mycobacterium* genus, one or more species of the *M. tuberculosis* complex, MDR strains of *M. tuberculosis*, one or more species of *Clostridium*, one or more species of *Bacillus*, and other microorganisms with hardy cell walls.

28 Claims, 10 Drawing Sheets

(56) References Cited

FOREIGN PATENT DOCUMENTS

| WO | 03/104251 A2 | 12/2003 |
| --- | --- | --- |
| WO | 2006/133701 A2 | 12/2006 |
| WO | 2007050327 A2 | 5/2007 |
| WO | 2013/188740 A1 | 12/2013 |
| WO | 2015-179976 A1 | 12/2015 |

OTHER PUBLICATIONS

Josephine A. Morello, et al., "New Medium for Blood Cultures", Applied Microbiology, Jan. 1969, vol. 17, pp. 68-70 (3 pgs.).

Bruce M. Chassy, "A Gentle Method for the Lysis of Oral Streptococci", Biochemical and Biophysical Research Communications, vol. 68, No. 2, 1976, pp. 603-608 (6 pgs.).

Michael Kaser, et al., "Optimized Method for Preparation of DNA from Pathogenic and Environmental Mycobacteria", Applied and Environmental Microbiology, vol. 75, No. 2, Jan. 2009, p. 414-418 (5 pgs.).

Chinese Office Action dated Sep. 4, 2018, in connection with corresponding CN Application No. 201580023613.X (15 pgs., including English translation).

Martin Silberberg, "The Molecular Nature of Matter and Change", Chemistry, Mosby-Year Book Inc., USA, Chapter 2, Section 2.8, "Mixture: Classification and Separation", 1996, pp. 73-75 (5 pgs.).

European Office Action dated Nov. 5, 2018, in connection with corresponding EP Application No. 15 777 094.2 (5 pgs.).

K. Randerath, et al., "Sequence analysis of nonradioactive RNA fragments by periodate-phosphatase digestion and chemical tritium labeling: characterization of large oligonucleotides and oligonucleotides containing modified nucleosides", Nucleic Acids Research, vol. 1, No. 9, Sep. 1974, pp. 1121-1142 (22 pgs.).

Extended European Search Report dated Nov. 14, 2017, including the Supplementary European Search Report and the European Search Opinion, in connection with corresponding EP Application No. 15 777 094.2 (19 pgs.).

Ulrich Lehmann, et al., "Real-Time PCR Analysis of DNA and RNA Extracted from Formalin-Fixed and Paraffin-Embedded Biopsies", Methods, Academic Press, US, vol. 25, No. 4, 2001, pp. 409-418 (10 pgs.) (XP003017515, ISSN: 1046-2023, DOI: 10.1006/METH.2001.1263).

Marjan De Mey, et al., "Comparison of DNA and RNA quantification methods suitable for parameter estimation in metabolic modeling of microorganisms", Analytical Biochemistry, Elsevier, Amsterdam, NL, vol. 353, No. 2, Jun. 15, 2006 (Jun. 15, 2006), pp. 198-203 (6 pgs.) (XP024942171, ISSN: 0003-2697, DOI: 10.1016/J.AB.2006.02.014).

Vinay G. Joshi, et al., "Rapid label-free visual assay for the detection and quantification of viral RNA using peptide nucleic acid (PNA) and gold nanoparticles (AuNPs)", Analytica Chimica Acta, vol. 795, 2013, pp. 1-7 (7 pgs.) (XP028698983, ISSN: 0003-2670, DOI: 10.1016/J.ACA.2013.06.037).

Xiaofei Li, et al., "Comparison of three common DNA concentration measurement methods", Analytical Biochemistry, vol. 451, 2014, pp. 18-24 (7 pgs.) (XP028831562, ISSN: 0003-2697, DOI: 10.1016/J.AB.2014.01.016).

Sean Gallagher, "Quantitation of Nucleic Acids with Absorption Spectroscopy", Sep. 1, 1998 (Sep. 1, 1998), XP055419161, Retrieved from the Internet: URL:http://onlinelibrary.wiley.com/store/10.1002/0471140864.psa04ks13/asset/psa04k.pdf? V=1&t=j973wht9&s=3da536c696b35b2d0d87b89e6d20ae1133cc 4279 [retrieved on Oct. 25, 2017].

Philippe Desjardins, et al., "NanoDrop Microvolume Quantitation of Nucleic Acids", Journal of Visualized Experiments, Vo.. 45, Nov. 2010 (Nov. 22, 2010), pp. 1-4 (4 pgs.) (XP055419163, DOI: 10.3791 /2565).

Phenix Research Products, "Quantification of Nucleic Acids using Absorbance", Dec. 1, 2003 (Dec. 1, 2003), 4 pgs. (XP055419166, Retrieved from the Internet: URL:https://www.phenixresearch.com/Images/TN_Quantification.pdf [retrieved on Oct. 25, 2017]).

"Report of an Expert Consultation on the Uses of Nucleic Acid Amplification Tests for the Diagnosis of Tuberculosis", Centers for Disease Control (CDC), Department of Health and Human Services, pp. 1-7 (7 pgs.).

I. C. Shamputa, et al. "Molecular genetic methods for diagnosis and antibiotic resistance detection of mycobacteria from clinical specimens", in APMIS, 2004, vol. 112, pp. 728-752 (25 pgs).

Lucy E. Desjardin, et al., "Measurement of Sputum *Mycobacterium tuberculosis* Messenger RNA as a Surrogate for Response to Chemotherapy", in Am J Respir Crit Care Med, 1999, vol. 160, pp. 203-210 (8 pgs.).

Abbas Afkhami, et al., "Spectrophotometric Determination of Periodate, Iodate and Bromate Mixtures Based on Their Reaction with Iodide", in Analytical Sciences, Oct. 2001, vol. 17, pp. 1199-1202 (4 pgs.).

Danielle Wroblewski, et al., "Rapid Molecular Characterization of Clostridium difficile and Assessment of Populations of C. difficile in Stool Specimens", in Journal of Clinical Microbiology, Jul. 2009, vol. 47, No. 7, pp. 2142-2148 (7 pgs.).

Tanya A. Halse, et al., "Evaluation of a Single-Tube Multiplex Real-Time PCR for Differentiation of Members of the *Mycobacterium tuberculosis* Complex in Clinical Specimens", in Journal of Clinical Microbiology, Jul. 2011, vol. 49, No. 7, pp. 2562-2567 (6 pgs.).

Tanya A. Halse, et al., "Combined Real-Time PCR and rpoB Gene Pyrosequencing for Rapid Identification of *Mycobacterium tuberculosis* and Determination of Rifampin Resistance Directly in Clinical Specimens", in Journal of Clinical Microbiology, Apr. 2010, vol. 48, No. 4, pp. 1182-1188 (7 pgs.).

Elizabeth L. Corbett, PhD, et al., "The Growing Burden of Tuberculosis, Global Trends and Interactions With the HIV Epidemic", in Arch Intern Med, May 12, 2003, vol. 163, pp. 1009-1021 (13 pgs.).

American Thoracic Society, "Diagnostic Standards and Classification of Tuberculosis in Adults and Children", in Am J Respir Crit Care Med, 2000, vol. 161, pp. 1376-1395 (20 pgs.).

Gladys L. Hobby, et al., "Enumeration of Tubercle Bacilli in Sputum of Patents with Pulmonary Tuberculosis", in Antimicrobial Agents and Chemotherapy, Aug. 1973, vol. 4, No. 2, pp. 94-104 (11 pgs.).

Henry Yeager, Jr., et al., "Quantitative Studies of Mycobacterial Populations in Sputum and Saliva", in Am Rev Respir Dis, 1967, vol. 95, pp. 998-1004 (7 pgs.).

Gandhi NR, Moll A, Pawinski R, et al., "Abstract THLB0210: High prevalence and mortality from extensively drug-resistant (XDR) TB in TB/HIV-coinfected patients in rural South Africa", published in IAPAC Monthly, Metabolic complications of HIV therapy, Sep. 2006, vol. 12, No. 9, See "Abstract THLB0210" on p. 322, left-hand column (3 pp.).

Mario Raviglione, "XDR-TB: entering the post-antibiotic era?", in Int J Tuberc Lung Dis, 2006, vol. 10, No. 11, pp. 1185-1187 (3 pgs.).

J. Lucian Davis, et al., "Polymerase Chain Reaction of secA1 on Sputum or Oral Wash Samples for the Diagnosis of Pulmonary Tuberculosis", in Clinical Infectious Diseases (CID), Mar. 15, 2009, vol. 48, pp. 725-732 (8 pgs.).

Gassan Yassen, et al., "Detection of acid fast bacilli in the saliva of patients having pulmonary tuberculosis", in J Bagh College Dentistry, 2012, vol. 24, No. 3. pp. 59-62 (4 pgs.).

Anonymous, "Updated Guidelines for the Use of Nucleic Acid Amplification Tests in the Diagnosis of Tuberculosis", MMWR Morb Mortal Wkly Rep, 2009, vol. 58, 7 pgs.

R. Douglas Scott II, "The Direct Medical Costs of Healthcare-Associated Infections in U.S. Hospitals and the Benefits of Prevention", Division of Healthcare Quality Promotion, National Center for Preparedness, Detection, and Control of Infectious Diseases, Coordinating Center for Infectious Diseases, Centers for Disease Control and Prevention, Mar. 2009 (16 pgs.).

W. N. Fawley, et al., "Molecular epidemiology of endemic Clostridium difficile infection", in Epidemiol. Infect., 2001, vol. 126, pp. 343-350 (8 pgs.).

José A. Martinez, Md, et al., "Role of Environmental Contamination as a Risk Factor for Acquisition of Vancomycin-Resistant Enterococci in Patients Treated in a Medical Intensive Care Unit", in Arch Intern Med, Sep. 8, 2003, vol. 163, pp. 1905-1912 (8 pgs.).

K. Burton, et al., "Studies of Nucleotide Sequences in Deoxyribonucleic Acid", published by Cold Spring Harbor Laboratory Press,

(56) References Cited

OTHER PUBLICATIONS

Cold Spring Harbor Symposium on Quantitative Biology, 1963, vol. 28, pp. 27-34 (9 pgs.). Downloaded from symposium.cshlp.org on Oct. 13, 2016.

Gerhard Schmidt, et al., "A Method for the Determination of Desoxyribonucleic Acid, Ribonucleic Acid, and Phosphoproteins in Animal Tissues", in Journal of Biological Chemistry, received for publication on Aug. 8, 1945, vol. 161, pp. 83-89 (7 pgs.). Downloaded from: http://www.jbc.org/ by guest on Oct. 12, 2016.

G. M. Richards, "Modifications of the Diphenylamine Reaction Giving Increased Sensitivity and Simplicity", in Analytical Biochemistry, 1974, vol. 57, pp. 369-376 (8 pgs.).

John M. Kissane, et al., "The Fluorometric Measurement of Deoxyribonucleic Acid in Animal Tissues with Special Reference to the Central Nervous System", in J. Biol. Chem., Jul. 1958, vol. 233, pp. 184-188 (6 pgs.). Downloaded from : http://www.jbc.org/ by guest on Oct. 12, 2016.

European Office Action dated Jul. 4, 2019, in connection with corresponding EP Application No. 15 777 094.2 (4 pgs.).

European Office Action dated Nov. 26, 2019, in connection with corresponding EP Application No. 15 777 094.2 (4 pgs.).

\* cited by examiner

METHOD AND SYSTEM FOR MICROBIAL LYSIS USING PERIODATES

FIELD OF THE INVENTION

The present application pertains to the field of nucleic acid extraction. More particularly, the present application relates to methods and systems for maximizing or improving nucleic acid extraction from microorganisms, such as bacteria, virus, and fungi.

BACKGROUND

Composition/method to improve the release of nucleic acids from tough microorganisms and viruses.

Microorganisms, including bacteria, algae and fungi, are very diverse and live in all parts of the biosphere. Some microorganisms are critical to nutrient recycling and have intimate, mutually beneficial relationships with larger organisms, while others are pathogenic, infecting and sometimes killing the host, namely humans, other animals and plants. Microorganisms, viruses and prions cause diseases such as plague, anthrax, tuberculosis, leprosy, malaria, cholera, typhoid fever, sleeping sickness, tetanus, toxoplamosis, histoplasmosis, botulism, diphtheria, acquired immunodeficiency syndrome (AIDS), influenza, polio, measles, mumps, rubella, hepatitis A and B, herpes 1 and 2, yellow fever, dengue fever, rabies, papillomas/cancers (caused by human papilloma virus), adenovirus-mediated respiratory tract infection, and transmissible spongiform encephalopathies (e.g., Creutzfeldt-Jakob Disease).

Healthcare-associated infections (HAIs) or nosocomial infections are infections that patients acquire during the course of receiving healthcare treatment for other conditions or one that develops among hospital staff. The healthcare environment can become highly contaminated with nosocomial pathogens that are able to survive for long periods of time. These preventable infections can be devastating and a significant cause of morbidity and mortality worldwide.

Modern healthcare employs numerous types of invasive devices and procedures to treat patients. Two-thirds of HAIs are associated with the devices used in medical procedures, for example, central-line associated bloodstream infections, catheter-associated urinary tract infections, and ventilator-associated pneumonia. HAIs also may occur at surgery sites and open wounds. In addition, surfaces contaminated with *Clostridium difficile* bacterium and spores can cause gastrointestinal infection and severe illness. Other examples of microorganisms causing HAIs include *Acinetobacter, Burkholderia cepacia, Candida albicans, Clostridium Sordellii*, Enterobacteriasceae, *Escherichia coli*, Hepatitis A-C, Human Immunodeficiency Virus (HIV), Influenza, *Klebsiella, Legionella pneumophila*, Methicillin-resistant *Staphylococcus aureus* (MRSA), *Mycobacterium abscessus*, Norovirus, *Pseudomonas aeruginosa, Staphylococcus aureus, Mycobacterium tuberculosis*, Vancomycin-intermediate and -resistant *Staphylococcus aureus*, and *Stenotrophomonas maltophilia*. Infections caused by these microorganisms take up scarce health sector resources by prolonging a patient's stay in hospital.

HAIs are a critical public health problem in developed countries. In the United States, the Centers for Disease Control and Prevention (CDC) estimated roughly 1.7 million HAIs, from all types of microorganisms, including bacteria, combined, cause or contribute to 99,000 deaths each year. Every day in the U.S., about 1 in every 20 hospitalized patients has an infection caused by receiving medical care, according to the CDC. In the U.S. alone, the overall annual direct medical costs of HAI to hospitals (including inpatient hospital services) is approximately $45 billion (based on 2007 data analyzed by the CDC; RD Scott II, 2009).

Hospitals have sanitization protocols regarding uniforms, equipment sterilization, washing, and other preventive measures. Thorough hand washing and or use of alcohol rubs by all medical personnel before and after each patient contact is one of the most effective ways to combat some HAIs. Microorganisms on equipment and surfaces can be killed or sterilized through exposure to chemicals, ionizing radiation, dry heat, or steam under pressure. However, hardy microorganisms, such as *Staphylococcus*, MRSA and vancomycin-resistant *Enterococcus*, are known to survive on 'touch' surfaces (e.g., bed rails, telephones, call buttons, floors, bedside curtains, toilets, chairs, door handles, light switches, intravenous poles, counters, stethoscopes, TV remotes, and table tops), as well as in the air and in dust, for extended periods of time.

Sanitizing these surfaces is an often overlooked, yet critical, component of breaking the cycle of infection in healthcare environments. Modern sanitizing methods such as Non-flammable Alcohol Vapour in Carbon Dioxide (NAV-$CO_2$) systems have been somewhat effective against gastroenteritis, MRSA, and influenza agents. Also, hydrogen peroxide vapour reduces infection rates, especially effective against endospore-forming bacteria, such as *Clostridium difficile*, where alcohol has proven to be ineffective. Hence, to both avoid and combat HAIs, safe and effective antimicrobial agents are desperately needed in hospitals, healthcare facilities, nursing homes, and long-term care facilities to routinely disinfect common touch surfaces, reusable medical devices, and medical/dental equipment.

Researchers and infection control experts are calling for more rigorous cleaning protocols and procedures, as well as materials tailored to the different infectious pathogens. Fawley and colleagues (2001) found that some general purpose, detergent-based (ionic and non-ionic surfactants) disinfectants, without adequate disinfection, can actually increase contamination of the environment. Also, a U.S. study (Martinez et al., 2003) concluded that routine 20-30 minute cleaning (using phenolic disinfectant) was not enough to eradicate Vancomycin-resistant Enterococci (VRE) in patients' rooms. It took a more thorough four hour cleaning protocol to eliminate VRE from the medical intensive care unit (ICU). Today, there is demand for a safe, fast, effective, inexpensive, and environmentally sound way of sanitizing equipment, tools and contact surfaces, without the use of toxic or corrosive chemicals. An ideal disinfectant should have a wide antimicrobial spectrum, produce a rapid kill, nontoxic, odourless, should leave an antimicrobial film on treated surfaces, economical, soluble in water, stability, and should not damage the environment.

Most medical and surgical devices used in healthcare facilities are made of materials that are heat stable and therefore undergo heat, primarily steam, sterilization. However, since 1950, there has been an increase in medical devices and instruments made of materials that require low-temperature sterilization. Within the past 15 years, a number of new, low-temperature sterilization systems (e.g., ethylene oxide (ETO), hydrogen peroxide gas plasma, peracetic acid immersion, ozone) have been developed and are being used to sterilize medical devices (e.g., surgical instruments, implants, blood culture tubes, hypodermic syringes, biopsy forceps) and dental instruments, as well as to decontaminate microbiological waste. Technologies under development for use in healthcare facilities, but not cleared by the FDA, include vaporized hydrogen peroxide, vapour phase peracetic acid, gaseous chlorine dioxide, ionizing radiation, or pulsed light. To protect patients from infections, while minimizing risks to staff and preserving the value of the items being reprocessed, there is a need for additional new, low-temperature, environmentally-friendly sterilization technologies with excellent microbicidal activity for active microorganisms and spores.

Tuberculosis (TB) is a leading infectious disease in humans caused by members of the "*Mycobacterium tuberculosis* complex," which include, e.g., pathogenic strains of the species *M. tuberculosis, M. bovis, M. africanum, M. microti, M. cannetti, M. caprae* and *M. pinnipedi*. *Mycobacterium tuberculosis* (MT) infects about one third of the world's population, 90% of whom can remain asymptomatic for years following infection. TB is fatal in >50% of the infected population and the emergence of multi-drug resistant (MDR) strains has made diagnosis and treatment of TB a high priority in developing African populations. MT grows slowly, which means that isolation, identification, and drug susceptibility testing of this organism and other clinically important mycobacteria are difficult and can take several weeks or months. If a Biosafety level-3 laboratory is not available in such remote locations, the difficulty in testing is confounded by the need to render the sample non-infectious prior to processing and molecular testing to reduce transmission and disease incidence. However, early and accurate diagnosis of MT infection is critical to isolating the patient, thereby reducing spread of the disease to close contacts, and to ensuring initiation of appropriate and effective treatment. Early administration of antibiotic therapy significantly reduces the severity of the disease, increases remission rates and aims to avoid the development of MDR TB. Current methods suffer from drawbacks associated with difficulty in safely collecting, transporting, stabilizing and/or extracting "good"/representative samples (such as sputum samples) from patients suspected of being infected with MT.

Current methods for diagnosis of MT infection using sputum involve collecting the sputum into an empty container, sending the potentially infectious sputum sample to a lab where the container is opened and the sample is treated with sodium hydroxide (NaOH) and N-acetyl-L-cysteine (NALC). NaOH/NALC is widely used to liquefy sputum and to reduce the background of other microorganisms, while maintaining viability of MT. MT is so hardy that the majority survives this harsh treatment, allowing selective culture of this microorganism. However, MT is very slow growing in vitro which prolongs the time to detection and diagnosis. Following the NaOH/NALC treatment, the MT-containing sediment can be concentrated prior to further processing, including a) the Ziehl-Neelsen stain to identify "acid-fast" bacteria in smears, b) conventional microbial culture methods, and c) molecular-based assays for species identification and antibiotic-resistance profiling.

In principle, the use of molecular diagnostic methods avoids the need to culture MT and, consequently, the need to maintain the bacteria in the original sample in a viable state. Furthermore, there is a worldwide need to implement more sensitive and rapid molecular diagnostic tests (using DNA and/or RNA) for tuberculosis than conventional laboratory tests for MT to enable isolation of the patient and earlier initiation of effective therapy. Commercially-available, FDA-approved assays for molecular detection of MT (e.g. Amplicor *Mycobacterium tuberculosis* Test from Roche Diagnostic Systems, Basel, Switzerland and "Enhanced Amplified *Mycobacterium tuberculosis* Direct (E-MTD) Test" from Gen-Probe, San Diego, Calif., U.S.A.) have the advantage of being standardized and reproducible, and exhibit high sensitivity (>95%) and specificity in smear-positive samples. However, one-half of all new cases of pulmonary TB are smear-negative upon initial diagnosis. Unfortunately, the FDA-approved molecular assays also demonstrate low sensitivity (40.0-92.9%, MTD test; 40.0-73.1%, Amplicor test) in smear-negative and non-respiratory samples. Furthermore, the high equipment and test costs limit their implementation in the remote, low-resource settings of developing countries ("Report of an Expert Consultation on the Uses of Nucleic Acid Amplification Tests for the Diagnosis of Tuberculosis," Centers for Disease Control and Prevention; "Molecular genetic methods for diagnosis and antibiotic resistance detection of mycobacteria from clinical specimens," APMIS (2004) 112: 728-752). One means to increase sensitivity of MT detection, and thus accuracy of molecular diagnostic tests, is to increase the efficiency of nucleic acid extraction from a given sample, in particular, DNA and RNA from the pathogenic bacteria in clinical samples. Samples from patients with active and/or dormant infection, especially individuals co-infected with HIV/TB, may contain only a small number of *Mycobacterium* embedded in thick, often 'solid', mucus. A highly effective extraction method could revolutionize the diagnosis and treatment of TB by increasing the sensitivity of detection of MT, thereby permitting earlier intervention.

The waxy cell wall of Mycobacteria contains mycolic acid, making it difficult to disrupt and greatly reducing the nucleic acid extraction efficiency of most chemical or enzymatic extraction processes. The robust bacterial cell wall hinders both cell lysis and efficient extraction of DNA (Kaser et al., 2009). The clinical market currently lacks an efficient method to extract/isolate nucleic acids from a large number of samples in a form suitable for PCR and other sophisticated molecular analyses, such as microarrays. Physical methods for microbe/cell breakage include mechanical cell disintegration (bead-beating, crushing and grinding, wet milling, ultrasonics, hydraulic shear, freeze pressure), liquid or hydrodynamic shear (French press, Chaikoff press, homogenizers, wet mills, vibration mills, filters, ultrasonic disintegration) and solid shear (grinding, Hughes press). For example, in the E-MTD Test, sonication is used to release mycobacterial rRNA from target cells. Mechanical disruption of bacteria and other microbes (e.g. fungi) produces highly variable release of DNA, very much dependent upon the specific technique used.

Compared to mechanical means such as bead-beating, some type of chemical/enzymatic lysis of hardy bacteria/spores in clinical samples would be much easier and safer to integrate into existing high-throughput, automated sample processing systems and workflows. Chemical methods of microbe/cell disintegration are aimed at modifying the cell wall, so cells either become leaky or burst due to the effects of turgor pressure. Methods include osmosis, drying and extraction, autolysis, inhibition of cell wall synthesis, enzyme attack on cell walls, bacteriophages and other lytic factors, and ionizing radiation.

Drug-resistance of MT is typically determined using the agar and liquid culture methods, which require six to eight weeks and four to five weeks, respectively, to provide results. Reliable detection of RNA from MT-positive specimens is expected to revolutionize the diagnosis and treatment of TB, in particular, multidrug-resistant and extensively drug-resistant tuberculosis (MDR/XDR TB). Rapid detection of drug-resistance using molecular methods takes one to two days which can enable earlier initiation of effective therapy and thereby reduce periods of infectiousness of MDR TB cases by as much as six weeks and improve patient outcomes globally; both of which may have a large impact on efforts to control MDR TB (Ref: "Report of Expert Consultations on Rapid Molecular Testing to Detect Drug-Resistant Tuberculosis in the United States," Centers for Disease Control and Prevention).

Quantitative measurement of MT DNA levels in TB-positive patient specimens is not a reliable marker for successful treatment in the majority of patients, since MT DNA can persist in sputum of TB patients for as long as a year after completion of treatment. In contrast, prokaryotic mRNA has a short half-life and would therefore be predicted to be found only in viable organisms. Ribosomal RNA (rRNA) is a relatively stable RNA target, compared to mRNA, with a substantially longer half-life than mRNA and greater abundance than mRNA, with estimated levels of 100 times that for the total pool of mRNA. Hence, RNA stabilization, extraction and analyses will be especially valuable for diagnosing and treating previously missed smear-negative, TB-positive samples and rapidly measuring the therapeutic margin or effectiveness of new drug regimens or current anti-TB therapies. The rapid disappearance of MT mRNA from sputum of TB-positive patients suggests that it is a good indicator of microbial viability and useful marker for rapid assessment of response to therapy (LE Desjardin et al. "Measurement of sputum *Mycobacterium tuberculosis* messenger RNA as a surrogate for response to chemotherapy" (1999) Am J Respir Crit Care Med 160: 203-210).

Currently available 'non-mechanical' methods for DNA extraction include 'Rapid extraction' (mix sample with lysis buffer including Tris, EDTA and Triton X-100, boil 15 min, precipitation of DNA with isopropanol), 'Organic extraction' (mix sample with phenol-chloroform-isoamyl alcohol, DNA precipitated from aqueous layer), 'Silica-based extraction' (mix sample with lysis buffer including guanidine thiocyanate, EDTA and Triton X-100, incubate with silica, washes, elute DNA from silica) and magnetic particles, e.g. 'MagaZorb™' (mix sample with Proteinase K and lysis buffer, incubate, add binding buffer and magnetic particles, washes, elute DNA from particles). Presently, RNA can be released from MT only by physical or mechanical disruption (e.g. bead-beating) and it is often degraded.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide a method and system for release of DNA and RNA from microbes using periodates. In accordance with an aspect of the present invention, there is provided a composition comprising an oxidizing agent and buffer, wherein the oxidizing agent is periodic acid, periodate or persulfate.

In accordance with another aspect of the invention, there is provided a method for extracting nucleic acid from a microorganism comprising mixing a sample suspected of containing the microorganism with an oxidizing agent and heating the resulting mixture, wherein the oxidizing agent is periodic acid, periodate or persulfate.

In accordance with another aspect of the invention, there is provided a kit for nucleic acid extraction, wherein the kit comprises (i) an extraction composition comprising periodate or persulfate at a concentration of from about 5 mM to about 300 mM and a buffer at a pH of from about 7 to about 13; and (ii) instructions for use.

In accordance with another aspect of the invention, there is provided a method for quantification of total nucleic acid in a sample, comprising (i) treating the sample with an acid and heating the acidified sample; (ii) neutralizing the acidified sample; and (iii) subjecting the neutralized sample to HPLC using a reverse phase column and monitoring the eluent by UV spectroscopy to identify peak corresponding to adenine; (iv) calculating the area under the curves of the adenine peaks as a measure of total nucleic acid in the sample.

BRIEF DESCRIPTION OF THE FIGURES

For a better understanding of the present invention, as well as other aspects and further features thereof, reference is made to the following description which is to be used in conjunction with the accompanying drawings, where:

FIG. 7 graphically depicts the detection of *C. botulinum*-specific DNA from spores extracted with periodate, compared to commercially-available isolation kit (Roche).

FIG. 8 graphically depicts the detection of *C. difficile*-specific DNA from spores extracted with periodate, compared to commercially-available isolation kit (Roche).

FIG. 15 graphically depicts *B. anthracis* spore viability following standard decontamination and treatment with periodate.

FIG. 16 graphically depicts *C. botulinum* spore vi

DETAILED DESCRIPTION

Figure 1:
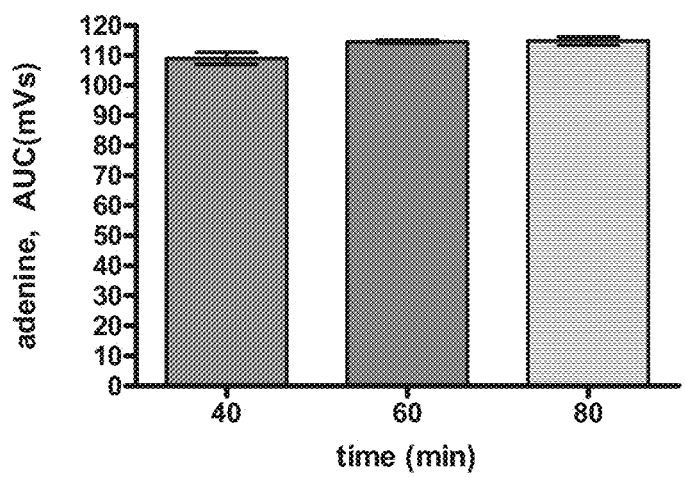
FIG. 1 graphically depicts results from an acid-treatment to release adenine from pure DNA.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The term "sample" as used herein will be understood to mean any specimen that potentially contains a substance of interest, which is optionally a nucleic acid, protein or other biomolecule of interest. The term "sample" can encompass a solution, such as an aqueous solution, cell, tissue, biopsy, powder, or population of one or more of the same. The sample can be a biological sample, such as saliva, sputum, buccal swab sample, serum, plasma, blood, buffy coat, pharyngeal, nasal/nasal pharyngeal or sinus swabs or secretions, throat swabs or scrapings, urine, mucous, feces, rectal swabs, lesion swabs, chyme, vomit, gastric juices, pancreatic juices, gastrointestinal juices, semen/sperm, urethral swabs and secretions, cerebral spinal fluid, products of lactation or menstruation, egg yolk, amniotic fluid, aqueous humour, vitreous humour, cervical secretions or swabs, vaginal fluid/secretions/swabs or scrapings, bone marrow samples and aspirates, pleural fluid and effusions, sweat, pus, tears, lymph, bronchial or lung lavage or aspirates, peritoneal effusions, cell cultures and cell suspensions, connective tissue, epithelium, epithelial swabs and smears, mucosal membrane, muscle tissue, placental tissue, biopsies, exudates, organ tissue, nerve tissue, hair, skin, nails, plants, plant extracts, algae, soil samples, sewage, wastewater, foodstuff, meat-processing equipment swabs or the like. The sample can also be a stabilized or preserved sample, in which an original nucleic acid-containing sample has been mixed or otherwise treated with a storage solution such as found in kits such as, but not limited to, Oragene®•DNA Collection Kits, Oragene®•RNA Collection Kits, OMNIgene®•Discover Infectious Disease Collection Kits, Performagene™•LIVESTOCK DNA Collection Kits, and Oragene®•Animal DNA Collection Kits, or a composition, such as described in U.S. Pat. Nos. 7,482,116, 8,158,357 and U.S. Patent Publication No. 2010/0099149, each of which are incorporated herein by reference. Preferably, the nucleic acid within such stabilized samples are maintained substantially intact and non-degraded for extended periods of time, e.g., from the point of sample collection, transport to the testing laboratory, and treatment with the present invention.

The term "microorganism" as used herein, will be understood to mean any microscopic organisms and spores, including all of the prokaryotes, namely the eubacteria and archaeabacteria, and various forms of eukaryote, comprising the protozoa, fungi (e.g., yeast), algae, and animals such as rotifers and planarians.

The term "chelator" as used herein will be understood to mean a chemical that will form a soluble, stable complex with certain metal ions, sequestering the ions so that they cannot normally react with other components. A chelator can be, for example, ethylene glycol tetraacetic acid (EGTA), (2-Hydroxyethyl)ethylenediaminetriacetic acid (HEDTA), diethylene triamine pentaacetic acid (DTPA), NitriloTri-Acetic Acid (NTA), ethylenediaminetetraacetic acid (EDTA), cyclohexanediaminetetraacetic acid (CDTA), N,N-bis(carboxymethyl)glycine, citrate anhydrous, sodium citrate, calcium citrate, ammonium citrate, ammonium bicitrate, citric acid, diammonium citrate, ferric ammonium citrate, lithium citrate, or any combination thereof.

The term "denaturing agent" as used herein will be understood to mean any chemical that can cause proteins to lose their native secondary and/or tertiary structures. A denaturing agent can be, for example, an anionic detergent, (such as, for example, sodium dodecyl sulfate (SDS), lithium dodecyl sulphate, or sodium lauroyl sulfate (SLS)), a cationic detergent (such as, for example, cetyltrimethylammonium bromide (CTAB), which may be suitable in some nucleic acid applications; cetylpyridinium bromide or alkylbenzyldimethylammonium chloride), or a nonionic detergent (such as, for example, Tween, Triton X, or Brij).

The present application provides a method, composition and system for extracting nucleic acid from microorganisms. The present method, composition and system are capable of releasing nucleic acids from microorganisms and spores that are generally resistant to standard nucleic extraction techniques, such as, one or more species of the *Mycobacterium* genus, one or more species of the *M. tuberculosis* complex, MDR strains of *M. tuberculosis*, one or more species of *Clostridium*, one or more species of *Bacillus*, and other microorganisms with hardy cell walls.

The present extraction method, composition and system have applications beyond the tuberculosis market. The method, composition and system are useful in human and animal medical diagnostics and research (e.g. population genomics to study microorganism evolution, virulence, drug-resistance, and epidemiology). In addition, many markets/industries are looking for efficient ways to break open tough bugs and spores, including food safety (food/meat processing plants), soil and water sampling (environment testing), biosecurity or biodefence (anthrax spores and other biological weapons), animal feed testing, agriculture/plant science/industry, alcohol production, etc.

A new and rapidly expanding research focus is the intestinal microbiota or gut microbiome and the analysis of microbes in stool of healthy and diseased humans. For research and economic reasons, there is also immense interest in the analysis of the thousands of different microorganisms in the rumen of many livestock, especially those animals which are reared for dairy products and meat.

The present inventors have surprisingly found that a common laboratory chemical, periodate, used at slightly alkaline pH and elevated temperature, can be used to rapidly and efficiently release nucleic acid from microorganisms, in both vegetative and dormant (e.g., endospores and spores) states. The surprising release of nucleic acid appears to be specific to periodates and, to a lesser degree, persulfates. Related compounds, such as iodate, do not significantly enhance the release of nucleic acids from bacteria or fungi.

The present chemical composition and method has the potential to simplify and expedite specimen preparation or processing for the detection of microorganisms, without the need for a cold chain or costly and time-consuming sample decontamination and emulsification. The invention can be used in central labs with high throughput systems or in rural or mobile clinics with minimal laboratory infrastructure and equipment. This utility facilitates epidemiologic and out-break surveillance, pandemic and epidemic tracking from field samples at the site of collection, as well as for rapid assessment and monitoring of a patient's response to therapy.

The hardy cell wall of *Mycobacterium* consists of a thick, waxy, hydrophobic, mycolate layer and a peptidoglycan layer held together by polysaccharide. To determine if the waxy component of the cell wall could be stripped away, various solvents (e.g., Varsol, DMSO and Hemo-De®) were tried, but no increased release of DNA was observed. Similarly, various detergents (e.g., SDS), formic acid, and borate were tested at elevated temperatures. None of these compounds, even at 100° C., was found to release more than 10% of DNA from Mycobacteria.

In addition to releasing a very high fraction of DNA/RNA from microorganisms, the present non-mechanical extraction composition and method may have the further advantage of rendering the samples non-infective, which would be beneficial for the safety of laboratory staff. Surprisingly, under conditions in which essentially the entire DNA is released, the present composition and method may still permit acid-fast staining and microscopic observation of Mycobacteria. In contrast, the inventors observed that yeast quickly disintegrate upon treatment with the present composition and method to the point where they are not capable of further analysis by staining or microscopy.

The method and system of the present application is useful in releasing DNA/RNA from bacteria and spores. The bacteria can be, for example, *Mycobacterium tuberculosis*, species of the *Mycobacterium tuberculosis* complex, *Mycobacterium smegmatis*, *Mycobacterium bovis*, *Mycobacterium africanum*, *Mycobacterium microti*, *Mycobacterium canetti*, *Mycobacterium caprae*, *Mycobacterium pinnipedi*, *Mycobacterium marinum*, *Mycobacterium leprae*, *Mycobacterium* Lepromatosis, *Mycobacterium avium*, *Mycobacterium avium*-intra-cellulare, *Mycobacterium avium paratuberculosis*, *Mycobacterium ulcerans*, *Mycobacterium gordonae*, *Bacillus species*, *Bacillus subtilis*, *Helicobacter pylori*, *Chlamydia pneumoniae*, *Chlamydia trachomatis*, *Toxoplasma gondii*, *Streptococcus species*, *Staphylococcus species*, *Dientamoeba fragilis*, *Borrelia burgdorferi* and other species, *Clostridia* species, *Fusobacterium nucleatum*, *Salmonella species*, *Campylobacter* species, *Firmicutes* bacteria, *Bartonella* species, *Rickettsia* species, *Yersinia* species, *Francisella* species, *Brucella* species, *Bordetella* species, *Burkholderia* species, *Pseudomonas* species, *Shigella* species, *Chlamydophila* species, *Legionella* species, *Listeria* species, *Corynebacterium* species, *Enterococcus* species, *Escherichia* species, *Haemophilus* species, *Helicobacter* species, *Leptospira* species, *Mycoplasma* species, *Neisseria* species, *Treponema* species, or *Vibrio* species.

The method and system of the present application is useful in releasing DNA/RNA from fungi. The fungus can be, for example, *Saccharomyces, Candida, Aspergillus, Histoplasma, Pneumocystis, Stachybotrys* or *Cryptococcus*.

Periodate Extraction Compositions

Periodates can exist in many forms, which include, meta- and ortho-periodate ($IO_4^-$ and $IO_6^{-5}$, respectively), which are anions formed from iodine and oxygen and are commonly found as salts with potassium (e.g. $KIO_4$) or sodium (e.g. $NaIO_4$). At least four series of periodates are known in aqueous solutions, namely orthoperiodic ($H_5IO_6$), periodic ($HIO_4$), mesoperiodic ($H_3IO_5$), and triperiodic ($H_7I_3O_{14}$) acids [N. N. Greenwood and A. Earnshaw, *Chemistry of the Elements*, $2^{nd}$ *Edition*, Butterworth Heinemann, Oxford, Chapter 17, pp. 872-875 (1998)]. In solution, periodates can be oxidizing agents and are utilized in molecular biochemistry for the purpose of opening saccharide rings and labelling RNA. Periodate cleaves the bond between adjacent carbon atoms having hydroxyl groups (cis-glycols) in synthetic polymers and natural poly- and monosaccharide, creating two aldehyde groups. These aldehydes can be used in two types of coupling reactions with primary amine- or hydrazide-activated labelling/tags, immobilization supports and cross-linking reagents. Periodic acid is also used in the histological stain, Periodic acid-Schiff (PAS), a staining method used to detect glycogen and other polysaccharides in tissues. To the inventors' knowledge, however, periodate has never been used previously for the extraction of DNA and/or RNA from microorganisms.

Periodate extraction compositions are aqueous solutions of periodate that can comprise from about 0.1 mM to about 100 mM, preferably 5 mM to about 30 mM periodate when mixed with the sample, which can be meta-periodate, ortho-periodate or any combination thereof. Compositions having periodate at concentrations as low as 5 mM periodate at slightly alkaline pH, together with heat, release a significant amount of DNA from hardy bacteria and spores, including, without limitation, *Mycobacterium, Clostridium* and *Bacillus* species. Concentrations of periodate up to 25-30 mM in a sample are also successful in efficiently releasing DNA from microorganisms in said sample. Even higher concentrations of periodate are likely to be successful, but undesired side-reactions may occur. The maximum practical solubility of sodium periodate is about 400 mM making it potentially difficult to produce highly concentrated compositions or stock solutions for manufacturing purposes.

To circumvent the solubility issues of periodates at high concentrations, they can be added to the composition in the form of periodic acid, which can be neutralized using a base such as NaOH. Alternatively, the periodate is introduced in the form of a periodate salt, such as sodium periodate (also referred to herein as NPI), potassium periodate or lithium periodate. The use of the sodium salt of periodate ($NaIO_4$), is preferred over the potassium and lithium salts because of its higher solubility. Alternatively, sodium persulfate ($Na_2S_2O_8$), potassium persulfate and ammonium persulfate can be used to release nucleic acid from microorganisms and spores.

While a simple solution of sodium periodate in water and mixed with a sample does extract nucleic acids from microorganisms, the action of periodate is pH dependent. At a pH from about 5 to about 11, DNA and RNA extraction is observed, with RNA integrity better preserved at closer to neutral pH. In certain embodiments, the extraction composition of the present application is buffered to a pH of from about 6.5 to about 11, or from about 8.0 to about 10.5, or from about 9.5 to about 10.5. In one embodiment, to determine the optimal pH range, the extraction composition is buffered using a combination of buffering agents. For example, the composition can be buffered using a combination of phosphoric acid (pKa's 2.15, 7.20, 12.38), acetic acid (pKa 4.76) and boric acid (pKa 9.24).

Optionally, the periodate extraction compositions can comprise additional components, including lithium salts, detergents and/or chelators. In a specific embodiment, the periodate extraction composition additionally comprises LiCl, SDS and/or CDTA. Optionally, the composition additionally comprises glycine or borate as buffering agents. Beneficially, these additional components help to ensure the nucleic acids remain intact during their extraction from microorganisms and processing of biological samples for subsequent downstream molecular tests (e.g. PCR, microarrays). The additional components can also assist in liquefying the sample and conferring stabilization during handling. If the sample is immediately collected into a periodate composition with these additional components, nucleic acids will be optimally preserved from the point of collection, during transport and storage of the sample, allowing processing of the sample to extract nucleic acids, and culminating in the test of interest.

Optionally, the extraction composition without periodate containing LiCl, SDS and/or CDTA and/or glycine or borate as buffering agents can be used to preserve nucleic acids in the sample from the point of collection, during transport and storage until nucleic extraction is required. At that point, periodate can be added and processing of the sample to extract nucleic acids can be carried out, culminating in the test of interest.

Method of Nucleic Acid Extraction

The present application further provides a method of extracting nucleic acid from a sample comprising a microorganism. The method comprises contacting a sample containing microorganism with a composition comprising periodate and heating the resulting mixture.

In accordance with particular embodiments, the method comprises the following steps:

Preparing a suspension of microorganisms: In one example, for example, when the microorganisms are broth cultures of bacteria, the cells are collected by centrifugation and washed (e.g., two times with saline) to remove interfering contaminants that may be present in a complex culture medium. The washed cells (about $5-20 \times 10^8$) should be well suspended in water (e.g., about 200 µL).

Adding periodate extraction composition: typically an equal volume of extraction composition is mixed with an equal volume of cell suspension (e.g., 200 µL of extraction reagent is mixed with 200 µL of cell suspension).

Heating the suspension: The heating step is usually performed with the suspension from the previous step in a closed tube. Typically the heating step is performed at a temperature of 45° C. or higher, or at a temperature from about 50° C. to about 100° C., and a time from about 15 min to about 60 minutes. Longer times and higher temperatures can be more effective in releasing DNA, but the released DNA may be partially degraded. Almost 100% release of DNA from periodate-treated *Mycobacterium smegmatis* occurs with heating at 80° C. for about 20 min, with minimal DNA degradation.

In a specific embodiment, the sample is first treated with a stabilization or pretreatment composition prior to addition of the periodate extraction composition. In one example of such a method, the following steps can be performed:

1) collecting a sample, such as a sputum sample, (for example, in a remote setting) in a stabilization reagent such as Oragene® or OMNIgene®, which stabilizes nucleic acid under ambient conditions;

2) transporting the stabilized sample to a laboratory with no requirement for cold chain (e.g., no refrigeration);

3) adding the periodate composition to the stabilized sample and heating to rapidly and effectively release substantially all nucleic acids from tough microorganisms (e.g., *M. tuberculosis*) and spores and to render the sample non-infectious;

4) rapidly, cost-effectively, processing the treated sample to isolate the nucleic acid released in step 3; and, optionally, 5) performing one or more diagnostic tests using the released nucleic acid.

As a result of the improved release of nucleic acid in comparison to existing technologies, the present periodate treatment can lead to increased sensitivity of diagnostic tests and more accurate diagnosis or determination of the effectiveness of treatment regimens.

The present application further provides a kit for DNA extraction. The kit includes an extraction composition comprising periodate at a concentration of from about 5 mM to about 30 mM and a buffer at a pH of from about 7 to about 13. As described above, the extraction composition can comprise additional components, including a lithium salt, a denaturing agent and/or a chelator. The kit can additionally comprise instructions for performing the above described extraction method, a reagent container(s) and/or a sample receiving container.

Method for Decontamination/Disinfection

The present application further provides a method for decontaminating or disinfecting a surface, for example, of a device, instrument or structure. The method comprises contacting a surface with a composition comprising periodate and heating the surface.

As has been demonstrated herein, the method of treating a microorganism with a composition comprising periodate and heat results in release of DNA from the microorganism. A consequence of this release of DNA is that the microorganism is no longer viable. Example 12 below demonstrates the ability of the present periodate composition plus heat to render three hardy bacteria non-viable.

Typically the heating step in the method of decontaminating or disinfecting is performed at a temperature of 45° C. or higher, or at a temperature from about 50° C. to about 100° C., and a time from about 15 min to about 60 minutes. Longer times and higher temperatures can also be used in the present method as they can be more effective in releasing DNA and decontaminating or disinfecting the surface. Heat can be applied to the surface using various means, such as, but not limited to, heat lamps, radiant heating systems and ovens.

Method for Quantification of Total DNA in a Microbial Suspension

The present application provides a method for quantitation of total DNA in a sample, including a microbiological sample. This method is used to establish the total amount of DNA in a sample to be used as a reference to calculate the efficiency of release of DNA by the compositions described herein.

It is well known that exposure to relatively mild acid conditions can cause DNA degradation (breaks in the backbone). Degradation occurs in two steps. First, acid catalyzes depurination of the DNA, i.e., release of the purine nucleobases (adenine and guanine), but not the pyrimidine nucleobases (thymine and cytosine). The result is a fairly stable structure called apurinic acid. Eventually, the backbone breaks at apurinic sites by 3-elimination, releasing deoxyribose and phosphate; this process is hastened by treatment with alkali or certain catalysts [e.g., K. Burton, M. R. Lunt, G. B. Petersen, J. C. Siebke, Studies of Nucleotide Sequences in Deoxyribonucleic Acid, *Cold Spring Harbor Symposium on Quantitative Biology*, vol. 28, pp. 28-34 (1963)].

In contrast, depurination of RNA by mild acid treatment has not previously been studied in any detail. It is generally understood that purines of RNA is more stable than of DNA, but a side-by-side comparison has not been made. Conversely, it is known that RNA is easily degraded by treatment with mild alkali, whereas the backbone of DNA is very stable under these conditions [(e.g., G. Schmidt and S. J.

Thannhauser, A method for the determination of deoxyribonucleic acid, ribonucleic acid, and phosphoproteins in animal tissues. *Journal of Biological Chemistry* vol. 161, pp. 83-89 (1945)]. Alkali-catalysed breakdown of the RNA backbone proceeds in two steps. First, the phosphodiester bond linking the ribose 3'-hydroxyl of one nucleotide to the 5'-hydroxyl of the neighbouring nucleotide is transferred (not broken) to the 2'-hydroxyl of the first nucleotide. This results in chain scission without hydrolytic cleavage of a phosphoester bond. The resultant 2', 3'-cyclic phosphodiester is relatively stable, but it can be slowly cleaved on further treatment with alkali to either the 2'-phosphomonoester or 3'-phosphomonoester with approximately equal frequency. Under these conditions, the DNA backbone is very stable, since its sugar (deoxyribose) lacks a 2'-hydroxyl adjacent to the 3'-hydroxyl so the facile first step, formation of a 2', 3'-cyclic phosphodiester, is not possible.

Although the scientific literature contains general background information about the reactions described above, detailed, specific conditions of acid treatment that produce near-quantitative depurination of DNA, while causing little or no depurination of RNA, have not previously been described.

Having well-defined conditions under which adenine and guanine are quantitatively released from DNA, but not from RNA, has great utility. It allows for sensitive and reproducible quantification of DNA in complex biological samples and microorganisms, something that is at present difficult, with no amplification steps prior to detection. For example, sample preparation and DNA purification are necessary first steps before assay methods such as UV absorbance or fluorescent DNA-binding dyes can be applied. Chemical methods based upon diphenylamine or DABA (diaminobenzoic acid) are subject to interference by compounds in biological samples, including complex polysaccharides [G. M. Richards, Modifications of the diphenylamine reaction giving increased sensitivity and simplicity in the estimation of DNA. Analyt. Biochem. 57, 369-376 (1974); J. M. Kissane, E. Robins, The fluorometric measurement of deoxyribonucleic acid in animal tissues with special reference to the central nervous system. J. Biol. Chem. 233, 184-188 (1958)]. Surprisingly, there is currently no simple, precise method to determine the amount of DNA (or RNA) present in a suspension of intact, unprocessed microorganisms. Having such information is critical to determining the efficiency by which any existing or novel method or composition actually releases DNA from a suspension of organisms. Efficiency of extraction (E) is defined as amount of DNA extracted by a treatment (DNAe) divided by the total amount of DNA initially present in the untreated sample (DNAt).

$$E = \frac{DNAe}{DNAt}$$

The presently described Acid-Extraction/HPLC method was developed to allow such determination.

Accordingly, the present application provides a method for determination of total DNA in a sample. The method is described in detail in Example 1 below. Generally, the method comprises the step of heating a nucleic acid containing sample with HCl (an "acid hydrolysis" step), or another acid (such as, for example, concentrated formic acid), followed by neutralization of the sample prior to HPLC analysis using a reverse phase HPLC column (e.g., Gemini-NX column). The mobile phase can be selected from various solvents or mixtures of solvents based on the specific column used, etc. Selection of the appropriate mobile phase would be within the standard abilities of a worker skilled in the art. In one embodiment, the mobile phase is 2% methanol, 1 mM CDTA, 30 mM ammonium acetate, adjusted to pH 6.3 with sodium monophosphate. Optionally, the method additionally comprises a step to allow quantification of RNA. To determine the amount of RNA in a sample, NaOH is added, after the step of heating the sample with HCl, to an excess of 0.1 N over the amount of HCl added and incubated at 100° C. for 15 minutes.

The Area Under the Curve ("AUC") for HPLC peaks corresponding to adenine (representing DNA) and to 2' or 3' adenosine monophosphate (2'- and 3'-AMP) (representing RNA) was calculated using TotalChrom Navigator software (Perkin Elmer). Standard curves can be generated using known concentrations of these pure analytes (adenine from Alfa Aesar; 2'-3'-AMP (mixture) from Sigma-Aldrich).

To gain a better understanding of the invention described herein, the following examples are set forth. It should be understood that these examples are for illustrative purposes only. Therefore, they should not limit the scope of this invention in any way.

EXAMPLES

Example 1: Acid-Extraction HPLC Method for Measuring Total DNA in a Sample

Table 1 outlines details of the Acid-Extraction/HPLC Method developed by the present inventors to precisely measure the total amount of nucleic acid in raw or unprocessed microorganisms/samples, as well as nucleic acids released from such microorganisms/samples resulting from treatment with the invention.

TABLE 1

Typical protocol for releasing nucleic acids from hardy microbes using the presently described extraction method and for measuring DNA and RNA in intact and treated microbes

| | | |
|---|---|---|
| 1. | Prepare suspension of microbes or sample | For bacterial cultures, cells should be collected by centrifugation and washed twice with saline to remove interfering contaminants that may be present in complex culture medium and cellular . debris The washed cells (about 5-20 × 10$^8$) should be well-dispersed in 200 μL water. For determining the total amount of nucleic acids in untreated bacteria, remove a known aliquot of the washed cell suspension and proceed to step 5. |
| 2. | Add bacterial lysing reagent | Typically, an equal volume of invention/reagent (200 μL) is mixed with 200 μL of cell suspension. |

TABLE 1-continued

Typical protocol for releasing nucleic acids from hardy microbes using the presently described extraction method and for measuring DNA and RNA in intact and treated microbes

| | | |
|---|---|---|
| 3. | Heat the suspension in a closed tube | Typically, temperatures of 50° C. to 100° C. and times of 15 to 60 minutes are used. Longer times and higher temperatures may be more effective in releasing DNA, but the released DNA may be more degraded. Over 90% DNA can be released from *Mycobacterium smegmatis* with 80° C. incubation for 20 min, with little DNA degradation. |
| 4. | Centrifuge, discard pellet, and retain supernatant | Centrifuge the suspension at 14,000 rpm for 4-10 minutes. Keep supernatant and discard the pellet of insoluble material. |
| 5. | Acid hydrolysis | Add HCl to supernatant fractions (which contain a pH buffer) to final concentration of 0.25N. For suspension of untreated bacteria from step 1, add HCl to 0.20N. |
| 6. | Heat | Incubate at 60° C. for 60 minutes. Vortex during incubation at 0, 30 and 60 minutes. |
| 7. | (Optional) | Where required to determine the amount of RNA in a sample, add NaOH to an excess of 0.1N over the amount of HCl added and incubate at 100° C. for 15 minutes. |
| 8. | Centrifuge, discard pellet, and retain supernatant | Cool samples to room temperature, Centrifuge at 14,000 rpm for 4-10 minutes to remove colloidal material and obtain a clear supernatant. Retain supernatant and discard the pellet of insoluble material. |
| 9. | Neutralize supernatant | Neutralize each supernatant with ADA buffer (N-(2-Acetamido)iminodiacetic acid) or HCl (if NaOH was added) to approximately pH 6.3. |
| 10. | Analyze by HPLC | Analyze samples by reverse phase-HPLC (High-Pressure Liquid Chromatography). A Perkin Elmer series 200 system with Series 225 auto-sampler and with UV detection at 260 nm was used. The column was a reverse phase Gemini-NX column (Phenomenex). The mobile phase contained 2% methanol, 1 mM CDTA, 30 mM ammonium acetate, adjusted to pH 6.3 with sodium monophosphate. Samples (40 µL) were injected. The Area Under the Curve ("AUC") for peaks corresponding to adenine (representing DNA) and to 2' or 3' adenosine monophosphate (2'- and 3'-AMP) (representing RNA) was calculated using TotalChrom Navigator software (Perkin Elmer). Standard curves were generated using known concentrations of these pure analytes (adenine from Alfa Aesar; 2'-and 3'-AMP from Sigma-Aldrich). |

Example 1A: Pure DNA. Optimal Acid-Extraction Conditions for Complete Release of Adenine from DNA In this example, the amount of adenine released from pure genomic DNA by acid treatment for different periods of time was measured. Four hundred and sixty nanograms of pure canine DNA (Novagen) was subjected to the Acid-Extraction Method for the indicated times at 60° C. The results are shown in FIG. 1. The error bars indicate the SEM of triplicate samples.

The results indicate that a 60 minute period of incubation at 60° C. is sufficient to release the maximum amount of adenine from DNA. The vast majority of adenine is released by 40 minutes and no further adenine is released by 80 minutes of treatment, indicating complete depurination of adenine by 60 minutes.

Example 1B: Optimal Acid Concentration for Release of Adenine from Intact Bacterial Cells

Figure 2:
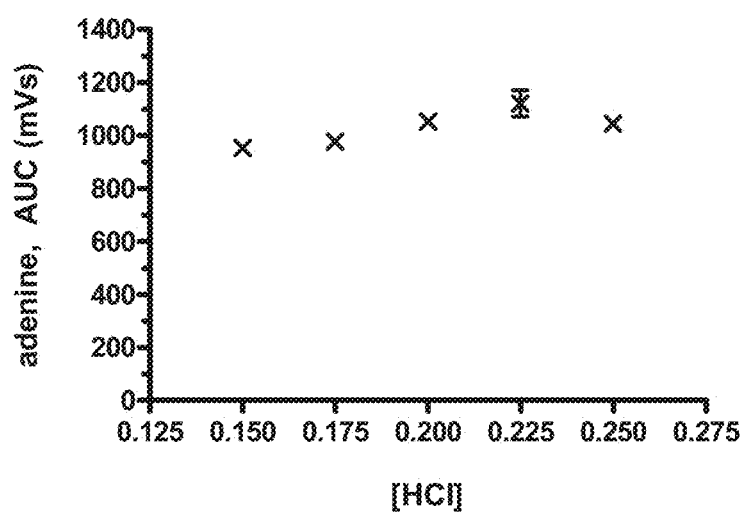
FIG. 2 graphically depicts results of the release of adenine from the DNA present in a suspension of intact *Bacillus subtilis* cells as a function of acid concentration.

*Bacillus subtilis* cells were incubated 60 minutes at 60° C. with different concentrations (Normal) of HCl as shown in FIG. 2. Error bars, average and range of duplicates; where no error bars are shown, the value of the ranges are within the symbols.

The results indicate that the maximal release of adenine from intact *B. subtilis* cells occurs with an HCl concentration in the range of about 0.20-0.25 N.

Example 1C. CFU Method to Estimate DNA Content Compared to Acid-Extraction HPLC Method This experiment was designed to compare the amount of DNA present in a bacterial culture by counting the number of bacterial cells (as estimated by Colony Forming Units (CFU)) with the amount of DNA calculated from the AUC for adenine using the Acid-Extraction HPLC Method.

The CFU Method is a classical method used to estimate the number of viable bacterial cells in a sample. However, it is time-consuming and has theoretical limitations. Bacteria typically grow in small clumps. Therefore, what is scored as a visible "colony" of bacteria can actually arise either from a single cell or from a clump of 2 or more cells. Also, any non-viable cells in a culture will contain DNA but will not form colonies. These two factors tend to underestimate the actual number of bacterial cells in a suspension. From estimates of cell number and "literature" knowledge of DNA per cell, the total amount of DNA in a cell suspension can be calculated.

By contrast, the Acid-Extraction HPLC Method is a direct, chemical method for estimating the total amount of DNA in a cell suspension. The inventors developed this method primarily to demonstrate the effectiveness of the invention for releasing nucleic acids from hardy microorganisms and spores. The method (outlined in detail above) is based upon the release of purines from DNA and extraction of adenine from cells, and then the detection and quantification of adenine using HPLC. A known amount of adenine can be converted to a known amount of DNA from the base composition of the DNA. For example, the conversion factor from adenine to DNA is 10, for DNA having a GC content of 48%.

This example compares the CFU and Acid-Extraction HPLC Methods for their ability to measure DNA in a suspension of *Bacillus subtilis*. To estimate CFU, a suspension of log phase bacteria (grown in tryptic soy broth (TSB)) was washed with a solution of cold 25 mM Tris, 150 mM NaCl, pH 7.6 and split into 2 portions. One portion was serially diluted in TSB, in triplicate, and spread on the surface of a tryptic soy agar plate. After 18 hours growth at 37° C., the number of visible colonies was enumerated. The other portion was split into three tubes and centrifuged. The pellets were brought up in 200 µL of 0.2 N HCl, incubated at 60° C. for 60 minutes, neutralized with ADA, and analyzed by HPLC.

From published genome sequence data, the genome size for *Bacillus subtilis* was taken to be 4880 ng/$10^9$ cells.

TABLE 2

Standard CFU Method

| Sample | CFU, at $10^{-7}$ dilution | CFU, at $10^{-6}$ dilution |
|---|---|---|
| 1 | 19 | 255 |
| 2 | 27 | 263 |
| 3 | 32 | 279 |
| CFU of the original culture (Average) | $2.6 \times 10^8$ | $2.7 \times 10^8$ |

TABLE 3

Acid-Extraction HPLC Method

| Sample | AUC*, ade** | Ade concentration (nmoles/mL) | Total DNA (ng) | No. of Bacteria calculated assuming 4880 ng/$10^9$ cells |
|---|---|---|---|---|
| 1 | 204.92 | 3.963 | 1556 | $3.2 \times 10^8$ |
| 2 | 217.47 | 4.214 | 1655 | $3.4 \times 10^8$ |
| 3 | 208.55 | 4.036 | 1585 | $3.3 \times 10^8$ |
| Average | 210.31 | 4.071 | 1599 | $3.3 \times 10^8$ |

*AUC, Area under the curve,
**ade, adenine

The CFU and Acid-Extraction HPLC Methods provided very similar estimates of bacterial counts in a pure culture of *B. subtilis*. The Acid-Hydrolysis HPLC Method provided about a 20% higher estimate, which is in keeping with the expected underestimate of cell number by the CFU method discussed above. This example supports the notion that the Acid-Extraction HPLC Method effectively releases adenine from intracellular DNA, allowing its detection by HPLC.

Example 1D: Lysozyme/Detergent Method to Estimate DNA Content Compared to Acid-Extraction HPLC Method This experiment was designed to compare the amount of DNA released from Gram-positive (i.e., lysozyme-sensitive) *B. subtilis* by an enzymatic lysis method with the amount of DNA measured in intact cells using the Acid-Extraction HPLC Method. Gram-positive organisms such as *B. subtilis* are known to be very sensitive to lysis by treatment with the enzyme lysozyme followed by treatment with SDS (e.g., B. M. Chassy. A gentle method for the lysis of oral streptococci. Biochem Biophys Res Commun 68: 603-608 (1976)). Lysozymes are glycoside hydrolases that function by attacking peptidoglycans found in the cell walls of bacteria, especially Gram-positive bacteria. If the Acid-Extraction HPLC Method is indeed effective, the amount of adenine released by acid treatment of whole cells and detected by HPLC should be similar to the amount released by lysis of cells with lysozyme plus SDS.

Lysozyme Protocol:

*Bacillus subtilis* was grown to exponential phase in 1 mL of LB broth and harvested by centrifugation.

Cells were washed in ice-cold TE buffer (10 mM Tris, 1 mM EDTA, pH 8.0). The pellet was brought up in 1 mL TE buffer, split into four aliquots and washed once more with TE.

Two of the pellets were resuspended in 950 µL of lysozyme (1 mg/mL in TE), and incubated 45 minutes at 37° C.

50 µL of 10% SDS was added to a final concentration of 0.5%.

SDS was removed by addition of KCl (final concentration 0.1 M), incubation at 0° C. for 5 minutes and centrifugation for 5 minutes. The supernatants were transferred to fresh tubes; the pellets were discarded.

Samples were subjected to the Acid-Extraction HPLC Method.

The remaining two untreated pellets were brought up in 500 µL $H_2O$ and subjected to the Acid-Extraction HPLC Method.

TABLE 4

Acid-Extraction HPLC Method Detects the Same Amount of DNA in Intact *B. subtilis* Cells as is Released after Lysozyme/SDS-Treatment of the Same Cells

| *B. subtilis* cell suspension treated with: | AUC, adenine | | Corrected for dilution | | AUC (average), adenine |
|---|---|---|---|---|---|
| Lysozyme/SDS | 189* | 193* | 378 | 386 | 382.0 |
| Acid-Extraction HPLC | 376 | 395 | 376 | 396 | 385.5 |

*replicate samples

The amount of adenine released from intact *B. subtilis* by acid-treatment was essentially identical to the amount of adenine released by lysozyme/SDS treatment, a procedure expected to release 100% of the DNA by lysis of 100% of the cells. This provides strong evidence that the Acid-Extraction HPLC Method is a very effective tool for determining the amount of DNA in intact, Gram-positive bacterial cells.

Example 1E: Bead Beating Method to Estimate DNA Content Compared to Acid-Extraction HPLC Method from *Bacillus subtilis*

This study was performed in order to compare the initial amount of DNA in intact bacterial cells (estimated by the Acid-Extraction HPLC method) to the amount of DNA released from the same bacteria using a 'bead-beating' method. The procedure used for the Acid-Extraction HPLC was as described above. The procedure used for the Bead-Beating method is summarized below:

Multiple 2 mL aliquots of *B. subtilis* stationary phase culture were harvested by centrifugation and washed twice by centrifugation in a cold solution of 25 mM Tris, 150 mM NaCl, pH 7.6 (TBS).

Bead-beating was performed in a Mini-BeadBeater-16 (BioSpec) according to the manufacturer's instructions. In brief, washed bacterial pellets were suspended in 500 μL of TBS and transferred to a screw-cap polypropylene microtube containing about 100 μL of 100 m glass beads (Polyscience).

The tube was secured to the instrument and vigorous agitation was performed in two 1-minute cycles at 3,450 oscillations/minute. The sample was cooled on ice for 1 minute between cycles.

The suspension was transferred to a 1.5 mL microcentrifuge tube and unbroken cells and debris were removed by centrifugation 5 minutes, 14,000 rpm in a microcentrifuge.

The supernatant was removed and HCl was added to a final concentration of 0.2 N. Samples were incubated for 60 minutes at 60° C.

To compare the amount of DNA in intact cells to the cell lysate generated by bead-beating, an aliquot of intact *B. subtilis* cells was incubated in 0.2 N HCl for 60 minutes at 60° C. (the Acid-Extraction method).

All samples were centrifuged 4 minutes, 14,000 rpm to remove debris and a 40 μL portion was applied to a reverse phase Gemini-NX column (Phenomenex) and analysed by HPLC.

Figure 3:
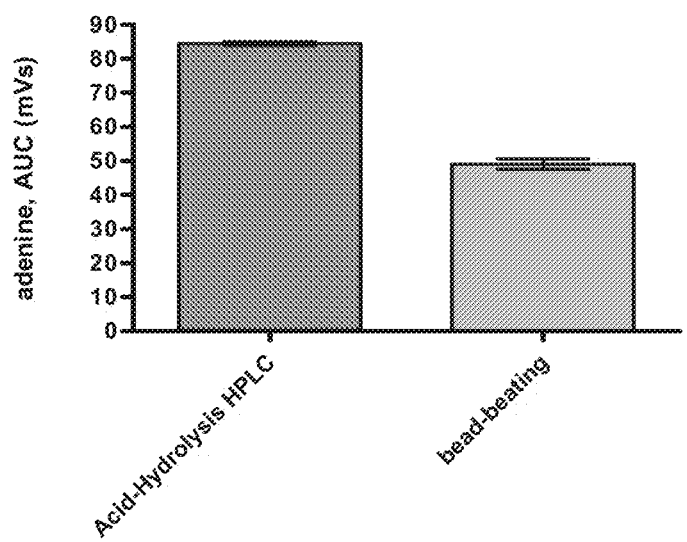
FIG. 3 graphically depicts results of a comparison of total DNA detected by the Acid-Extraction method and by the bead-beating method.

The results of this study are provided in FIG. 3. The error bars represent the range of duplicate analyses.

Although it is commonly assumed that "bead-beating" is highly efficient at disrupting bacterial cells and releasing DNA, this is not necessarily the case. This experiment provides additional evidence that the Acid-Extraction HPLC Method provides a truer and more consistent representation than bead-beating of the actual amount of DNA in the initial cell suspension. In other experiments, the amount of DNA released by bead-beating has ranged up to 100%, that is, in an amount equal to the acid-extraction method. Because it provides variable results, the bead beating method is not a reliable way to estimate the amount of DNA present in a suspension of intact bacterial cells.

Example 2: Comparison of Periodate to Other Per-Halogenated and Oxidizing Compounds In this example, a series of per-halogenated and oxidizing compounds were evaluated for their effectiveness at releasing nucleic acids from bacterial cells. Sodium (meta)periodate, sodium perborate tetrahydrate, sodium perchlorate, sodium persulfate (each at 15 mM) were used to treat aliquots of a suspension of *Bacillus subtilis* vegetative cells (i.e., not spores). Following a 20-minute incubation at 70° C., with or without the test compounds, the supernatant fractions of each suspension (as well as the untreated bacterial cells) were subjected to the Acid-Hydrolysis HPLC Method and the percentage of DNA released from the bacteria by each treatment was calculated.

Experimental Method and Materials

Prepared BD buffer (2% SDS, 5 mM Li-CDTA, 250 mM LiCl, 50 mM glycine, pH 10.5).

300 mM stock solutions of test compounds were freshly prepared in distilled water for each of the following: sodium (meta)periodate (Sigma-Aldrich, Cat. No. S-1878), sodium perborate tetrahydrate (Sigma-Aldrich, Cat. No. 71840), sodium perchlorate (Sigma-Aldrich, Cat. No. 410241), and sodium persulfate (Sigma-Aldrich, Cat. No. 216232).

A 10-fold dilution of each stock solution from the above step was made by transferring 100 μL (or 100 μL of water for negative control) to five tubes containing 0.8 mL of BD buffer.

Working Test Solutions. Water (100 μL) was added to each tube to bring the final concentration of each stock solution to 30 mM in 80% BD buffer.

Washed pellets were prepared from equal volumes of a suspension of stationary phase *Bacillus subtilis*.

Each pellet was suspended in 300 μL of water.

An equal volume (300 μL) of each Working Test Solution, (i.e., 30 mM sodium (meta)periodate, sodium perborate tetrahydrate, sodium perchlorate, or sodium persulfate in 80% BD buffer or water (negative control)) was added to each bacterial suspension and mixed well.

The mixtures were heated at 70° C. for 20 minutes.

Following heating, each mixture was centrifuged at 14,000 rpm for 4 minutes. The supernatant was retained. The pellet of insoluble material was discarded.

Hydrochloric acid was added to supernatant fractions to a final concentration of 0.2 N.

The mixture was heated at 60° C. for 60 minutes.

A 150 μL aliquot of each sample was neutralized with 100 μL of ADA buffer, pH 8.0.

Each sample was then analyzed by HPLC to determine the AUC for adenine. Three washed pellets of untreated cells (step 5) were subjected directly to the Acid-Hydrolysis HPLC Method to determine the total amount of DNA (adenine) in each bacterial pellet.

Results

The results are summarized in Table 5, below:

TABLE 5

Comparison of DNA Released from *B. subtilis* by Per-halogenated and Oxidizing Compounds.

| Sample | Control (no reagent) | | Periodate | | Perborate | | Perchlorate | | Persulfate | |
|---|---|---|---|---|---|---|---|---|---|---|
| | AUC, Ade | % DNA release | AUC, Ade | % DNA release | AUC, Ade | % DNA release | AUC, Ade | % DNA release | AUC, Ade | % DNA release |
| 1 | 79 | 6.2 | 594 | 46.6 | 70 | 5.5 | 79 | 6.2 | 202 | 15.9 |
| 2 | 89 | 7.0 | 611 | 48.0 | 80 | 6.3 | 85 | 6.7 | 187 | 14.7 |
| 3 | 89 | 7.0 | 476 | 37.4 | 82 | 6.4 | 81 | 6.4 | 182 | 14.3 |
| Average | 85.7 | 6.7% | 560.3 | 44.0% | 77.3 | 6.1% | 81.7 | 6.4% | 190.3 | 15.0% |

Conclusion

Of the 4 compounds tested at a single concentration (15 mM), only sodium (meta)periodate and sodium persulfate released more DNA than the control: 44% and 15% of the total DNA from *Bacillus subtilis*, respectively. In contrast, the other per-halogenated/oxidizing compounds released no more DNA than the control (6.7%).

This example demonstrates that persulfate can also function to increase nucleic acid release in a manner similar to periodate.

Example 3: Effect of pH on Periodate Extraction

In testing the effectiveness and dose-dependence of NPI (sodium (meta)periodate) across a range of pH it was necessary to consider various factors including (i) potential reaction of NPI with the buffer itself (ii) different forms of NPI may exist at different pH values (e.g., metaperiodate, orthoperiodate) and (iii) NPI has reduced solubility at elevated pH.

For these studies, a buffer system was used comprising 3 different buffering weak acids covering a range of pKa values and adjusted to the desired pH with a single base. The acids (pKa values) were phosphoric acid (2.15, 7.20, 12.38), acetic acid (4.76) and boric acid (9.24). The initial solution of combined acids (20 mM each) had a pH of 1.9 (Table 6) (referred to herein as "PAB" buffer solutions). PAB buffer solutions were adjusted with 5 N NaOH to attain the desired pH values for experimentation (Table 7).

PAB buffer solutions at pH 3.7, 5.5, 7.4 and 9.4 were tested alone and in combination with NPI at three different concentrations (6, 12 and 18 mM final). The buffer, with or without the NPI, was added to pellets of washed *Mycobacterium smegmatis*. Three different concentrations of NPI were tested to determine whether a dose-response exists in this concentration range for the release of DNA from bacterial cells. Thus, *M. smegmatis* cells were heated with PAB buffer solutions containing different concentrations of NPI over a range of pH values to measure the amount of DNA released using the Acid-Extraction HPLC Method described herein.

PAB Buffer Solutions

The components listed in Table 6 were mixed and the resulting mixture was stirred overnight to allow the boric acid to fully dissolve. The initial pH was measured at 1.9.

TABLE 6

Composition of the PAB Buffer System

| PAB Buffer System Chemicals | Formula Weight & Concentration | Amount | Final Concentration |
|---|---|---|---|
| o-Phosphoric acid (85%) | F.W. 98; Density 1.685 | 0.465 mL (0.78 grams | 20 mM |
| Glacial acetic acid | 17.4N | 0.46 mL | 20 mM |
| Boric acid powder | F.W. 61.8 | 0.494 grams | 20 mM |
| Water | | to 200 mL | |

TABLE 7

Final pH Values of PAB Buffer System Solutions

| PAB Buffer System Solutions | Adjust with 5N NaOH to desired pH |
|---|---|
| PAB buffer 3.7 | 3.7 |
| PAB buffer 5.5 | 5.5 |
| PAB buffer 7.4 | 7.4 |
| PAB buffer 9.4 | 9.4 |

Following preparation, the PAB buffer solutions were stored at 4° C.

Experimental Method

Fresh working solutions (PAB buffer solutions±NPI) were prepared by addition of 0, 20, 40 or 60 µL of 300 mM NPI stock (in water) to 1,000, 980, 960 or 940 µL (respectively) of each PAB buffer solution. The working solutions were used within 3 hours of preparation.

Washed pellets were prepared from equally distributed, washed suspensions of *Mycobacterium smegmatis* (where water was used for the last wash).

Each pellet was suspended in 200 µL of PAB buffer solutions±NPI (6, 12 and 18 mM final), in triplicate. The resulting mixture was heated at 70° C. for 20 minutes.

The mixture was centrifuged at 14,000 rpm for 4 minutes. The supernatant was retained and the pellet of insoluble material was discarded.

HCl was added to supernatant fractions to final concentration of 0.2 N. The acidified fractions were heated for 60 minutes at 60° C.

Each 150 µL sample was neutralized with 100 µL of ADA buffer (N-(2-acetamido)iminodiacetic acid), pH 8.0. The samples were then analyzed by HPLC.

Results

The results are summarized in Tables 8 and 9 below.

TABLE 8

Release of DNA into the Supernatant from *M. smegmatis* Cells Treated with NPI as a Function of pH*

| NPI (mM) | PAB buffer, pH 3.7** | | | | % DNA released*** | PAB buffer, pH 5.5** | | | | % DNA released*** |
|---|---|---|---|---|---|---|---|---|---|---|
| | 1 | 2 | 3 | Ave. | | 1 | 2 | 3 | Ave. | |
| 0 | 20.9 | 27.3 | 19.7 | 22.6 | 2.1% | 53.7 | 50.5 | 51.0 | 51.7 | 4.8% |
| 6 | 384.3 | 409.7 | 416.6 | 403.5 | 37.4% | 442.3 | 477.8 | 431.6 | 450.6 | 41.8% |
| 12 | 336.2 | 333.8 | 353.1 | 341.0 | 31.6% | 417.7 | 390.0 | 485.1 | 430.9 | 40.0% |
| 18 | 350.6 | 364.8 | 383.9 | 366.4 | 34.0% | 405.3 | 454.0 | 403.1 | 420.8 | 39.0% |

| NPI (mM) | PAB buffer, pH 7.4** | | | | % DNA released*** | PAB buffer, pH 9.4** | | | | % DNA released*** |
|---|---|---|---|---|---|---|---|---|---|---|
| | 1 | 2 | 3 | Ave. | | 1 | 2 | 3 | Ave. | |
| 0 | 120.0 | 128.8 | 120.0 | 122.9 | 11.5% | 98.4 | 104.3 | 103.7 | 102.1 | 9.5% |
| 6 | 509.4 | 625.4 | 516.2 | 550.3 | 51.1% | 672.1 | 648.5 | 599.9 | 640.2 | 59.4% |
| 12 | 564.1 | 689.0 | 703.6 | 652.2 | 60.5% | 578.0 | 746.8 | 732.5 | 685.8 | 63.6% |
| 18 | 579.5 | 629.1 | 552.4 | 587.0 | 54.5% | 719.6 | 769.3 | 649.6 | 712.8 | 66.1% |

*Bacteria treated with PAB buffer solutions without and with 6, 12 and 18 mM NPI (final) at the indicated pH and with heat prior to analysis of DNA released using the Acid-Extraction HPLC Method described herein. Results of each replicate analysis are shown.
**AUC (area under the curve) for adenine is a measure of the amount of DNA released by the indicated treatment at the indicated pH and measured by HPLC.
***The percentage of DNA released is calculated from the average AUC for adenine released into the supernatant under each pH condition and concentration of NPI, divided by the average amount of adenine that is acid-extracted from untreated bacteria (Table 9).

TABLE 9

Amount of DNA in 3 Replicate Pellets of *M. smegmatis* Cells used in the Experiment of Table 8.

| Pellet 1 | Pellet 2 | Pellet 3 | Ave. | % adenine (DNA) pellet |
|---|---|---|---|---|
| 1217.9* | 1118.7* | 896.5* | 1077.7 | 100.0% |

**AUC (area under the curve) for adenine, a measure of the amount of DNA present in the pellet of untreated cells

Conclusions

A 3-component buffering system was employed to demonstrate the pH-dependent effect on NPI-mediated release of DNA from *Mycobacterium smegmatis*. In the absence of NPI, 2.1-11.5% of DNA was released from *M. smegmatis* during a 20-minute incubation at 70° C. In contrast, the addition of even a low concentration of NPI (6 mM) to the buffer solutions markedly increased the percentage of total DNA released from the same microbes by approximately 9-fold to 37.4-59.4%, in a pH-dependent manner. Surprisingly, increasing the concentration of NPI from 6 mM to 12 mM and even 18 mM lead to only a modest additional release of DNA from bacteria; this was observed only at neutral and alkaline pH values.

Example 4: Release of Nucleic Acids from Spores Using Periodate

*Bacillus subtilis* is a Gram-positive bacterium that can change from a growing, vegetative state to an extremely hardy non-dividing spore, allowing the organism to survive extreme environmental conditions. In general, spores are very resistant to heat (able to survive at 100° C. for several hours), dessication, UV radiation and oxidizing agents.

Sporulation is essentially triggered by a lack of nutrients. The bacterium divides in an asymmetric manner resulting in the formation of a single endospore containing the bacterium's genomic DNA surrounded by a very tough outer wall. In this state, the bacterium can lie in a dormant but viable state for extended periods of time, even centuries. Under favourable environmental conditions, the endospore can be reactivated and revert to the growing (vegetative) state.

Bacterial spores are considered to be amongst the most difficult cell types to break open. Common anti-bacterial agents that destroy vegetative cells, such as household disinfectants (e.g., alcohols, detergents, quaternary ammonium compounds) do not kill endospores. The spore coat is not sensitive to lysozyme. In this example, the efficacy of sodium (meta)periodate for releasing nucleic acids from *Bacillus subtilis* spores was demonstrated.

Preparation of Spores

Single colonies of *B. subtilis* were grown in 2 mL Luria Broth (LB) overnight at 37° C. in an orbital platform shaker at 200 rpm. Bacteria (1 mL) were harvested by centrifugation at 11,000 rpm for 3 minutes; the supernatant was discarded. The bacteria were washed twice by centrifugation in 1 mL of cold sterile $H_2O$ to remove residual LB.

To convert vegetative cells to spores, bacteria were suspended in 200 µL $H_2O$ and added to 100 mL Columbia Broth [J. A. Morello and P. D. Ellner. 1969. New medium for blood cultures. Appl. Microbiol. 17:68-07] containing 0.1 mM manganese chloride.

The mixture was shaken on an orbital platform at 160 rpm at 37° C. for 72 hours to produce approximately $10^8$ spores per mL. The spores were harvested by centrifugation and suspended in 15% ethanol in water.

Prior to use, each spore sample was washed three times with ice-cold water.

To eliminate any remaining vegetative bacteria, the pellet was suspended in 1 mL cold water. Lysozyme solution (400 µL of a 5 mg/mL stock solution in Tris (10 mM), EDTA (1 mM)) was added and the resulting mixture was incubated at 37° C. for 1 hour. The spores were collected by centrifugation and the supernatant discarded.

The spore pellet was suspended in 1 mL of 0.1% SDS and incubated 5 minutes at room temperature. The pellet of spores was collected by centrifugation at 9,000 rpm for 4 minutes; the supernatant was discarded.

To remove any residual cell-free DNA in the preparation, the spores were suspended in 1 mL of 1×DNase buffer (10 mM Tris-HCl, 4 mM $MgCl_2$, 1 mM $CaCl_2$) containing 10 µg pancreatic DNase and incubated at 37° C. for 30 minutes.

The spore suspension was centrifuged at 9,000 rpm for 4 minutes and the supernatant was discarded. The pellet was washed once with water. The pellet of highly purified spores was resuspended in 1.2 mL $H_2O$. The majority of this preparation (800 µL) was used in step 2 of the following experimental method; three other 100 µL aliquots were treated directly with the Acid-Extraction HPLC Method (step 5-8, below) to estimate total DNA content of the spores; the remaining 100 µL aliquot of the spore suspension was treated a second time with lysozyme and SDS (steps 9 and 10, above) to confirm that DNA released from spores was not due to cells that converted to the vegetative state. Acid-extraction/HPLC analysis was then carried out.

DNA Extraction

Reagents BA, BB, BC and BD were prepared with and without sodium (meta)periodate (Table 10).

Aliquots (100 µL) of suspended *B. subtilis* spores (from the above process) were mixed with an equal volume of BA, BB, BC or BD with or without sodium (meta)periodate. The mixture was heated at 70° C. for 20 minutes and then centrifuged at 14,000 rpm for 4 minutes. The supernatant was retained and the pellet of insoluble material was discarded.

Hydrochloric acid was added to supernatant fractions to a final concentration of 0.2 N. The fractions were then heated at 60° C. for 60 minutes. A portion of each sample (150 µL) was neutralized with 100 µL of ADA buffer, pH 8.0. The samples were analyzed by HPLC to determine the AUC for adenine.

TABLE 10

Composition of Reagents Used

| Reagent | SDS (%) | Lithium CDTA (mM) | Lithium chloride (mM) | Sodium borate (mM) | Glycine (mM) | NPI (Sodium (meta) periodate) (mM) | Final pH |
|---|---|---|---|---|---|---|---|
| BA | 4.0 | 50 | 250 | 0 | 0 | 0 | 6.8 |
| BAP | 4.0 | 50 | 250 | 0 | 0 | 30 | 6.8 |
| BB | 4.0 | 5 | 250 | 50 | 0 | 0 | 9.0 |
| BBP | 4.0 | 5 | 250 | 50 | 0 | 30 | 8.9 |
| BC | 0.0 | 0 | 0 | 0 | 0 | 0 | 7.0 |
| BCP | 0.0 | 0 | 0 | 0 | 0 | 30 | 6.5 |
| BD | 2.0 | 5 | 250 | 0 | 50 | 0 | 10.5 |
| BDP | 2.0 | 5 | 250 | 0 | 50 | 30 | 9.4 |

TABLE 11

Effectiveness of Periodate in Different Reagents on DNA Release from Spores Treated at 70° C. for 20 minutes, as measured Using the Acid-Extraction HPLC Method*

| Sample Replicates | Original pellets extracted with acid | BA | BAP | BB | BBP | BC | BCP | BD | BDP | Lysozyme + SDS |
|---|---|---|---|---|---|---|---|---|---|---|
| 1 | 65.3 | 0.0 | 7.9 | 0.0 | 0.0 | 0.0 | 0.0 | 0.0 | 6.0 | 0.0 |
| 2 | 68.5 | 0.0 | 7.0 | 0.0 | 0.0 | 0.0 | 0.0 | 0.0 | 5.9 | 0.0 |
| 3 | 68.0 | 0.0 | 5.2 | 0.0 | 0.0 | 0.0 | 0.0 | 0.0 | 5.0 | 0.0 |
| Average AUC, ade** | 67.3 | 0.0 | 6.7 | 0.0 | 0.0 | 0.0 | 0.0 | 0.0 | 5.6 | 0.0 |
| % DNA released*** | 100.0 | 0.0 | 10.0 | 0.0 | 0.0 | 0.0 | 0.0 | 0.0 | 8.3 | 0.0 |

*B. subtilis spores treated with reagents (Table 10), without and with 15 mM sodium (meta)periodate (final concentration) at the indicated pH and with heat (70° C., 20 minutes) prior to analysis of DNA released using the Acid-Extraction HPLC Method described herein. Results of triplicate analyses are shown.
**AUC (area under the curve) for adenine is a measure of the amount of DNA released from the spores into the supernatant by the indicated treatment and measured by HPLC.
***The percentage of DNA released from spores is calculated from the average AUC for adenine released into the supernatant under each treatment condition, divided by the average amount of adenine acid-extracted from the pellet of untreated spores.

Conclusions

Surprisingly, a low concentration of sodium (meta)periodate present in BAP and BDP reagents together with moderate heat treatment (70° C., 20 minutes) was able to release as much as 10% and 8.3% of DNA, respectively, from spores, the most hardy of organisms. Higher temperatures and longer treatment times would be expected to release even more DNA. In the absence of sodium (meta)periodate, no release of DNA could be detected.

Example 5: Release of Nucleic Acids from Fungi Using Periodate

Yeast are unicellular eukaryotic microorganisms, classified in the kingdom Fungi. One species of yeast, *Saccharomyces cerevisiae*, has been widely used for thousands of years and numerous applications. During the process of fermentation, *S. cerevisiae* can metabolize simple carbohydrates to $CO_2$ (carbon dioxide) and ethanol (ethyl alcohol).

The $CO_2$ is used as a leavening agent in baking and the alcohol a central component of alcoholic beverages. The biotechnology industry has recently harnessed yeast to convert sugar into ethanol, used as a biofuel. Some yeast strains have been utilized in the field of bioremediation. *S. cerevisiae* is one of the most thoroughly researched eukaryotic microorganisms and it remains an important organism for genetic and cell biology research.

While bacteria typically have cell walls comprised of peptidoglycan, fungi possess cell walls containing the glucosamine polymer, chitin. Most true fungi have a cell wall consisting of three layers: chitin, other polysaccharides (zymosan), and mannoproteins. http://en.wikipedia.org/wiki/Cell_wall-cite_note-11 In this example, *S. cerevisiae* served as a model microorganism from the kingdom Fungi for the inventors to test the efficacy of NPI (sodium (meta)periodate) for the release of nucleic acids, both DNA and RNA.

Experimental Method

Reagents BA, BB, BC and BD were prepared with and without sodium (meta)periodate (see Table 10).

A culture of *Saccharomyces cerevisiae* (Fleischmann's Bakers' yeast) was prepared by growth overnight in tryptic soy broth with 50 mM glucose at 37° C. Cells were collected from 6 mL of culture by centrifugation at 8,000 rpm for 3 minutes. The cell pellet was washed once with cold PBS by centrifugation, suspended in cold PBS, distributed into 10 tubes, centrifuged and the resultant pellets were washed again with cold water.

Each washed pellet was resuspended in 200 μL water and mixed with an equal volume of BA, BB, BC and BD reagents with or without NPI (15 mM final). The suspensions were heated at 70° C. for 20 minutes and then cooled to room temperature. Suspensions were centrifuged at 14,000 rpm for 4 minutes; the clarified supernatants were transferred to fresh tubes and the pellets were discarded.

A 10 μL portion of each supernatant was electrophoresed on a 0.8% agarose gel and stained with ethidium bromide to visualize DNA and RNA.

To the remainder of the supernatant fractions, HCl was added to a final concentration of 0.2 N. Samples were heated for 60 minutes at 60° C. 150 μL of each sample was then neutralized with 100 μL of ADA buffer, pH 8.0.

The neutralized samples (40 μL) were analyzed by HPLC and the AUC for adenine was determined.

Results and Discussion

DNA Released from *S. cerevisiae* by Treatment with Different Compositions without or with Periodate The results shown in Table 12 below demonstrate several features of the present invention.

*Saccharomyces cerevisiae*, a hardy unicellular microorganism, is unexpectedly sensitive to the release of DNA by sodium (meta)periodate. Sodium (meta)periodate in water alone at near-neutral pH (BCP) released 4-fold more DNA after 20 minutes treatment at 70° C., compared to the same heat treatment in water (BC) (Table 12).

The addition of a high concentration of SDS (1-2% final) and/or LiCl (125 mM) and/or higher pH and/or the chelator CDTA (2.5-25 mM) increased even more the amount of DNA released (Table 12). Interestingly, the amount of DNA released under the same conditions in the absence of sodium (meta)periodate was not affected by these secondary components of the novel reagents (Table 12).

Figure 4:
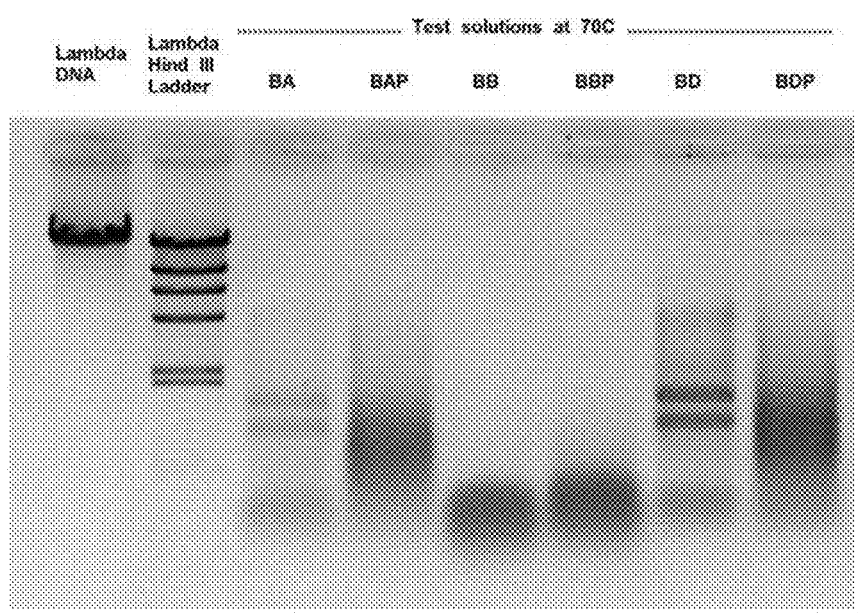
FIG. 4 is a photograph of an agarose gel showing nucleic acids released from *S. cerevisiae* using compositions of the present application.

As expected from literature reports, yeast contains a large amount of RNA compared to DNA, which can be seen by agarose gel electrophoresis (FIG. 4). Clear, intense ribosomal RNA (rRNA) bands can be seen in samples from treatment using reagents BA and BD in the absence of sodium (meta)periodate; more RNA appeared to be released when sodium (meta)periodate was added (BAP, BDP), but the RNA was partially degraded. No attempts were made in these experiments to stabilize the RNA released from *S. cerevisiae* by the treatment conditions.

Large amounts of RNA were released using BB and BBP buffered with borate, but in both cases the RNA was appreciably degraded (FIG. 4). In all cases, only small amounts of high molecular weight DNA were seen on the gel, compared to the amounts of RNA (FIG. 4).

TABLE 12

Effect of Reagents Containing Periodate on the Release of DNA from *S. cerevisiae* Using the Acid-Extraction/HPLC Method to Measure AUC for Adenine*

| Replicate | BA | BAP | BB | BBP | BC | BCP | BD | BDP |
|---|---|---|---|---|---|---|---|---|
| 1 | 71.6 | 750.5 | 425.5 | 887.6 | 136.6 | 478.4 | 92.8 | 652.9 |
| 2 | 68.4 | 622.0 | 448.3 | 732.0 | 137.3 | 557.9 | 104.2 | 660.4 |
| 3 | 71.1 | 541.8 | 488.6 | 729.7 | 128.1 | 486.4 | 111.4 | 659.1 |
| Average | 70.4 | 638.1 | 454.1 | 783.1 | 134.0 | 507.6 | 102.8 | 657.5 |
| Relative amount released | 9.0% | 81.5% | 58.0% | 100% | 17.1% | 64.8% | 13.1% | 83.9% |

*details of compositions provided in Table 10.

Conclusions

This study demonstrated that the release of both DNA and RNA from the yeast *S. cerevisiae*, a primitive eukaryotic microorganism with a sturdy cell wall, can be greatly enhanced by treatment with reagents containing sodium periodate, as compared to the same reagents without periodate. In some periodate-containing reagents, high molecular weight DNA and RNA was extracted as shown using agarose gel electrophoresis to view DNA and RNA released from the *S. cerevisiae*.

Example 6: Effect of Periodate and Heat Treatment on Release of Nucleic Acids from *B. subtilis* and *M. smegmatis* in Various Reagents In this example, the effects of temperature (room temperature, 50° C., 70° C., 80° C. and 100° C.) and sodium (meta)periodate (15 mM final) in several compositions (Table 10), was assessed using two different target microorganisms, *Bacillus subtilis* and *Mycobacterium smegmatis*. The release of nucleic acids from these microorganisms was assessed using the Acid-Extraction HPLC Method, real-time PCR and agarose gel electrophoresis.

*Bacillus subtilis* is a hardy bacterium that is commonly found in soil and vegetation; it is widely used for research laboratory studies. The cells are Gram-positive, rod-shaped and have a rigid cell wall composed of peptidoglycan (murein), a polymer of sugars and amino acids. Under adverse environmental conditions, it can form tough, protective spores that are capable of surviving extreme conditions.

Mycobacteria are rod-shaped bacteria that may be identified as acid-fast by a staining technique. Some species, found in soil, are considered benign. Other species are serious pathogens for humans and other mammals and the causative agent for pulmonary tuberculosis (TB), a devastating disease in many parts of the world. The World Health Organization (WHO) estimated the 2010 incidence of TB infection to be as high as 1,000 per 100 000 population in some African countries. Co-infection of TB and HIV is a particularly lethal combination. A growing cause for concern is the emergence of extensively drug-resistant (XDR) strains of TB, which constitute a major human health problem.

*Mycobacterium* species share a characteristic tough cell wall containing a waxy material called mycolic acids, which makes the microorganism very hydrophobic. The cell wall consists of a mycolic acid layer, a peptidoglycan layer and the polysaccharide, arabinogalactan. The property of acid-fast staining is due to the mycolic acid layer. While Gram-positive bacteria are generally sensitive to the lysozyme, no such enzyme is known that attacks the cell wall of Mycobacteria. All current methods for effectively releasing DNA from this species require some form of mechanical disruption.

The presently described method, which completely avoids complex mechanical disruption steps, was evaluated for its ability to liberate DNA from these species of microorganisms.

Experimental Methods

*B. subtilis* was grown in trypic soy broth at 37° C. overnight. An aliquot (100 L) of the overnight culture was used to inoculate 40 mL of trypic soy broth and grown at 37° C. on a shaking platform until log phase. *M. smegmatis* was grown on trypic soy agar for 3 days at 37° C. and then harvested by scraping into cold $H_2O$.

*B. subtilis* and *M. smegmatis* were each collected by centrifugation at 2,700 g for 15 minutes; the supernatant was discarded. Bacterial pellets were washed twice with cold $H_2O$ by centrifuging at 2,700 g for 15 minutes and discarding the supernatants. The washed bacterial pellets were resuspended in 15 mL of cold $H_2O$.

Three aliquots (300 µL each) of each bacterial suspension were treated directly with the Acid-Extraction HPLC Method to determine total nucleic acid content in these cells.

The remainder of each bacterial suspension was split into 1.5 mL sample aliquots and then mixed with an equal volume of one of BA, BB, BC or BD reagent (Table 10), with and without sodium (meta)periodate (30 mM in reagents, 15 mM final).

Each 3 mL aliquot was divided equally (600 µL) into 5 microcentrifuge tubes and incubated at room temperature, 50°, 70°, 80° or 100° C. for 20 minutes. The tubes were centrifuged at 14,000 rpm for 5 minutes. The clarified supernatants were transferred to fresh tubes and pellets were discarded. An aliquot (190 µL) of each supernatant was removed for direct analysis in triplicate by Acid-Extraction HPLC Method (Table 13 and 14) as follows:

Hydrochloric acid was added to supernatant fractions to a final concentration of 0.2 N. The fractions were heated at 60° C. for 60 minutes. Aliquots (150 µL) of each fraction were neutralized with 100 µL of ADA buffer, pH 8.0. The resulting samples were analyzed by HPLC and the AUC for adenine was determined.

A 350 µL sample from each of the remaining supernatant fractions was removed and incubated at 50° C. for 1 hour with proteinase K (160 µg).

Figure 5:
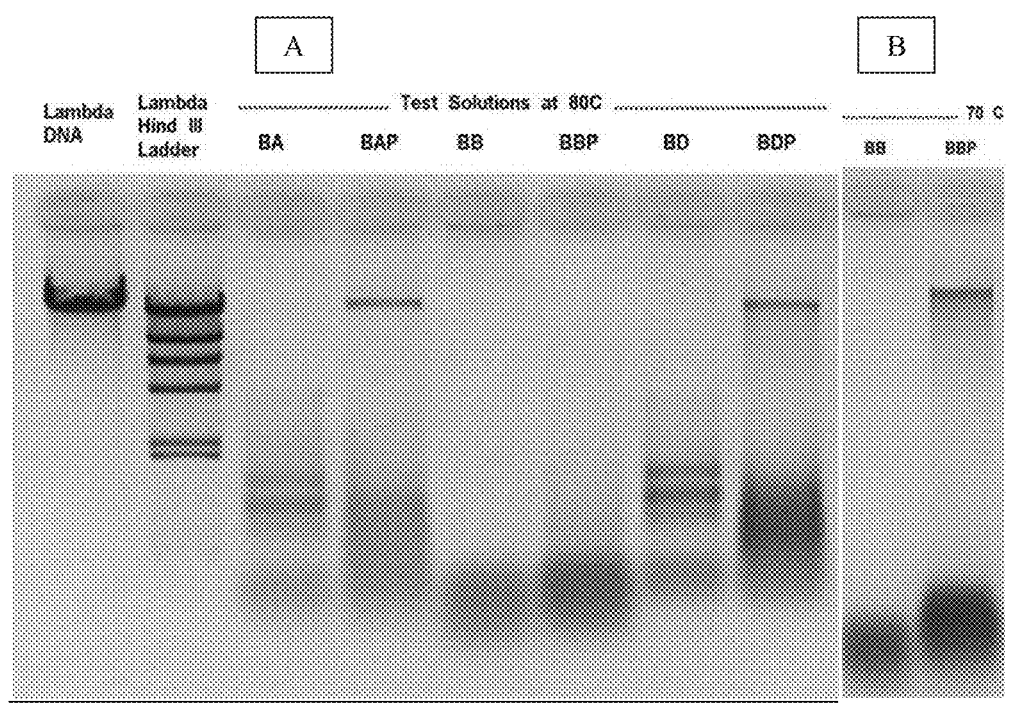
FIG. 5 is a photograph of an agarose gel showing DNA and RNA released from *Bacillus subtilis* using periodate and heating.
Figure 6:
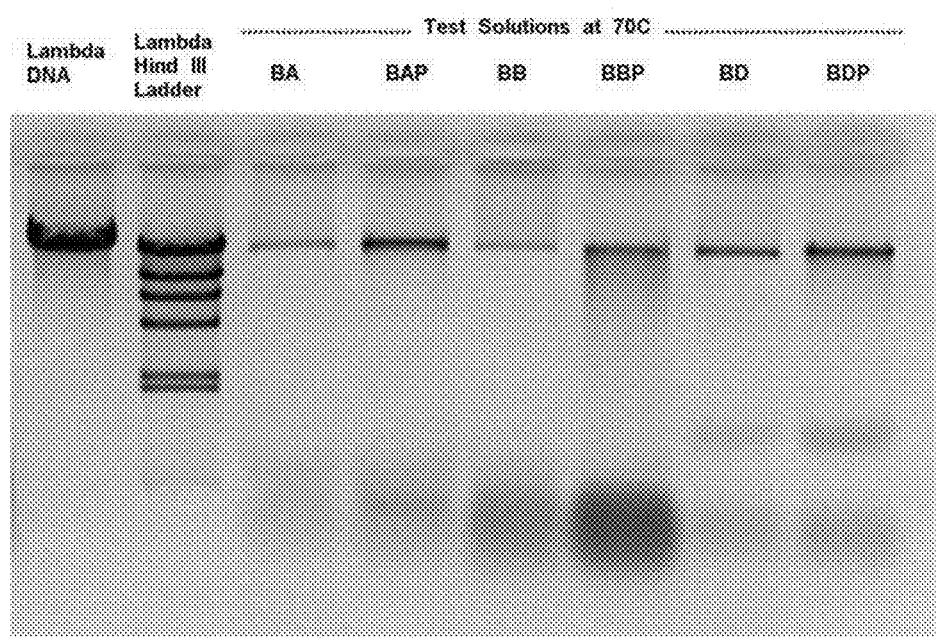
FIG. 6 is a photograph of an agarose gel showing DNA and RNA released from *Mycobacterium smegmatis* using periodate and heating.

10 µL of each treated supernatant fraction was electrophoresed on a 1.0% agarose gel at 100 V for 40 minutes with a 1 Kb*DNA ladder as a marker; the gel was stained with ethidium bromide (1 µg/µL) for 10 minutes and the DNA and RNA were visualized/photographed under UV transillumination (FIGS. 5 and 6).

Sodium chloride (0.1 M final) was added to tubes with BC and BCP chemistries. Two volumes of 95% cold ethanol was added to all tubes and then incubated at −20° C. for 30 minutes to precipitate nucleic acids. Tubes were centrifuged at 13,000 g and the pellets were carefully rinsed once with cold 70% ethanol.

The pellets were air-dried and dissolved in 90 µL of reduced TE (10 mM Tris, 0.1 mM EDTA, pH 8.0). A 2 µL portion of each dissolved pellet was added to a 25 µL PCR reaction with 'universal' bacterial 16S ribosomal DNA primers (BacrRNA173-F 5'ATTACCGCGGCTGCTGG3' and BacrRNA173-R 5'CCTACGGGAGGCAGCAG3') to estimate by quantitative real-time PCR (qPCR) the amount of DNA released from *B. subtilis* and *M. smegmatis* for each test condition (Table 15 and 16). Each PCR reaction contained 2.5 µL of 1 mg/mL bovine serum albumin (BSA), 2.5 µL of 10×PCR Buffer, 1.25 µL of 50 mM $MgCl_2$, 0.5 µL of 10 mM dNTPs, 0.5 µL of 10 pMol forward primer, 0.5 µL of 10 pMol reverse primer, 0.5 µL of 0.5 µM Syto 9, 0.2 µL of 5 U/µL Taq Polymerase, 12.3 µL of water. Highly purified DNA from *B. subtilis* and *M. smegmatis* served as a reference for PCR analysis. Negative controls included reactions in which no template DNA was added. The Ct value refers to the fractional cycle number at the point where the amplification curve crosses a threshold of detection. The Rotorgene instrument software set a threshold line and calculated the Ct values for each sample. Ct values are inversely proportional to the amount of DNA in a sample; a decrease in one Ct value corresponds to a doubling in the amount of DNA detected.

Results and Discussion

The results are shown in Tables 13, 14, 15 and 16 and in FIGS. 5 and 6.

TABLE 13

Effect of Periodate in Different Reagents on DNA Release from B. subtilis Treated at Increasing Temperatures for 20 Minutes, as Measured Using the Acid-Extraction HPLC Method

| | % Release of DNA* | | | | | | | |
|---|---|---|---|---|---|---|---|---|
| Temperature (° C.) | BA | BAP | BB | BBP | BC | BCP | BD | BDP |
| room temperature | 1.3 | 3.2 | 5.5 | 6.9 | 0 | 0 | 3.9 | 5.5 |
| 50 | 4.4 | 7.5 | 17.2 | 13.1 | 0 | 6.7 | 9.8 | 4.2 |
| 70 | 2.2 | 12.4 | 26.5 | 58.9 | 0 | 8.6 | 2.8 | 21.0 |
| 80 | 5.8 | 30.6 | 37.5 | 106.8** | 0 | 9.0 | 4.8 | 52.3 |

*The percentage of DNA released from vegetative B. subtilis is calculated from the average AUC for adenine released into the supernatant under each treatment condition, divided by the average amount of adenine acid-extracted from the pellet of untreated bacteria.
**Values above 100% indicate that the reference samples (average amount of adenine acid-extracted from the pellets of untreated bacteria) slightly underestimated the total amount of DNA present.

TABLE 14

Effect of Periodate in Different Reagents on DNA Release from M. smegmatis Treated at Increasing Temperatures for 20 Minutes, as Measured Using the Acid-Extraction HPLC Method

| Temperature | % Release of DNA* | | | | | | | |
|---|---|---|---|---|---|---|---|---|
| (° C.) | BA | BAP | BB | BBP | BC | BCP | BD | BDP |
| room temperature | 3.3 | 16.1 | 4.2 | 17.3 | 0.4 | 0.0 | 3.2 | 30.0 |
| 50 | 9.6 | 37.8 | 9.4 | 43.8 | 0.5 | 18.1 | 10.6 | 55.1 |
| 70 | 8.3 | 43.1 | 10.0 | 43.8 | 9.1 | 27.1 | 9.4 | 62.5 |
| 80 | 6.8 | 56.8 | 11.9 | 90.1 | 7.9 | 17.6 | 7.8 | 57.0 |

*The percentage of DNA released from vegetative M. smegmatis is calculated from the average AUC for adenine released into the supernatant under each treatment condition, divided by the average amount of adenine acid-extracted from the pellet of untreated bacteria.

With reference to FIG. 5, which shows DNA and RNA released from Bacillus subtilis into the supernatant by periodate and an 80° C. (A) or 70° C. (B) heating step, the intensity of high molecular weight (>23 kb) DNA bands was markedly increased by the presence of periodate in all but one case, BBP at 80° C. (panel A). The latter was likely due to an error resulting in the loss of the DNA at some point after its release from the cells, since the same sample treated at 70° C. showed a strong DNA band (panel B). Intact or substantially intact ribosomal RNA was present from treatments in all conditions, except BB and BBP.

With reference to FIG. 6, which shows DNA and RNA released from Mycobacterium smegmatis into the supernatant by periodate and a 70° C. heating step the intensity of high molecular weight (>23 kb) DNA bands was markedly increased by the presence of periodate in all cases. Compared to B. subtilis, the amount of RNA released was less and it was more extensively degraded.

TABLE 15

Quantification of DNA Released from B. subtilis into the Supernatant by Periodate and Increasing Temperature using qPCR

| | | Ct Values | | | |
|---|---|---|---|---|---|
| | | Room temperature | 50° C. | 70° C. | 80° C. |
| Test Solutions | BA | 17.0 | 17.1 | 17.2 | 16.4 |
| | BAP | 17.6 | 16.1 | 15.2 | 13.0 |
| | BB | 14.9 | 14.8 | 14.1 | 14.6 |
| | BBP | 17.3 | 17.1 | 13.7 | 13.9 |
| | BC | 22.5 | 22.2 | 20.6 | 24.4 |
| | BCP | 24.7 | 24.9 | 22.9 | 24.5 |
| | BD | 14.5 | 13.4 | 14.3 | 14.3 |
| | BDP | 14.7 | 14.3 | 11.4 | 10.2 |

TABLE 16

Quantification of DNA Released from M. smegmatis into the Supernatant by Periodate and Increasing Temperature using real-time PCR

| | | Ct Values | | | |
|---|---|---|---|---|---|
| | | Room temperature | 50° C. | 70° C. | 80° C. |
| Test Solutions | BA | 21.5 | 21.6 | 20.7 | 19.9 |
| | BAP | 19.9 | 18.5 | 17.7 | 17.3 |
| | BB | 20.2 | 20.9 | 20.7 | 20.8 |
| | BBP | 19.7 | 23.5 | 21.0 | 22.6 |
| | BC | 22.7 | 21.7 | 21.9 | 25.7 |
| | BCP | 21.0 | 21.0 | 21.9 | 25.7 |
| | BD | 21.7 | 20.8 | 19.4 | 30.6 |
| | BDP | 19.5 | 20.7 | 17.1 | 19.7 |

The results presented in Tables 15 and 16 show that periodate lowers the Ct values (i.e., extracts more DNA), from both vegetative B. subtilis and M. smegmatis treated with BA, BB, and BD reagents, but not BC reagent (water), and incubated at 50, 70 and 80° C. for 20 minutes. Importantly, the quality of the DNA released with the periodate and heat treatment is suitable for subsequent amplification and identification by real-time PCR analysis. The study was repeated using heating at 100° C. and successful DNA extraction was demonstrated; however, the qPCR results were complicated by the fact that DNA denatures at 100° C. and was not quantifiable by fluorescent dyes.

The failure of some samples to show a lower Ct value after periodate treatment, is likely due to variable or poor efficiency of the ethanol precipitation step. In these experiment, this step was necessary to remove inhibitors before qPCR could be carried out. When the same samples prior to ethanol precipitation were analyzed by agarose gel electrophoresis (FIGS. 5 and 6), clear increases in the amount of DNA released from samples treated with periodate could be seen in every case.

Conclusions

Three different methods (Acid-Extraction HPLC, Agarose Gel Electrophoresis and qPCR) have been used to demonstrate the effectiveness by which the present chemical method liberates nucleic acids from microorganisms, including those well known to be resistant to standard nucleic acid extraction methods. The present method is particularly valuable since it does not require mechanical disruption or boiling of the sample. Periodate clearly increased the amount of DNA and RNA released from both *B. subtilis* and *M. smegmatis* in a temperature-dependent manner.

Example 7: Effect of Periodate and Heat Treatment on Release of Nucleic Acids from *M. smegmatis*-Spiked Saliva Samples in Various Reagents In this example, the effects of temperature (70° C.) and sodium (meta)periodate (15 mM final), added to several compositions (Table 10), were assessed using known quantities of 'live' *Mycobacterium smegmatis* spiked into human saliva, to simulate the conditions of a complex biological specimen. The release of nucleic acids from this microorganism in a complex saliva sample was assessed using the Acid-Extraction HPLC Method and real-time PCR with *Mycobacterium smegmatis*-specific primers.

Previous examples dealt with pure cultures and washed pellets of bacteria and fungi. However, the composition of most biological specimens or samples is highly complex and contains numerous sample-specific, and potentially interfering substances, as well as host cells and microbial species. For instance, in addition to large amounts of water, saliva (and sputum) contains many other substances, such as, electrolytes, mucus, numerous enzymes, antibacterial compounds and cells, both human and microbial in origin. In particular, saliva contains large amounts of mucin, which are proteins that have polysaccharide side-chains. Given that periodates primarily attack and open sugar rings, the inventors were concerned that periodates (especially at lower concentrations found to be effective in releasing DNA from washed microbial pellets), might be consumed by reacting with the overabundance of polysaccharides present in saliva, rather than being available to attack the cell wall of bacteria/fungi of interest in the sample. This example was designed to demonstrate the effectiveness of periodate in releasing nucleic acids from microorganisms in a complex biological sample. As well, specific detection of the spiked organism (*M. smegmatis*) in the presence of human DNA and oral bacterial DNA was assessed.

Experimental Method and Materials

Six 1 mL saliva samples were collected by alternately spitting into 15 mL tubes. Immediately thereafter, one of three different buffers (1 mL) was added to each tube as follows: 2 tubes contained BA reagent, 2 tubes contained BB reagent and the remaining 2 tubes contained BD reagent (Table 10).

A suspension of approximately 109 *Mycobacterium smegmatis* was washed twice by centrifugation in 1 mL of cold PBS, pH 7.4 and then suspended in 0.5 mL PBS.

100 µL of each bacterial suspension was added to one set of tubes containing BA, BB or BD reagents; 100 µL of PBS was added to the second set of tubes. Samples were mixed briefly by vortexing. Another 100 µL of bacterial suspension (in duplicate) was subjected to the Acid-Extraction HPLC Method to accurately quantify the amount of *M. smegmatis* DNA spiked into each saliva aliquot with one of the three buffers. Using adenine standards of known concentration and the known 67.5% GC content of *M. smegmatis* DNA to convert quantity of adenine to quantity of DNA, it was determined that 100 µL of bacterial suspension contained 2366 ng of *M. smegmatis* DNA. 100% yield of DNA was not expected since extraction steps were followed by purification steps, e.g., ethanol precipitation (described below), which are not 100% efficient.

10 µL of proteinase K (89 µg/mL final) was added to each tube and the tubes were incubated at 50° C. overnight.

One 200 µL aliquot from each tube was transferred to a fresh tube and mixed with 10 µL of 300 mM sodium (meta)periodate.

A second 200 µL aliquot from each tube was transferred to a fresh tube.

All aliquots were incubated at 70° C. for 20 minutes, and then cooled at room temperature for 3 minutes.

Tris-HCl (1 M, pH 7.1) was added to each aliquot to a final concentration of 100 mM and incubated at room temperature for 15 minutes.

Potassium acetate (3 M, pH 5.5) was added to each aliquot to a final concentration of 150 mM and incubated on ice for 10 minutes.

Aliquots were centrifuged at 14,000 rpm for 3.5 minutes. The supernatants were removed and transferred to fresh tubes; the pellets were discarded.

Two volumes of room temperature 95% ethanol was added to each aliquot and incubated at room temperature for 15 minutes.

Aliquots were centrifuged at 14,000 rpm for 3.5 minutes.

Alcohol was carefully removed from each aliquot and the DNA pellets were dissolved in 50 µL TE, pH 7.5. A portion of the re-dissolved pellet was diluted 5 times and 5 µL of the diluted aliquot was added as template to a 25 µL qPCR reaction containing *M. smegmatis* gene-specific DNA primers [HP-Forward: TGCCAT-CATCAGCGAAGTAG; HP-Reverse: GCGGCTACA-GATTACGAAGC]. The expected product is a 250 bp region of the gene encoding 'hypothetical protein MSMEI_2098' of *Mycobacterium smegmatis* str. MC2 155. This primer-pair was used to estimate by quantitative PCR (qPCR) the amount of DNA released from this microorganism after 'spiking' it into saliva samples. Specific conditions are listed in Table 17. The qPCR reactions also contained 2.5 µL of 1 mg/mL bovine serum albumin (BSA), 2.5 µL of 10×PCR Buffer, 1.0 µL of 50 mM MgCl$_2$, 0.5 µL of 10 mM dNTPs as well as 0.5 µL of 10 pMol forward primer, 0.5 µL of 10 pMol reverse primer described above, 0.5 µL of 0.5 µM Syto 9, 0.2 µL of 5 U/µL Taq Polymerase, 11.85 µL of water. Highly purified DNA from *M. smegmatis* served as a reference for qPCR analysis. Negative controls included reactions in which no template DNA was added. The Ct value refers to the fractional cycle number at the point where the amplification curve crosses a software-generated threshold of detection. The Rotorgene software sets the threshold and calculates the Ct values for each sample. Ct values are inversely proportional to the amount of DNA in a sample; a decrease in one Ct value corresponds to a doubling in the amount of DNA detected.

Results and Discussion.

The results are summarized in Table 17, below:

TABLE 17

Quantification of DNA Released from *M. smegmatis*-spiked Human Saliva by Periodate and Heat Treatment using qPCR

| Test Reagents | Periodate (mM) | Saliva spiked with *M. smegmatis* | Ct value | Estimated DNA (ng/reaction) |
|---|---|---|---|---|
| BA | 0 | − | 30.66 | 0.00 |
| BA | 15 | − | 33.23 | 0.00 |
| BA | 0 | + | 21.22 | 0.00 |
| BA | 15 | + | 17.86 | 1.09 |
| BB | 0 | − | 32.67 | 0.00 |
| BB | 15 | − | 30.56 | 0.00 |
| BB | 0 | + | 21.34 | 0.07 |

TABLE 17-continued

Quantification of DNA Released from *M. smegmatis*-spiked
Human Saliva by Periodate and Heat Treatment using qPCR

| Test Reagents | Periodate (mM) | Saliva spiked with *M. smegmatis* | Ct value | Estimated DNA (ng/reaction) |
|---|---|---|---|---|
| BB | 15 | + | 15.61 | 6.43 |
| BD | 0 | − | 30.41 | 0.00 |
| BD | 15 | − | 30.99 | 0.00 |
| BD | 0 | + | 20.47 | 0.15 |
| BD | 15 | + | 14.45 | 16.23 |

The results of Table 17 show that periodate dramatically increased the amount of *M. smegmatis* DNA released from cells that were initially 'spiked' into saliva and subsequently treated with periodate-containing BB and BD reagents at 70° C. for 20 minutes. Lower Ct values are a reflection of larger amounts of *M. smegmatis* DNA. A similar but less dramatic increase in extraction efficiency was seen with BA reagent containing periodate. In the most striking case, the estimated amount of DNA increased about 100-fold, from 150 pg to 16,230 pg per reaction, in samples containing BD reagent alone compared to BD plus periodate. For samples containing BB, adding periodate also increased the DNA 100-fold, from 70 pg to 6,430 pg per reaction. For samples containing BA, adding periodate increased the DNA detected from undetectable to 1,090 pg per reaction. These experiments demonstrate that the quality of DNA released from *M. smegmatis* mixed with saliva containing periodate and other reagents and subsequently heated is suitable for PCR amplification and microorganism-specific identification by qPCR analysis using *M. smegmatis*-specific primers.

Conclusions

This example demonstrates the effectiveness by which the present chemical composition and method liberates nucleic acids from *M. smegmatis*, even when spiked into a complex biological sample. Despite the presence of protein-linked polysaccharides and other potentially interfering substances found in saliva, small concentrations of periodate were highly effective in releasing a significant proportion of nucleic acids from this very hardy microorganism. This demonstrated 100-fold increase in the release and detection of DNA from *M. smegmatis* by periodate may increase the sensitivity of detection of smear-negative, MT-positive samples, allowing earlier initiation of effective treatment regimens and thereby reduce periods of infectiousness of MDR TB cases.

Example 8: Comparing the Amount of DNA Released from *Clostridium botulinum* and *Clostridium difficile* Spores by Periodate and MagNA Pure Purification Methods as Determined by Real-Time PCR

*Clostridium* is a genus consisting of approximately 100 Gram-positive bacteria species, belonging to the *Firmicutes*, which produce hardy spores when stressed. These rod-shaped cells are ubiquitous in nature and especially prevalent in soil. *Clostridia* are motile, obligate anaerobes that are important pathogens causing human disease. There are five main species responsible for human disease, namely *C. botulinum, C. difficile, C. perfringens, C. tetani,* and *C. sordellii*.

Spores produced by *C. botulinum* are oval, subterminal endospores, commonly found in soil, and are very hard to kill. *C. botulinum* spores can survive boiling water temperature at sea level, thus many foods are canned with a pressurized boil that achieves an even higher temperature, sufficient to kill the spores. *C. botulinum* produce botulinum toxin in food and wounds, which can lead to botulism. Spores from this bacterium can be found in honey and cause infant botulism in children twelve months and younger. "Botox," a neurotoxin, is used cosmetically to paralyze facial muscles to reduce the signs of aging, as well as in numerous therapeutic applications.

Approximately 1 out of every 20 hospitalized patients will contract a hospital-acquired infection (HAI). While most types of HAIs are declining, outbreaks caused by *Clostridium difficile*, a commensal bacterium of the intestine, are a growing problem afflicting patients in hospitals and long-term healthcare facilities where antibiotics treatment is commonplace. *C. difficile* infection (CDI) is transmitted by the fecal-oral route and believed to result from gastro-intestinal dysbiosis, i.e., the disruption of the normal gut microbes or flora. Antibiotics treatment kills most bacteria in the GI tract that usually keep *C. difficile* under control. In this altered environment, *C. difficile* replicate and produce toxins that attack the lining of the intestine, causing symptoms ranging from diarrhea to life-threatening inflammation and bleeding of the lining of the colon. According to the Centers for Disease Control and Prevention (CDC), *C. difficile* is linked to the deaths of 14,000 people a year in the United States.

In healthcare environments, *C. difficile* is transmitted person to person by the fecal-oral route and outbreaks occur when humans accidentally ingest spores from common 'touch' surfaces (e.g. bed rails, door knobs, toilets, sinks). *C. difficile* spores are resistant to heat and most routine surface cleaning methods, including alcohol-based hand cleaners, and can remain viable in the environment for several months to years. An effective treatment against recurrent *C. difficile* infection is not widely available. Paradoxically, today, the primary treatment for *C. difficile* infection is the administration of more antibiotics, with about 20% of patients having recurrences within a month, and many of those have repeated attacks.

Many markets and industries are looking for efficient ways to destroy harmful spores (and bacteria), including food safety (food/meat processing plants), healthcare, soil and water sampling (environment testing), biosecurity or biodefence, animal feed testing, agriculture/plant science/industry, etc. Both clinical practice and epidemiologic studies, interested in the detection and characterization of pathogenic strains of bacteria and/or spores, need faster alternative methodologies with excellent sensitivity and specificity, as well as test-retest reliability. Today, the "gold standard" test still involves stool culture, which is a sensitive assay, but has a long turnaround time, is resource intensive, and requires experienced laboratories with tissue culture facilities. In contrast, PCR assay testing is inexpensive, has a fast turnaround time, excellent sensitivity, specificity and predictive value, assuming a sufficient quantity of DNA was extracted from the bacteria/spores of interest present in the collected biological sample.

The present inventors have surprisingly found that a common laboratory chemical, periodate, used at slightly alkaline pH and elevated temperature, can be used to rapidly and efficiently release nucleic acid from microorganisms, in both their active and dormant state. In this example, spores were prepared from cultures of *Clostridium botulinum* and *Clostridium difficile* and the efficacy of two different DNA isolation methodologies were compared, 1) the present periodate method and 2) a commercially-available MagNA™ Pure Purification Method. DNA extracted by these methods was quantified using CLIA/CLEP-approved real-time PCR (rtPCR) assay specific for each organism.

Experimental Method

[*C. botulinum* and *C. difficile* spore preparation, DNA extraction and rtPCR assay was performed in collaboration with Wadsworth Center Biodefense Laboratory, New York State Department of Health, Albany, N.Y., U.S.A.]

*C. botulinum* and *C. difficile* Spore Preparation

Frozen stock cultures of *C. botulinum* Type B and *C. difficile* were cultured on Trypticase Soy Agar with 5% Sheep's Blood and incubated anaerobically at 35° C. for 24 to 48 hours. After initial incubation, these cultures were transferred to multiple (minimum of 10) Brain Heart Infusion Agar plates and incubated anaerobically at 35° C. for up to 2 weeks. Malachite Green spore staining was performed every 3 to 4 days to monitor sporulation of bacteria in vitro. When the malachite green stains showed almost complete sporulation of organisms, the spores were harvested into 5.0 mL of PBS (pH 7.4) and stored at room temperature until use.

Determination of Spore Concentration

Each spore stock suspension of *C. botulinum* and *C. difficile* were diluted in PBS to $10^{-2}$. An aliquot (10 µL) of each of these final dilutions were loaded into each clean well of a 2-chamber hemocytometer slide. Hemocytometer chambers were observed at 40× magnification without oil for spore counting. Spores were visualized as round or oval black cells on the light field grid of the hemocytometer. *C. botulinum*, Limit of Detection (LOD)=30 spores/reaction; *C. difficile*, LOD=20 spores/reaction.

Extraction of DNA from Spores Using Periodate Method
1. To 350 µL spore stock suspension of *C. botulinum* and *C. difficile* (above), add 350 µL BD2 buffer (2% SDS, 12.5 mM CDTA, 250 mM LiCl, 50 mM glycine, pH 10.5).
2. Vortex to mix.
3. Remove 100 µL for culture.
4. Add 50 µL of 300 mM sodium (meta)periodate or NPI stock (final concentration 30 mM), vortex to mix.
5. Incubate at 70° C. in a water bath for 20 minutes.
6. Cool samples at room temperature for 2 minutes.
7. Remove 100 µL for culture.
8. Add 20 µL of 1M Tris pH 7 buffer (final concentration 50 mM).
9. Incubate at room temperature for 10 minutes.
10. Add 20 µL of 3M potassium acetate pH 5.5 (final concentration 150 mM).
11. Incubate on ice for 10 minutes.
12. Centrifuge at 13,000 rpm for 5 minutes.
13. Transfer supernatant to a clean, labeled tube. Discard pellet.
14. Add 800 µL room temperature 95% ethanol.
15. Invert 20 times to mix.
16. Incubate samples at room temperature for 15 minutes to precipitate DNA.
17. Centrifuge at 15,000 rpm for 2 minutes to pellet DNA.
18. Gently remove and discard supernatant taking care not to disturb the pellet.
19. Dissolve pellet in 100 µL TE.
20. Vortex briefly to fully resuspend DNA.
21. Run CLIA/CLEP-approved rtPCR assay specific for each organism.

Extraction of DNA from Spores Using Roche MagNA™ Pure DNA Isolation Kit
1. Prepare 10 aliquots of 200 µL *C. botulinum* and *C. difficile* spore suspensions at each desired concentration (total 30 tubes).
2. Lysis buffer was prepared for each sample by combining 38 µL proteinase K with 262 µL Bacterial Lysis Buffer from MagNA Pure LC DNA Isolation Kit III (Bacteria, Fungi) (Cat. No. 03264785001, Roche).
3. 300 µL of Lysis buffer was added to each 200 µL spore suspension.
4. Vortex.
5. Incubate at 65° C. for 20 minutes.
6. Incubate at 95° C. for 10 minutes.
7. Samples were allowed to cool at room temperature.
8. When cool, centrifuge briefly to remove aerosols.
9. Transfer 500 µL of each sample into Roche MagNA Pure Compact sample tubes.
10. Place sample tubes on Roche MagNA Pure Compact instrument.
11. Follow on screen instructions using the DNA Blood External Lysis protocol: Sample volume: 500 µL; Elution volume: 100 µL.

Real-Time PCR for *C. botulinum* Type B and *C. difficile*

All rtPCR assays were performed on an ABI 7500 instrument. DNA isolated from each extraction was analyzed in singlicate for *C. botulinum* Type B and *C. difficile* using a CLIA/CLEP-approved rtPCR assay (Wroblewski et al., 2009) specific for each organism.

Results and Discussion

Figures 7, 8:
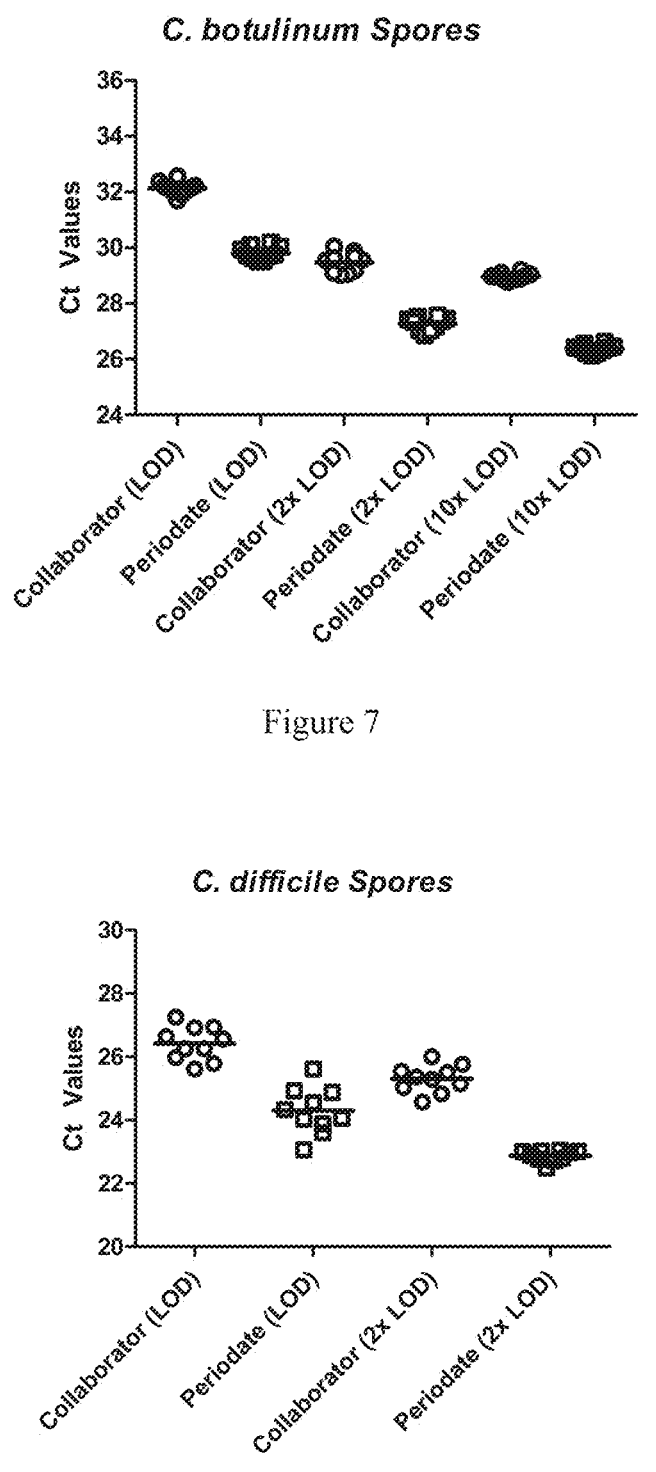

While mechanical bead beating of biological samples or cultures of bacteria/spores can be fairly effective in breaking open microbes, it does create aerosols which increase the chance of spreading infectious agents and putting the health of laboratory personnel at risk. Hence, it is highly desirable to develop non-mechanical, chemical methods to release total nucleic acid from tough microbes and their spores. This example demonstrates that the present "Periodate" method, a fast, inexpensive, easy chemical treatment, is significantly more effective (8-fold increase in DNA) at isolating DNA from both *C. botulinum* spores (FIG. 7) and *C. difficile* spores (FIG. 8) than a commercially-available DNA isolation kit ("Collaborator" method) and very costly automated system from Roche. The MagNA™ Pure kit ("Collaborator", FIGS. 7 and 8) utilizes a lysis buffer plus magnetic glass particles, while the present periodate method ("Periodate", FIGS. 1 A and 1B) does not require magnetic beads or a complex automated system with magnetic-handling capabilities to isolate DNA even from hardy spores.

CLIA/CLEP-approved rtPCR assays indicated an increased sensitivity of detection ($\Delta 3$ $C_t$ values) of DNA from both *C. botulinum* and *C. difficile* spores using the "Periodate" method, compared to the "Collaborator" method, i.e., the periodate-treated samples results in consistently lower Ct values at each LOD in rtPCR. The improved extraction of microbial DNA using the periodate method should translate into enhanced sensitivity of detection in biological samples assessed with other CLIA/CLEP-approved rtPCR assays.

Example 9: Comparing the Amount of DNA Released from Tuberculosis-Positive Clinical Sputum Samples by Periodate Method Vs. Conventional Bead Beating as Determined by Real-Time PCR Specific for *M. tuberculosis*

This example provides a side-by-side comparison of the clinical evaluation of TB-positive sputum samples (kindly donated by FIND, see below) purified by two methods. Specifically, the impact of two distinct DNA isolation methods, 1) the "Standard of Care" and 2) the "Periodate Method" were compared on the sensitivity of a CLIA/CLEP-approved rtPCR assay targeting the RD4 *Mycobacterium tuberculosis* complex (MTBC) region of difference (RD) (Halse et al., 2011).

In contrast to the "Periodate Method", the "Standard of Care" method includes bead beating, a mechanical method, to break open bacteria in sputum samples. While mechanical bead beating can be effective at breaking open organisms, it does create dangerous aerosols in the laboratory environment. Hence, it is highly desirable to develop an effective, non-mechanical, chemical method to safely release DNA from *Mycobacterium tuberculosis*, without negatively impacting the clinical sensitivity of the diagnostic test.

Experimental Methods

Confirmation of Viability of *Mycobacterium tuberculosis*-Positive Sputum Samples For the present example, raw sputum samples from TB-positive patients were kindly donated by the Foundation for Innovative Diagnostics (FIND) Tuberculosis Specimen Bank. Duplicate 0.5 mL aliquots were provided from 30 patient samples and stored frozen. Using culture and smear analysis, FIND categorized these 30 samples as 'Smear+, Culture+ (high)', 'Smearl+, Culture+ (mid)' or 'Smear−, Culture+ (low)' TB-positive.

Aliquots were shipped frozen to Wadsworth Center Mycobacteriology Laboratory (New York State Department of Health, Albany, N.Y., U.S.A.), a CLIA/CLEP-approved Clinical Laboratory for further analysis.

Upon arrival at Wadsworth, aliquots from 30 donors were thawed on ice and the viability of *Mycobacterium* in these 10 'high', 10 'mid', and 10 'low' TB aliquots was confirmed with culture and smear microscopy.

Extraction of DNA from TB-Positive Sputum Using Periodate Method 1. 0.5 mL BD2 buffer (2% SDS, 12.5 mM CDTA, 250 mM LiCl, 50 mM glycine, pH 10.5) was added to each 0.5 mL sputum aliquot; vortexed to mix.
2. Added Proteinase K (400 µg) and incubated at 50° C. in a water bath for 2 hours.
3. Transferred 0.4 mL to a fresh tube and added NPI (final concentration 30 mM), vortex to mix.
4. Incubated at 70° C. in a water bath for 20 minutes.
5. Cooled samples at room temperature for 2 minutes.
6. Added 1M Tris buffer (pH 7) buffer to a final concentration of 50 mM.
7. Incubated at room temperature for 10 minutes.
8. Added 3M potassium acetate (pH 5.5) to a final concentration of 150 mM.
9. Incubated on ice for 10 minutes.
10. Centrifuged at 13,000 rpm for 5 minutes.
11. Transferred supernatant to a clean, labeled tube. Discarded pellet.
12. Added 2 volumes of room temperature 95% ethanol.
13. Inverted 20 times to mix.
14. Incubated samples at room temperature for 10 minutes to precipitate DNA.
15. Centrifuged at 15,000 rpm for 2 minutes to pellet DNA.
16. Gently removed and discarded supernatant taking care not to disturb the pellet.
17. Dissolved pellet in 200 µL TE.
18. Vortexed briefly to fully resuspend DNA.

Extraction of DNA from TB-Positive Sputum Using "Standard of Care"

1. 0.5 mL 3.5% NaOH was added to each 0.5 mL sputum aliquot; vortexed to mix.
2. Incubated at room temperature for 15 minutes.
3. Added sterile phosphate-buffered saline (PBS) to bring volume to 10 mL.
4. Centrifuged at 5,000 rpm for 20 minutes to pellet bacteria. Discarded the supernatant.
5. Resuspended pellet in 0.5 mL sterile PBS.
6. Set aside 300 µL of resuspended bacteria for culture.
7. To remaining 200 µL of resuspended bacteria, added 200 mg of 105-150 micron glass beads.
8. Bead beat for 2 cycles of 1 minute, followed by 1 minute on ice using a Mini-BeadBeater (BioSpec Products).

Real-Time PCR for *M. tuberculosis* and Pyrosequencing for Antibiotic Resistance Duplicate reactions of 5 µL 'neat' DNA and 5 µL diluted (1:10) DNA from each purified sputum sample were amplified on an ABI 7500 real-time PCR instrument using a CLIA/CLEP-approved rtPCR assay targeting the RD4 *Mycobacterium tuberculosis* complex (MTBC) region of difference (RD) (Halse et al., 2011). Threshold cycle (Ct) values less than 37 were reported as positive, and samples with values greater than 37 were retested; if the results were the same, the result was reported as positive, and if they were not, they were reported as inconclusive.

Results and Discussion

Compared to the conventional bead beating method ("Standard of Care"), the present chemical "Periodate Method" clearly leads to increased sensitivity of *M. tuberculosis*-specific detection, in particular, for sputum samples categorized as 'low' and 'mid' TB-positive by culture and smear microscopy. In this example, not until DNA extracted using the "Standard of Care" method is diluted 10-fold can *M. tuberculosis* be detected in 'mid' and 'high' TB-positive sputum samples (Table 18); whereas 87% of 'low' TB-burden sputum samples were detected as positive following DNA isolation utilizing the "Periodate Method" (Table 18).

TABLE 18

Percentage of Sputum Samples Detected TB-Positive Following DNA Extraction using 2 Different Methods

| Extraction Method | % Detected LOW* $(n = 8)$ | % Detected Mid $(n = 10)$ | % Detected High $(n = 10)$ |
|---|---|---|---|
| Standard of Care (neat) | 12 | 0 | 0 |
| Standard of Care (1:10) | 25 | 70 | 100 |
| Periodate Method | 87 | 100 | 100 |

Figure 9:
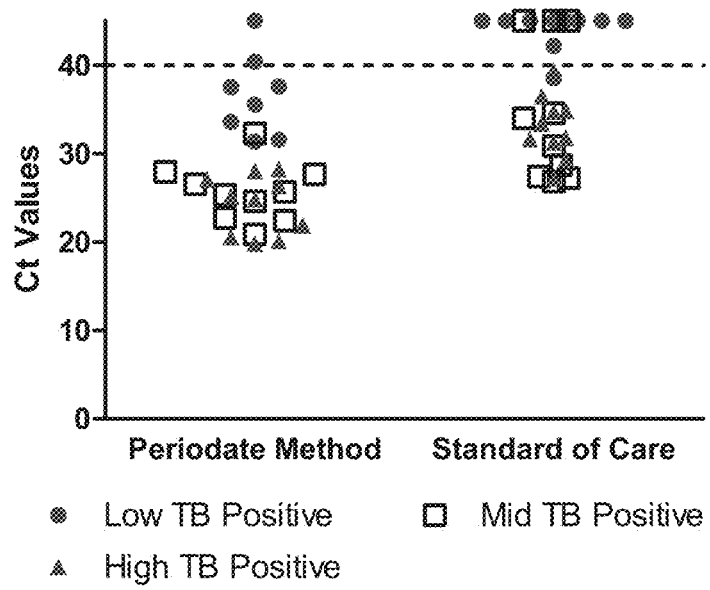
FIG. 9 graphically depicts a comparison of "Periodate" method and the "Standard of Care" method sensitivity of rtPCR.
Figure 10:
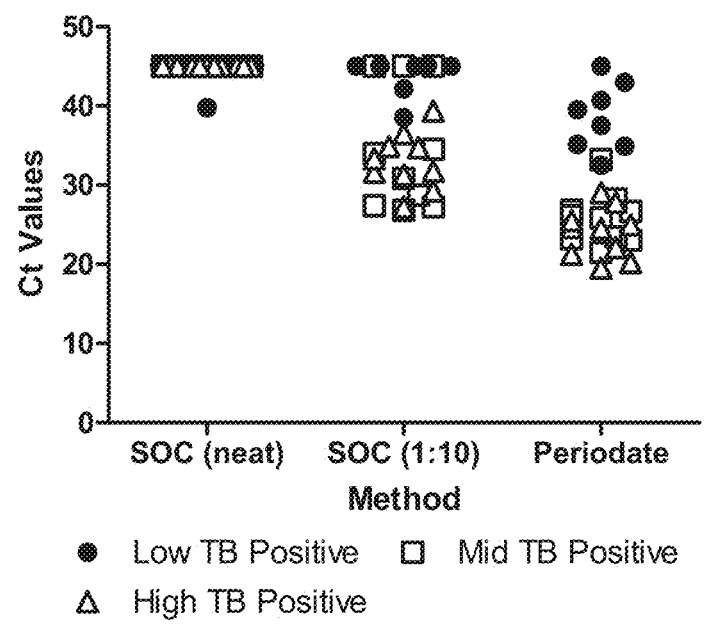
FIG. 10 graphically depicts rtPCR Analysis of Low, Mid and High TB Burdened Sputum Samples.
Figure 11:
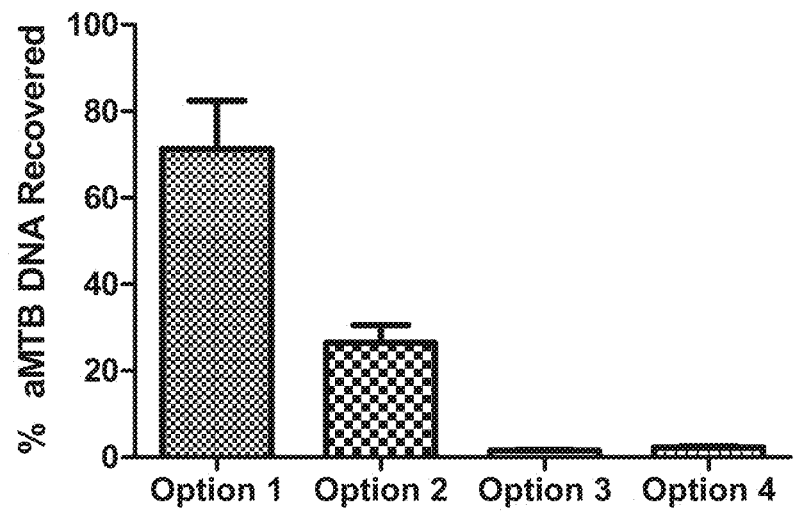
FIG. 11 graphically depicts percentage of aMTB DNA recovered from saliva samples using different extraction methodologies.

*2 data points excluded from Low samples-not detected following any extraction method or by culture FIG. 9 illustrates the significantly improved limit of detection of *M. tuberculosis* in all TB-positive sputum samples extracted using the "Periodate Method", compared to the "Standard of Care" or SOC. For example, the $C_t$ values for 'low' TB-positive sputum ranged from 31.4-45.0 for the "Periodate Method", compared to 38.5-45.0 for SOC; the Ct values for 'mid' TB-positive sputum ranged from 20.9-32.3 for the "Periodate Method", compared to 26.8-45.0 for SOC; the $C_t$ values for 'high' TB-positive sputum ranged from 19.8-28.3 for the "Periodate Method", compared to 27-2-39.3 for SOC. FIG. 10 shows the data of FIG. 9 arranged by DNA extraction method. The Ct values are consistently lower, for all TB burden levels, when the DNA was extracted using the periodate method of the present invention. This lower limit of detected, afforded by improved DNA extraction, helps ensure an accurate diagnosis of *M. tuberculosis* from patient sputum samples.

Example 10: Periodate-Based Method Releases Significantly More *Mycobacterium tuberculosis* DNA than does Qiagen Purification The resurgence of tuberculosis in developed, as well as developing, countries since 1980 has been associated with the HIV epidemic, the emergence of drug-resistant strains, and increases in emigration from regions with high rates of disease endemicity (Corbett et al., 2003). Tuberculosis is one of the most common causes of morbidity and the most common cause of death in HIV-positive adults living in less-developed countries, yet it is a preventable and treatable disease. The rapid detection of *M. tuberculosis* is essential for disease management due to the high risk of transmission from person to person. The US Centers for Disease Control and Prevention (CDC) recommends that clinical specimens received be analyze simultaneously by culture, acid-fast bacillus (AFB) staining, and nucleic acid amplification (NAA) protocols (Diagnostic Standards and Classifications of Tuberculosis in Adults and Children; American Thoracic Society and CDC, 2000). While culture is still the "gold standard" for final determination, it may take up to two to 8 weeks. Staining for AFB is rapid, but has a low sensitivity and a low specificity, since it does not distinguish non-tuberculosis mycobacteria (NTM) from members of the *Mycobacterium tuberculosis* complex (MTBC). Hence, rapid identification, which is essential to control the spread of tuberculosis, relies increasingly upon nucleic acid extraction and molecular diagnostic tests.

MTBC members differ in virulence attributes, drug resistance patterns, and host preferences. The rapid differentiation of these species to determine zoonotic or human sources of tuberculosis disease or to direct treatment can benefit both public health and patient management. Halse et al. (2010; 2011) developed a real-time PCR assay for differentiation of the closely-related organisms, *M. tuberculosis, M. bovis, M. bovis* BCG, *M. africanum, M. microti*, and *M. canettii*. The presence or absence of regions of difference (RD) between the genomes of members of the MTBC allowed for the design of an inexpensive, rapid, single-tube, five-plex real-time PCR (rtPCR) assay to differentiate these species in clinical specimens.

Upstream of such rtPCR assays; however, it is critical the clinical specimen is treated in such a way as to recover the maximum amount of DNA possible. Historically, quantitative studies have shown that there must be 5,000 to 10,000 bacilli per milliliter of specimen to allow detection of bacteria in stained smears (Hobby et al., 1973). In contrast, 10 to 100 organisms are needed for a positive culture (Yeager et al., 1967). Molecular detection of *Mycobacterium* in a whole specimen containing as few as 10 bacilli represents a real challenge to diagnostic assays, especially when the assay input volume is a small fraction of the total specimen. In contrast to culture and staining smears, molecular methods detect DNA from both live and dead or dying bacilli in specimens from patients undergoing treatment, allowing the identification of MTBC organisms prior to and during treatment.

There clearly exists a demand for the development of superior extraction methodologies which facilitate rapid recovery of all or the majority of the DNA from tough microbes in patient specimens. Improved DNA extraction from complex specimens, like sputum, translates directly into increased sensitivity of diagnostic (Dx)/DNA-based assays for tuberculosis, and other diseases, and ultimately faster treatment of the patient with appropriate drug therapy. This need is further compounded by the emergence of multi-drug-resistant tuberculosis (MDR-TB) and extensively drug-resistant tuberculosis (XDR-TB) in several countries, as well as the recent epidemic of rapidly fatal HIV-associated tuberculosis in South Africa (Ghandi et al., 2006; Raviglione 2006). As a result of poor control practices, some countries are now facing one of the worst possible scenarios in TB control: the lethal combination of HIV infection and highly drug-resistant TB (Raviglione 2006).

Experimental Methods

Preparation of *Mycobacterium tuberculosis*-Spiked Biological Samples

To simulate tuberculosis-positive sputum, saliva samples from healthy donors were spiked with attenuated *M. tuberculosis* (aMTB) at $5 \times 10^6$ colony forming units/mL (cfu/mL).

Extraction of DNA from *M. tuberculosis*-positive Saliva using the Periodate Method ["DNA Genotek Optimal Method" or "Option 1"]

1. Mixed an equal volume of saliva spiked-aMTB with BD2 buffer (2% SDS, 12.5 mM CDTA, 250 mM LiCl, 50 mM glycine, pH 10.5).
2. Incubated at room temperature for 15 minutes.
3. Centrifuged at 5,000 rpm for 20 minutes. Discarded the supernatant.
4. Resuspended pellet in 50% BD2 buffer.
5. Added NPI to a final concentration of 30 mM, vortex to mix
6. Incubated at 70° C. in a water bath for 20 minutes
7. Cooled samples at room temperature for 2 minutes
8. Added 1M Tris buffer (pH 7) to a final concentration of 50 mM
9. Incubated at room temperature for 10 minutes
10. Added 3M potassium acetate (pH 5.5) to a final concentration of 150 mM
11. Incubated on ice for 10 minutes
12. Centrifuged at 13,000 rpm for 5 minutes
13. Transferred supernatant to a clean, labeled tube. Discarded pellet.
14. Added 800 µL room temperature 95% ethanol
15. Inverted 20 times to mix
16. Incubated samples at room temperature for 15 minutes to precipitate DNA
17. Centrifuged at 15,000 rpm for 2 minutes to pellet DNA
18. Gently removed and discarded supernatant taking care not to disturb the pellet
19. Dissolved pellet in 100 µL TE
20. Vortexed briefly to fully resuspend DNA Extraction of DNA from *M. tuberculosis*-Positive Saliva Using the Periodate Method Followed by Qiagen Purification ["Option 2"]

1. Mixed an equal volume of saliva spiked-aMTB with BD2 buffer (2% SDS, 12.5 mM CDTA, 250 mM LiCl, 50 mM glycine, pH 10.5).
2. Incubated at room temperature for 15 minutes.
3. Centrifuged at 5,000 rpm for 20 minutes. Discarded the supernatant.
4. Resuspended pellet in 50% BD2 buffer.

5. Added NPI to a final concentration of 30 mM, vortex to mix
6. Incubated at 70° C. in a water bath for 20 minutes
7. Cooled samples at room temperature for 2 minutes
8. Added 1M Tris buffer (pH 7) to a final concentration of 50 mM
9. Incubated at room temperature for 10 minutes
10. Added an equal volume of Qiagen AL buffer
11. Followed Qiagen QIAMP procedure for Qiagen QIAamp DNA Mini Kit (Cat. No. 51304)

Figure 12:
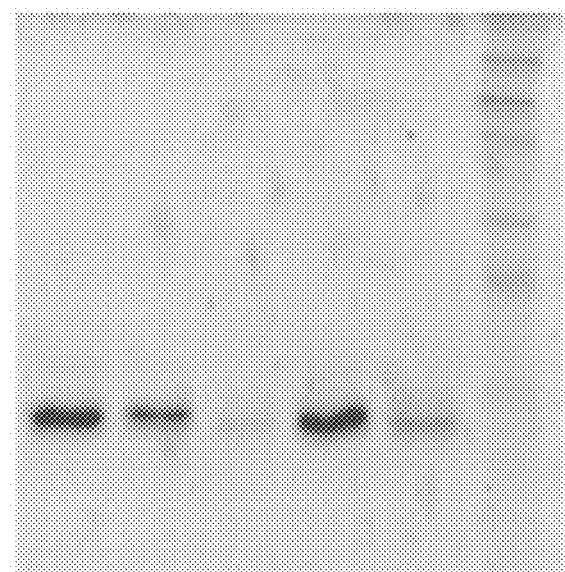
FIG. 12 is a photograph of an SDS-PAGE of pure pancreatic ribonuclease A treated with periodate.

Extraction of DNA from *M. tuberculosis*-Positive Saliva Using BD2 Buffer and Qiagen Purification ["Option 3"]
1. Mixed an equal volume of saliva spiked-aMTB with BD2 buffer (2% SDS, 12.5 mM CDTA, 250 mM LiCl, 50 mM glycine, pH 10.5).
2. Incubated at room temperature for 15 minutes.
3. Centrifuged at 5,000 rpm for 20 minutes. Discarded the supernatant.
4. Resuspended pellet in 50% BD2 buffer.
5. Added an equal volume of Qiagen AL buffer
6. Followed Qiagen QIAMP procedure for Qiagen QIAamp DNA Mini Kit (Cat. No. 51304)

Extraction of DNA from *M. tuberculosis*-Positive Saliva Using Standard Sodium Hydroxide/NALC Method and Qiagen Purification ["Standard Qiagen Method" or "Option 4"]

1. Freshly prepared and autoclaved 4% solution of sodium hydroxide (NaOH).
2. Freshly prepared and autoclaved 2.9% sodium citrate solution.
3. Prior to use, mixed equal volumes of NaOH and sodium citrate solution.
4. Added N-acetyl-L-cysteine (NALC) powder to achieve a final concentration of 0.5%. Mixed well and used the same day.
5. Mixed an equal volume of saliva spiked-aMTB with NaOH/NALC/citrate solution.
6. Incubated at room temperature for 15 minutes.
7. Added sterile PBS to bring the total volume to 50 mL.
8. Centrifuged at 5,000 rpm for 20 minutes. Discard the supernatant.
9. Resuspended pellet in PBS.
10. Added an equal volume of Qiagen AL buffer
11. Followed Qiagen QIAMP procedure for Qiagen QIAamp DNA Mini Kit (Cat. No. 51304)

rtPCR Conditions

In this example, DNA isolated from saliva spiked-aMTB samples (Options 1-4, above) was subjected to an rtPCR assay specific for *Mycobacterium*, the RD4 Taqman Real-time PCR assay. Primers for RD4 are as follows: RD4-forward 5'-CCA CGA CTA TGA CTA GGA CAG CAA-3' and RD4-reverse 5'-AAG AAC TAT CAA TCG GGC AAG ATC-3' (Halse et al. (2011)).

FIG. 11 illustrates the percentage of aMTB DNA recovered by molecular testing based on genome equivalents (GE) calculated (recovered GE/input GE*100).

Results and Conclusions

Recently-developed molecular assays provide reliable results that aid with the initial management of patients with suspected tuberculosis, prior to the availability of results for cultured material, and provide the ability to predict antibiotic resistance in *Mycobacterium tuberculosis*-positive specimens in as little as 1-2 days from the collection of clinical specimens. However, tuberculosis diagnostics and PCR-based systems in general require an efficient isolation and purification procedure for DNA, which is further complicated by the physical peculiarity and lack of homogeneity of sputum, as well as by the high lipid content of the mycobacterial cell wall. Thus, all the available techniques for mycobacterial DNA extraction require manipulation steps, which result in an unpredictable loss of starting material which can lead to false-negative diagnoses.

The present example compared multiple DNA isolation and processing methodologies for biological specimens. Specifically, tuberculosis-positive sputum was simulated by spiking saliva samples from healthy donors with aMTB. Conventional NaOH/NALC decontamination of specimens, followed by DNA extraction with a commercially-available Qiagen QIAamp DNA Mini Kit (Option 4), resulted in recovery of only 2.2% of aMTB DNA. In contrast, the present periodate method (Option 1) led to the remarkable recovery of 71.3% of aMTB DNA; a 70% increase in recovery compared to Option 4. Option 3 demonstrates that the initial incubation of the specimen with BD2 buffer was not responsible for the dramatic result of Option 1, as BD2 buffer followed by Qiagen extraction recovered 1.6% of the original spiked amount of aMTB. When periodate treated specimens were extracted with Qiagen's kit (Option 2), only 26.4% of aMTB DNA was recovered; equivalent to a 24% increase in DNA recovery compared to conventional NaOH/NACL/Qiagen kit (Option 4).

The periodate method efficiently isolated the majority of DNA from *Mycobacterium tuberculosis*-spiked specimens and, consequently can be used to significantly enhance the already well known benefits of diagnostic/molecular assays, i.e., high level of specificity and sensitivity, short turnaround time, and cost-effectiveness. These improvements allow healthcare systems to save up to 8 weeks of time to differentiate species of the MTBC by culture, provide information to achieve appropriate, rapid drug therapy with minimal side effects, as well as early insight into TB transmission.

Example 11: Selective Degradation of Protein by Periodate

Periodate is commonly used in solution to open saccharide rings between vicinal diols, allowing the selective labeling of the 3'-terminus of RNA. Surprisingly, the inventors have determined that periodate is also very effective at "killing" or neutralizing the activity of specific enzymes, such as pancreatic ribonuclease A (RNase A) and that it also degrades certain other proteins.

In this example, RNase A, a pancreatic ribonuclease that cleaves single-stranded RNA, was shown to be a target for periodate. The enzymatic activity of RNase was assessed by monitoring its ability to degrade an RNA substrate, RNA purified from HeLa cells. If the enzymatic activity of RNase were negatively impacted by periodate, then HeLa cell ribosomal RNA would not be degraded substantially as assessed by agarose gel electrophoresis.

Experimental Method and Materials

Treatment of Pure Pancreatic Ribonuclease a with Periodate

1. Pure Pancreatic Ribonuclease A (Sigma) (0.1-0.2 μg/μL) was added to a buffer (1% SDS, 25 mM Li-CDTA, 125 mM LiCl, 25 mM glycine, pH 10.5), with or without 15 mM periodate.
2. The mixture was heated at 70° C. for 15 minutes.
3. 10 μL of the mixture was loaded onto a 10% SDS-PAGE gel and run at 160 volts for 60 minutes.

4. The SDS-PAGE gel was stained with hot Coomassie blue for 30 minutes, then destained for 2 h at room temperature, and photographed under visible light (FIG. 12).

Treatment of *Mycobacterium smegmatis* Lysate with Periodate

Figure 13:
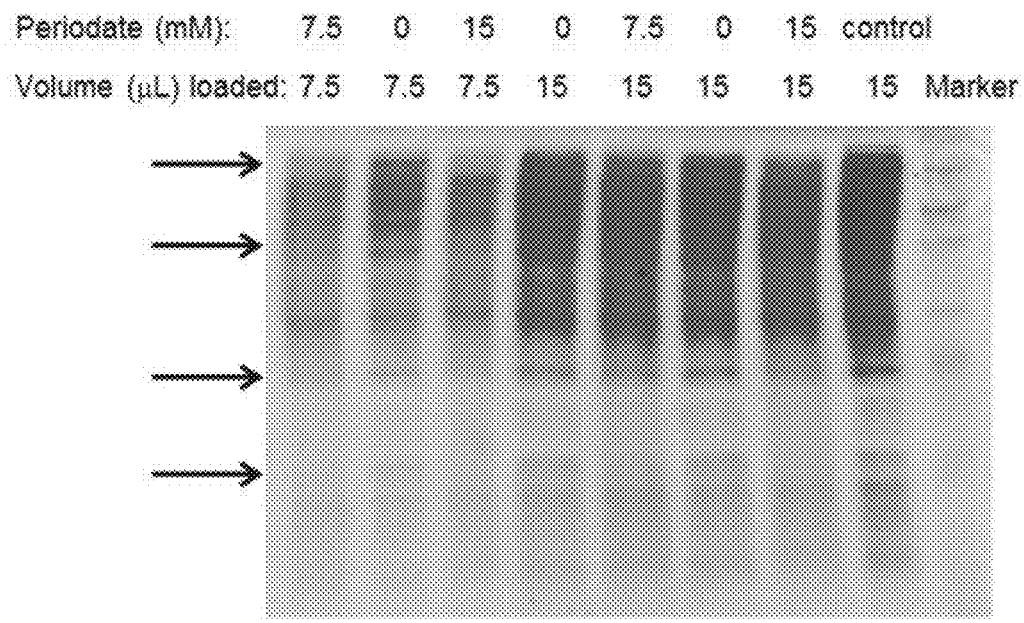
FIG. 13 is a photograph of an SDS-PAGE of *M. smegmatis* lysate treated with periodate.

1. A washed pellet was prepared from a suspension of plate-grown *Mycobacterium smegmatis*.
2. Bead-beating was performed in a Mini-BeadBeater-16 (BioSpec) according to the manufacturer's instructions. In brief, the washed bacterial pellet was suspended in 1000 µL of phosphate-buffered saline (PBS) and transferred to a screw-cap polypropylene microcentrifuge tube containing approximately 100 µL of 100 µm glass beads (Polyscience).
3. The tube was secured to the instrument and vigorous agitation was performed in two 1-minute cycles (3,450 oscillations/minute). The sample was cooled on ice for 1 minute between cycles.
4. The suspension was transferred to a 1.5 mL microcentrifuge tube and unbroken cells and debris were removed by centrifugation 5 minutes at 14,000 rpm, in a microcentrifuge.
5. The supernatant was removed and split equally between two 1.5 mL microcentrifuge tubes. One fraction was diluted with an equal volume of PBS (control, see FIG. 13). The second fraction was mixed with an equal volume of buffer (1% SDS, 25 mM Li-CDTA, 125 mM LiCl, 25 mM glycine, pH 10.5), split into 3 portions and periodate was added, to a final concentration of 0, 7.5 mM or 15 mM.
6. The tubes were heated at 70° C. for 15 minutes. The control sample was not heated.
7. 7.5 or 15 µL of the mixture was loaded on a 10% SDS-PAGE gel, and run at 160 volts for 60 minutes.
8. SDS-PAGE gel was stained with hot Coomassie blue for 30 minutes and then destained for 2 h at room temperature, and photographed (FIG. 13).

Purified HeLa Nucleic Acid Treated with Pancreatic Ribonuclease a and Periodate

Figure 14:
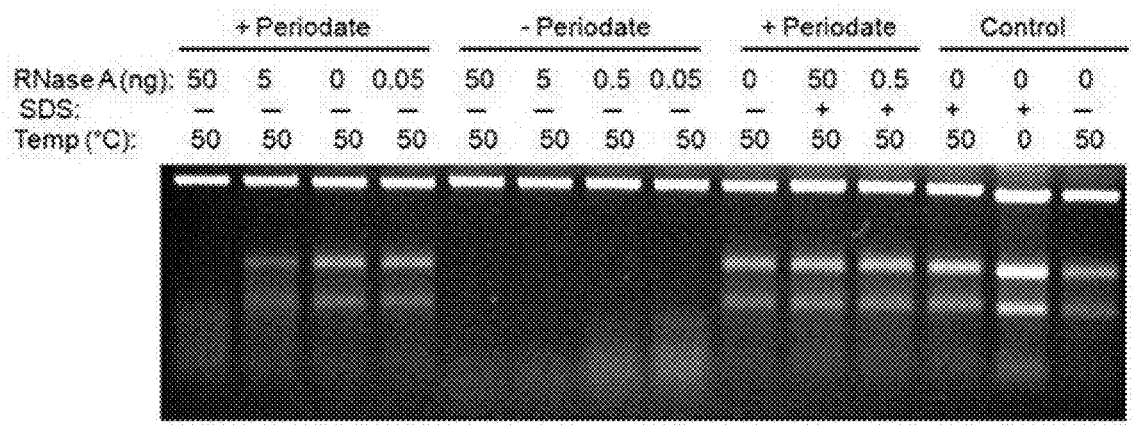
FIG. 14 is a photograph of an agarose gel electrophoresis showing inhibition of RNase A by pre-treatment with periodate.

1. A solution of pure pancreatic ribonuclease A (Sigma) (RNase A) was prepared at 10 µg/mL in 50 mM glycine, pH 10.5.
2. The solution was divided equally between two tubes and one of the aliquots was treated with 15 mM periodate.
3. Both tubes were incubated at 70° C. for 15 minutes.
4. The treated RNase A tube was diluted 200-1000 fold in 50 mM ADA buffer, pH 6.5.
5. The diluted RNase A was incubated with HeLa nucleic acid (DNA and RNA) for 20 minutes at 50° C.
6. The reaction was 'stopped' with the addition of SDS to 0.5%.
7. The integrity of the treated HeLa RNA was analyzed using 1.0% agarose gel electrophoresis (FIG. 14).

Results and Conclusions

FIG. 12 shows the surprising result that the quantity of full-length purified RNase protein decreased after a brief incubation with periodate; degradation products (smaller protein fragments) were not observed in the gel. Also, careful inspection of FIG. 13 shows the selective loss of certain (unknown) protein bands in a cell-free lysate of *M. smegmatis* after incubation with periodate. In the presence of increasing concentrations (7.5 and 15 mM) of periodate, some protein bands selectively decreased or disappeared altogether from the gel, indicating that periodate has multiple protein targets As demonstrated by the data shown in FIG. 14, ribosomal RNA was no longer degraded by RNase A if RNase A was pre-incubated with periodate for a brief period of time before contact with RNA. Addition of a relatively large amount of RNase A (50 ng) was needed to detect a small amount of residual active RNase that failed to be inactivated by periodate. Hence, in addition to its effects on total cellular proteins, periodate can target and inhibit the enzymatic action of specific degradative enzymes.

Example 12: Periodate Treatment Eliminates Viability of *Bacillus anthracis*, *Clostridium Botulinum*, and *Clostridium difficile* Spores Anthrax is an acute, often lethal, disease caused by the rod-shaped, gram-positive, aerobic bacterium *Bacillus anthracis* that normally rests in endospore form in the soil. Like *C. botulinum* and *C. difficile*, *B. anthracis* can form dormant endospores, which are very hard to eradicate, surviving harsh conditions for decades or even centuries. When spores are inhaled, ingested, or come into contact with a skin lesion on a host, they may become reactivated and multiply rapidly. The hardiness of anthrax spores, and their ease of production in vitro, makes them extraordinarily well suited to use (in powdered and aerosol form) as biological weapons.

While previous examples demonstrate the effectiveness of the periodate method, compared to the standard method, for releasing nucleic acid from spores, it is important to also understand whether any viable spores remain following treatment with periodate.

Experimental Method

*Bacillus anthracis*, *Clostridium botulinum*, and *Clostridium difficile* Spore Preparation Frozen stock cultures of *C. botulinum* Type B and *C. difficile* were cultured on Trypticase Soy Agar with 5% Sheep's Blood and incubated anaerobically at 35° C. for 24 to 48 hours. After initial incubation, these cultures were transferred to multiple (minimum of 10) Brain Heart Infusion Agar plates and incubated anaerobically at 35° C. for up to 2 weeks.

Frozen stock culture of *B. anthracis* Sterne Strain was cultured on Trypticase Soy Agar with 5% Sheep's Blood and incubated at 35° C. with 5% $CO_2$ for 24 hours. After initial incubation, this culture was transferred to multiple (minimum of 10) *Bacillus* Sporulation Agar plates and incubated aerobically at 35° C. with $CO_2$ for up to 2 weeks.

Malachite Green spore staining was performed every 3 to 4 days to monitor sporulation of bacteria in vitro. When the malachite green stains prepared showed almost complete sporulation of organisms, the spores were harvested into 5.0 mL of PBS (pH 7.4) and stored at room temperature until use.

Determination of Spore Concentration

Each spore stock suspension of *C. botulinum* and *C. difficile* were diluted in PBS to $10^{-2}$. *B. anthracis* Sterne Strain was diluted to 10-3 in PBS. An aliquot (10 µL) of each of these final dilutions were loaded into each clean well of a 2-chamber hemocytometer slide. Hemocytometer chambers were observed at 40× magnification without oil for spore counting. Spores were visualized as round or oval black cells on the light field grid of the hemocytometer.

*Bacillus anthracis*, Limit of Detection (LOD)=53 spores/reaction; *C. botulinum*, LOD=30 spores/reaction; *C. difficile*, LOD=20 spores/reaction.

Treatment of Spores Using Standard and Periodate Methods

1. Prepared 700 µL of spore stock suspension for each organism at the required concentration.
2. Split each sample into 2×350 µL volumes
3. 350 µL for WC BDL Standard Method ("Collaborator"):
    a. 50 µL aliquot was removed to confirm spores were viable by plating onto Trypticase Soy Agar with 5% Sheep's Blood (see below).
4. 350 µL for Periodate Method:
    a. 350 µL BD2 buffer (2% SDS, 12.5 mM CDTA, 250 mM LiCl, 50 mM glycine, pH 10.5) was added to the 350 µL spore stock suspension of *B. anthracis, C. botulinum* and *C. difficile*.
    b. Vortexed to mix.
    c. Removed 100 µL for culture ("Pre-Periodate").
    d. Added 50 µL of 300 mM sodium (meta)periodate or NPI stock (final concentration 30 mM), vortexed to mix.
    e. Incubated at 70° C. in a water bath for 20 minutes.
    f. Cooled samples at room temperature for 2 minutes.
    g. Removed 100 µL for culture ("Post-Periodate").

Culture of Spores to Determine Viability

*B. anthracis*: Aliquots were plated directly onto Trypticase Soy Agar with 5% Sheep's Blood and incubated at 35° C. with 5% $CO_2$ for 24 hours.

*C. botulinum* and *C. difficile*: Aliquots were plated directly onto Trypticase Soy Agar with 5% Sheep's Blood and incubated anaerobically at 35° C. for 24 to 48 hours.

Results and Discussion

Figures 15, 16:
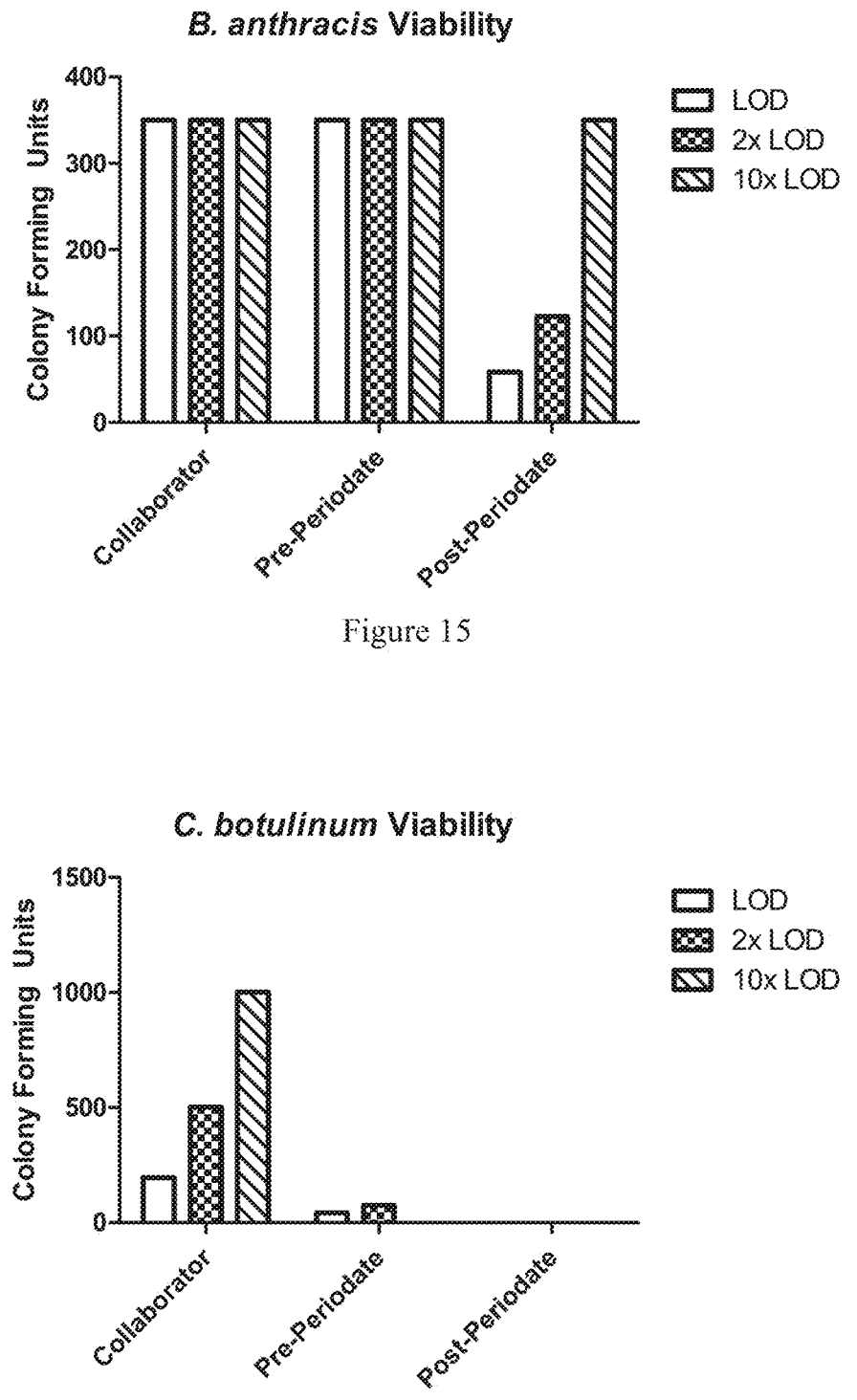
Figure 17:
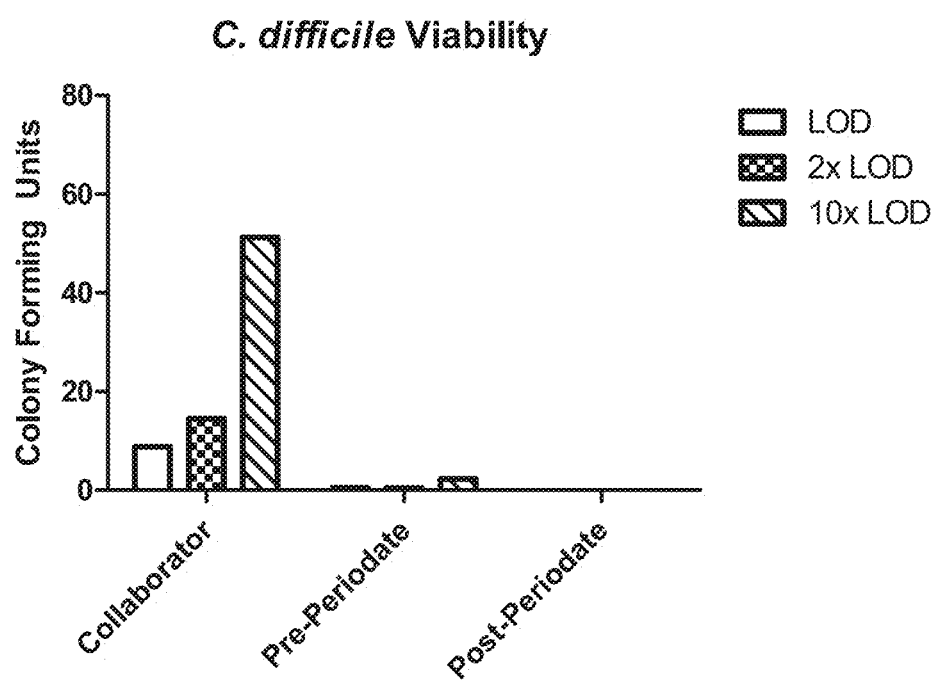
FIG. 17 graphically depicts *C. difficile* spore viability following standard decontamination and treatment with periodate.

This example demonstrates that the present "Periodate" method is very effective at reducing the viability of hardy spores from *B. anthracis* (FIG. 15), *C. botulinum* (FIG. 16), and *C. difficile* (FIG. 17). Periodate treatment (Post-Periodate) dramatically reduced the viability of *B. anthracis* spores, but did not eradicate all spores present with one treatment. In contrast, no *C. botulinum* or *C. difficile* spores were viable by culture following a periodate treatment. Interestingly, BD2 buffer alone (Pre-Periodate) had a significant impact on *C. botulinum* and *C. difficile*, but not *B. anthracis*, spore viability, suggesting these microorganisms are easier to lyse than *B. anthracis*.

Example 13: Use of the Present Invention to Detect Mycobacteria in Saliva and Oral Wash Specimens According to the World Health Organization, in 2012, 1.3 million people died from TB, 8.6 million people fell ill with TB, and an estimated 530,000 children <15 years of age became ill with this infectious disease worldwide. TB is an air-borne disease transmitted through fine respiratory droplets from an infected person. Persons with TB are most likely to spread it to people who have close and prolonged contact with them, such as family members, friends and coworkers.

Pediatric TB diagnosis is impeded by difficulty obtaining sputum samples in children and the paucibacillary nature of their disease that often necessitates invasive procedures such as gastric aspiration or bronchoscopy. If TB could be diagnosed from saliva or oral samples, collection could easily take place in the field or in clinics. However, with conventional DNA extraction methods, the abundance of MTB in saliva of TB-infected individuals is considered too low for saliva to be considered a reliable sample type for the diagnosis of active pulmonary TB.

Today, diagnostic laboratories rely largely on sputum specimens to make a diagnosis of pulmonary TB. However, many patients, including infants and children, are unable to expectorate sputum, making an alternate non-invasive sample for TB diagnostic investigations valuable. Several studies have assessed the use of oral wash specimens (Davis J L et al., 2009) and saliva samples (Yassen G et al., 2012) for the detection of active TB. In patients who cannot produce sputum, saliva samples and/or oral wash specimens may be easier and safer to obtain, compared with inducing sputum, which can be uncomfortable and dangerous for hypoxic patients and time-consuming and hazardous for staff. For the collection of oral wash specimens, subjects are instructed to cough vigorously 5 times, and then gargle 10 mL of sterile saline for 60 seconds. Fewer infectious aerosols are generated with oral wash specimens and saliva samples, compared to expectorated sputum.

It is well known that the sensitivity of PCR to diagnose disease can be improved by optimizing the DNA extraction technique. Example 9 (above) demonstrates that the periodate method of the present invention releases significantly more DNA from MTB in sputum than standard of care methods utilizing bead beating. In addition, Example 10 indicates that the periodate-based method releases significantly more MTB DNA in saliva than does Qiagen DNA extraction method. Hence, it is anticipated that the increased sensitivity in detection gained by utilizing the present invention to extract MTB DNA will, for the first time, enable the widespread use of saliva and/or oral wash specimens as preliminary diagnostic specimens for pulmonary TB in symptomatic individuals, especially children. While the numbers of MTB in saliva of actively infected individuals is low, it is anticipated the increased sensitivity of detection gained by the periodate-based method will enable a more reliable molecular detection of MTB using this easy to collect sample type. Saliva and/or oral wash specimens could be readily collected from symptomatic individuals to rapidly screen for TB and initiate treatment at an earlier stage which, in turn, will reduce the transmission and morbidity associated with this infectious disease.

Similarly, it is anticipated that the composition of the present invention can also be used with bronchoalveolar lavage samples, urine, feces and gastric aspirates to extract DNA from MTB, resulting in an increased sensitivity of detection of TB in molecular diagnostic tests, and increase in the number of TB cases identified.

Example 14: Use of Periodate for Releasing Nucleic Acids from a Broad Array of Microorganisms In this example, a panel of various microorganisms, including Gram-positive bacteria (*Bacillus thuringiensis, Staphylococcus aureus, Mycobacterium smegmatis*), Gram-negative bacteria (*Moraxella catarrhalis, Klebsiella pneumonia, Pseudomonas aeruginosa, Yersinia enterocolitica, Francisella philomiragia*) and yeast (*Candida albicans*), were treated with periodate. The release of nucleic acids from these microorganisms was assessed using 2 distinct methods, namely the Acid-Extraction HPLC Method and real-time PCR (qPCR).

Experimental Methods

Bacteria and yeast were grown in recommended growth media and at recommended temperature as follows: in YEPD broth (*C. albicans*), Tryptic soy broth with 0.1% cysteine (*F. philomiragia*), Brain heart infusion broth (*Y. enterocolitica, M. catarrhalis*) or Tryptic soy broth (*B. thuringiensis, S. aureus, M. smegmatis, K. pneumonia, P. aeruginosa*). *Y. enterocolitica* and *C. albicans* were grown at 30° C., while other microorganisms were grown at 35° C.

After overnight growth cells were collected by centrifugation at 7,500 g for 8 minutes; the supernatant was discarded. Bacterial pellets were washed once with cold phosphate-buffered saline by centrifuging at 7,500 g for 6 minutes and discarding the supernatants. The washed bacterial pellets were resuspended in 1.5 mL of cold water.

180 μL of cell suspension was mixed with 200 μL of BD2 buffer (2% SDS, 12.5 mM CDTA, 250 mM LiCl, 50 mM glycine, pH 10.5) and 20 μL of 300 mM periodate or RNase-/DNase-free water (control) was added to samples not receiving periodate. Samples were incubated for 20 minutes at 35° C., 70° C. or 80° C. Samples were centrifuged at 14,000 rpm for 5 minutes. The supernatants were transferred to a fresh tube and the pellets were discarded.

All samples were purified with the addition of 16 μL of TK buffer (500 mM Tris, 1.5 M potassium acetate, pH 5.5), incubated first for 5 minutes at room temperature, then for 15 minutes on ice, followed by centrifugation for 5 minutes at 14,000 rpm. Half the volume of each sample was precipitated with 2× volume of cold 95% ethanol for 1 hour at −20° C.; the other half was subjected to acid-hydrolysis by the addition of HCl to 0.2 N final concentration, and incubated at 60° C. for 60 minutes. NaOH was added to 0.1 N excess to all acid hydrolysed samples, followed by incubation at 100° C. for 10 minutes. To neutralize the samples for reverse-phase HPLC, 300 μL of 500 mM ADA pH 6.5 was added to samples and samples were centrifuged for 3 minutes at 14,000 rpm for 5 minutes. Supernatants were analysed by HPLC while any insoluble material was discarded.

Samples in ethanol were centrifuged for 3 minutes at 14,000 rpm, supernatants were removed, and pellets were dissolved in 50 μL of cold RNase-/DNase-free water. 1 μL of purified material was used as template in 25 μL PCR reactions in duplicate. See example 6 for conditions of real-time PCR using universal bacterial primers.

Universal fungal primers were F: 5'-gcatcgatgaagaacgcagc-3' and R: 5'-tcctccgcttattgatatgc-3'. Each 25 μL PCR reaction contained 2.0 mM MgCl$_2$, 0.2 mM dNTPs, 1.0 μM Syto 9, 4.0 pmole universal fungal primer F, 4.0 pmole universal fungal primer R, 2.0 μg bovine serum albumin (BSA), 1 U FastStart Taq DNA polymerase (Roche) and 1× FastStart PCR master mix. The cycling conditions for universal fungal primers were as follows: 95° C. for 2 minutes×1, (95° C. for 20 seconds, 56.5° C. for 30 seconds, 72° C. for 25 seconds)×38.

Results and Discussion

Clearly, significantly more DNA was released from a wide array of microorganisms in the presence of periodate than without it, as shown by both real-time PCR (Tables 19-21) and the Acid-Extraction HPLC Method (Tables 22-30). This effect of periodate appeared to be temperature dependent with optimal nucleic acid release occurring at 70-80° C. Periodate released nucleic acids from both Gram-positive and Gram-negative bacteria, as well as fungus. Interestingly, periodate released relatively small amounts of nucleic acid from *S. aureus* as detected by the HPLC method, but not real-time PCR.

TABLE 19

$C_t$ values from real-time PCR using universal bacterial primers.

| Microorganism | Periodate | 35° C. | 70° C. | 80° C. |
|---|---|---|---|---|
| *M. catarrhalis* | − | 16.7 | 17.2 | 12.7 |
| | + | 16.3 | 12.7 | 10.8 |
| *K. pneumonia* | − | 15.9 | 16.4 | 17.5 |
| | + | 24.3 | 9.3 | 9.6 |
| *P. aeruginosa* | − | 12.8 | 13.5 | 12.4 |
| | + | 10.8 | 7.8 | 8.8 |

TABLE 20

$C_t$ values from real-time PCR using universal bacterial primers or universal fungal primers.

| Microorganism | Periodate | 35° C. | 70° C. | 80° C. |
|---|---|---|---|---|
| *B. thuringiensis* | − | 14.2 | 12.9 | 13.1 |
| | + | 15.5 | 10.3 | 10.8 |
| *Y. enterocolitica* | − | 14.8 | 14.9 | 14.5 |
| | + | 15.5 | 12.0 | 11.4 |
| *C. albicans* | − | 23.4 | 19.1 | 17.4 |
| | + | 27.1 | 15.2 | 15.7 |

TABLE 21

$C_t$ values from real-time PCR using universal bacterial primers.

| Microorganism | Periodate | 35° C. | 70° C. | 80° C. |
|---|---|---|---|---|
| *S. aureus* | − | 13.9 | 13.9 | 14.1 |
| | + | 15.5 | 13.7 | 15.0 |
| *F. philomiragia* | − | 17.5 | 17.0 | 17.8 |
| | + | 15.3 | 15.5 | 16.0 |
| *M. smegmatis* | − | 22.3 | 22.4 | 22.3 |
| | + | 22.8 | 18.1 | 17.9 |

TABLE 22

% DNA Released from *F. philomiragia* as Determined by Acid Extraction HPLC Method.

| Temperature | Periodate (%) | Control (%) |
|---|---|---|
| 35° C. | 65.3 | 65.0 |
| 70° C. | 89.4 | 24.6 |
| 80° C. | 92.0 | 34.6 |

TABLE 23

% DNA Released from *S. aureus* as Determined by Acid Extraction HPLC Method.

| Temperature | Periodate (%) | Control (%) |
|---|---|---|
| 35° C. | 18.4 | 9.6 |
| 70° C. | 24.8 | 10.1 |
| 80° C. | 26.7 | 10.1 |

TABLE 24

% DNA Released from *M. smegmatis* as Determined by Acid Extraction HPLC Method.

| Temperature | Periodate (%) | Control (%) |
|---|---|---|
| 35° C. | 49.7 | 8.6 |
| 70° C. | 85.2 | 1.3 |
| 80° C. | 80.6 | 10.1 |

TABLE 25

% DNA Released from *B. thuringiensis* as Determined by Acid Extraction HPLC Method.

| Temperature | Periodate (%) | Control (%) |
|---|---|---|
| 35° C. | 42.1 | 26.5 |
| 70° C. | 103.5 | 27.5 |
| 80° C. | 107.7 | 28.8 |

TABLE 26

% DNA Released from *Y. enterocolitica* as Determined by Acid Extraction HPLC Method.

| Temperature | Periodate (%) | Control (%) |
|---|---|---|
| 35° C. | 52.1 | 24.2 |
| 70° C. | 80.8 | 36.6 |
| 80° C. | 89.5 | 34.2 |

TABLE 27

% DNA Released from *C. albicans* as Determined by Acid Extraction HPLC Method.

| Temperature | Periodate (%) | Control (%) |
|---|---|---|
| 35° C. | 105.4 | 53.7 |
| 70° C. | 155.3 | 51.4 |
| 80° C. | 156.4 | 53.6 |

TABLE 28

% DNA Released from *M. catarrhalis* as Determined by Acid Extraction HPLC Method.

| Temperature | Periodate (%) | Control (%) |
|---|---|---|
| 35° C. | 77.1 | 18.1 |
| 70° C. | 143.6 | 35.6 |
| 80° C. | 140.5 | 58.5 |

TABLE 29

% DNA Released from *K. pneumonia* as Determined by Acid Extraction HPLC Method.

| Temperature | Periodate (%) | Control (%) |
|---|---|---|
| 35° C. | 49.0 | 2.8 |
| 70° C. | 119.2 | 15.1 |
| 80° C. | 124.4 | 8.7 |

TABLE 30

% DNA Released from *P. aeruginosa* as Determined by Acid Extraction HPLC Method.

| Temperature | Periodate (%) | Control (%) |
|---|---|---|
| 35° C. | 38.6 | 19.4 |
| 70° C. | 117.8 | 69.8 |
| 80° C. | 98.2 | 31.0 |

Example 15: Use of Periodate for Releasing DNA from *M. tuberculosis* Present in Varied Biological Sample Types It is possible to find microorganisms in a variety of natural environments, host organisms and biological samples. This example shows that the present chemical "Periodate Method" of DNA extraction is suitable for detecting hardy organisms, such as *M. tuberculosis* from biological samples of varying complexity. Specifically, *M. tuberculosis* DNA was recovered from human urine and feces samples.

Experimental Methods

Preparation of *Mycobacterium tuberculosis*-spiked Biological Samples

To simulate tuberculosis-positive samples, 1 mL of urine or feces (from a preparation of ~400 mg feces collected into 2 mL of feces homogenization buffer (U.S. Ser. No. 61/949,692)) samples from healthy donors were spiked with attenuated *M. tuberculosis* (aMTB) to a final concentration of approximately $3 \times 10^6$ cfu/mL.

Extraction of DNA from *M. Tuberculosis* Positive Urine and Feces Using the "Periodate Method"

1. Mixed 200 µL of aMTB-spiked urine or feces with an equal volume of BD2 buffer
2. Add 40 µL NPI (final concentration 30 mM), vortex to mix, and incubate at 70° C. for 20 minutes
3. Cool samples at room temperature for 2 minutes
4. Add 1 M Tris buffer (pH7) to a final concentration of 50 mM
5. Incubate at room temperature for 10 minutes
6. Add 3 M potassium acetate (pH 5.5) to a final concentration of 150 mM
7. Incubate on ice for 10 minutes
8. Centrifuge at 15,000×g for 5 minutes
9. Transfer the supernatant to a fresh tube, and discard the pellet
10. Add 800 µL room temperature 95% ethanol and invert 20 times to mix
11. Incubate the samples at room temperature for 15 minutes to precipitate DNA
12. Centrifuge at 15,000×g for 2 minutes to pellet the DNA 13. Carefully remove and discard the supernatant, taking care not to disturb the pellet.
14. Add 100 µL TE to rehydrate the pellet Real-Time PCR DNA isolated from urine or feces spiked with aMTB was used in the RD4 Taqman Real-time PCR assay as described in Examples 9 and 10. The DNA was diluted 1:100 for feces prior to the assay, and 5 µL was used in each case.

Results and Conclusions

In this example, DNA extracted using the "Periodate Method" is detected as TB-positive in 100% of cases tested (Table 31), demonstrating that the current invention is effective in releasing functional DNA from samples ranging from low complexity (mainly aqueous, homogeneous, pH neutral solutions) to higher complexity (semi-solid, heterogeneous, pH variable composites).

TABLE 31

Percentage of Urine and Feces samples detected TB-positive following DNA extraction using the "Periodate Method".

| Sample Type | % Detected | Average Ct Value |
|---|---|---|
| Urine (n = 3) | 100 | 17.46 |
| Feces (1:100 dilution, n = 6) | 100 | 23.34 |

Example 16: Use of Periodate for the Biosafety of Infectious Samples

The continued rise of worldwide TB infections requires a robust medical response involving detection, treatment and prevention. Such a framework depends on a large network of laboratories and associated scientific personnel actively involved in the handling of highly infectious samples. Given the ease with which TB is transmitted, sophisticated, high-level biological safety cabinets (BSCs) are required for handling. Further, these workers are at a potentially higher risk of infection. A composition with the ability to rapidly render these samples "biosafe", i.e. no longer viable, and therefore safe for removal to a more basic laboratory for downstream analysis is a clear advantage in this field.

In this example, bacterial sediments obtained following the treatment protocols with and without periodate were evaluated from a biosafety perspective to ensure that the material can be safely removed from a BSL-3 (Biological Safety Level 3) for analysis in a molecular suite of a BSL-2 laboratory.

Experimental Methods

Preparation of *Mycobacterium tuberculosis*-Spiked Biological Samples

To simulate tuberculosis-positive sputum, saliva samples from healthy donors were spiked with attenuated *M. tuberculosis* (aMTB) with the following approximate stock concentrations:
 1. $7.5 \times 10^9$ cfu/mL (high load)
 2. $7.5 \times 10^7$ cfu/mL (medium load)

Spiked saliva samples were prepared according to the following groups, and each group was prepared using either the high load stock concentration or the medium load stock concentration:

A. 1.0 mL Saliva+1.0 mL BD2 buffer+100 µL aMTB stock: No NPI treatment
B. 2.0 mL Saliva+100 µL aMTB stock: No NPI treatment
C. 2.0 mL Saliva+100 µL aMTB stock: NPI treatment
D. 1.0 mL Saliva+1.0 mL BD2 buffer+100 µL aMTB stock: NPI treatment The final concentration of aMTB in each group was ~$3.75 \times 10^8$ cfu/mL (high load samples) or ~$3.75 \times 10^6$ cfu/mL (medium load samples). Each tube was vortexed briefly to mix, and the samples were processed as follows:

Protocol for Group A and Group B Samples
1. Aliquot each sample into three fresh 1.5 mL centrifuge tubes at 500 µL per tube
2. Centrifuge the tubes for 20 minutes at 3500×g
3. Remove and discard the supernatant
4. Re-suspend the sediment in 50 µL of sterile PBS
5. Apply the PBS sediment mixture carefully to the top edge of a Lawenstein-Jansen culture media tube (LJ slant), and rock gently from side to side to distribute sample.
6. Incubate at 35° C. for 42 days and score growth Protocol for Group C and Group D Samples
1. Aliquot each sample into three fresh 1.5 mL centrifuge tubes at 500 µL per tube
2. Centrifuge the tubes for 20 minutes at 3500×g
3. Remove and discard the supernatant
4. Re-suspend the sediment in 500 µL of 50% BD2 buffer
5. Add 50 µL of NPI (final concentration 30 mM), vortex to mix and incubate at 70° C. for 20 minutes
6. Cool samples at room temperature for 2 minutes
7. Add 1M Tris buffer (pH7) to a final concentration of 50 mM
8. Centrifuge the tubes for 20 minutes at 3500×g
9. Remove and discard the supernatant
10. Wash the sediment in 500 µL sterile PBS
11. Centrifuge the tubes for 20 minutes at 3500×g
12. Remove and discard the supernatant
13. Re-suspend the sediment in 50 µL of sterile PBS
14. Apply the PBS sediment mixture carefully to the top edge of a Löwenstein-Jansen culture media tube (LJ slant), and rock gently from side to side to distribute sample.
15. Incubate at 35° C. for 42 days and score growth Results and Conclusions

TABLE 32

Summary of aMTB growth on LJ slants in the presence or absence of NPI

| Groups | | A | B | C | D |
|---|---|---|---|---|---|
| Sample Composition | BD2 | + | − | − | + |
| | aMTB | + | + | + | + |
| | NPI | − | − | + | + |
| Growth (up to 42 days) | High load | +++ | ++* | NEG | NEG |
| | Medium load | ++ | ++* | NEG | NEG |
| Time to Positive (d) | High load | 8 | 1* | >42 | >42 |
| | Medium load | 10 | 1* | >42 | >42 |

*The absence of an initial Lysis Buffer (BD2) to remove background flora resulted in rapid growth of these contaminating organisms Table 32 demonstrates the prevention of TB viability in the presence of NPI. In groups A and B, where NPI is not present, TB colonies began to appear after 8-10 days (group A), and contaminating background flora overwhelmed the LJ medium within one day (Group B). In contrast, in groups C and D, where NPI has been added, no growth of any microorganism was observed, even after 42 days incubation which is the current culture standard for determining TB negative status. This shows that NPI is necessary for the prevention of TB viability. This effect is also seen even in the absence of an initial lysis buffer for the removal of background flora (BD2; Group C), indicating that NPI alone is sufficient for the prevention of TB viability. This is a clear improvement on the current state of the art as it allows the individual handling TB positive samples to quickly and effectively render the samples biosafe. The risk to the individual is thus lowered, and these NPI treated samples can be removed from the restrictive BSL3 environment to a BSL2 laboratory for further analysis including DNA extraction and real-time PCR (see Example 9).

Example 17: Test Activity of ML Directly in NaOH-NALC Sputum Sample

NaOH/NALC is widely used to liquefy sputum. This example demonstrates that periodate remains active, i.e. releases nucleic acids from MTB, in sputum samples treated with NaOH/NALC.

Experimental Methods

Preparation of *Mycobacterium tuberculosis*-Spiked Sputum Samples

To simulate tuberculosis-positive sputum, a sputum sample (purchased from Tissue Solutions Ltd., Glasgow, Scotland) was spiked with approximately 9×106 CFU/mL attenuated *M. tuberculosis* H37Ra (aMTB) and split into two portions. One portion was treated with an equal volume of NaOH/NALC for 15 minutes at room temperature, while the second portion was mixed with an equal volume of BD2 buffer (50 mM glycine, 250 mM LiCl, 12.5 mM Li-CDTA, 2% SDS, pH 10.5). BD buffer-treated sputum was centrifuged at 5,000 rpm for 20 minutes and the pellet was resuspended in 1 mL PBS to which 1 mL BD2 buffer was added.

Extraction of DNA from aMTB-Positive Sputum in NaOH/NALC or BD Buffer Using the Optimal Periodate Method 1. Three 200 µL aliquots of NaOH/NALC-treated sputum or BD2 buffer-treated sputum (above) were treated with NPI to a final concentration of 30 mM, vortexed to mix.
2. Incubated at 70° C. in a water bath for 20 minutes.
3. Cooled aliquots at room temperature for 2 minutes.
4. Added 1 M Tris buffer (pH 7) to a final concentration of 50 mM.
5. Added 3M potassium acetate (pH 5.5) to a final concentration of 150 mM.
6. Incubated on ice for 10 minutes.
7. Centrifuged at 13,200 rpm for 5 minutes.
8. Transferred supernatant to a clean tube. Discarded pellet.
9. Added 400 µL room temperature 95% ethanol. Inverted 20 times to mix.
10. Incubated samples at room temperature for 15 minutes to precipitate DNA.
11. Centrifuged at 15,000 rpm for 2 minutes to pellet DNA.
12. Gently removed and discarded supernatant taking care not to disturb the pellet.
13. Dissolved pellet in 200 µL TE. Vortexed briefly to fully resuspend DNA.

Extraction of DNA from aMTB-Positive Sputum in NaOH/NALC Using the Shortened Periodate Method 1. Three 200 µL aliquots of NaOH/NALC-treated sputum (above) were treated with NPI to a final contraction of 30 mM, vortex to mix.
2. Incubated at 70° C. in a water bath for 20 minutes.
3. Cooled aliquots at room temperature for 2 minutes.
4. Added 1 M Tris buffer (pH 7) to a final concentration of 50 mM.
5. Incubated at room temperature for 10 minutes.
6. Added 2 volumes of room temperature 95% ethanol. Inverted 20 times to mix.
7. Incubated samples at room temperature for 15 minutes to precipitate DNA.
8. Centrifuged at 15,000 rpm for 2 minutes to pellet DNA.
9. Gently removed and discarded supernatant taking care not to disturb the pellet.
10. Dissolved pellet in 200 µL TE. Vortexed briefly to fully resuspend DNA.

rtPCR Conditions

In this example, DNA isolated from sputum spiked-aMTB samples (above) was subjected to an rtPCR assay specific for *Mycobacterium*, the RD4 Taqman Real-time PCR assay (see example 10).

Results and Conclusions

As outlined above, the extraction protocol for NaOH/NALC-treated sputum can be shortened by removing the potassium acetate and centrifugation steps required to precipitate SDS from BD2 buffer-treated samples. The present example uses a real-time PCR assay specific for *M. tuberculosis* to demonstrate that periodate is capable of releasing nucleic acid from aMTB in sputum after treatment with NaOH/NALC (Table 33). Compared to the method of the present invention, BD2 buffer treatment followed by DNA extraction using periodate, Ct values were only 2 cycles higher when sputum was treated with NaOH/NALC prior to DNA extraction using periodate.

TABLE 33

Quantification of DNA released from aMTB-spiked sputum.

| Sample Treatment | DNA Extraction Method | $C_t$ value Aliquot 1 | $C_t$ value Aliquot 2 | $C_t$ value Aliquot 3 | Average $C_t$ value |
|---|---|---|---|---|---|
| NaOH/NALC | Shortened Periodate Method | 27.13 | 26.90 | 26.34 | 26.79 |
| NaOH/NALC | Optimal Periodate Method | 27.12 | 27.94 | 26.79 | 27.28 |
| BD2 Buffer | Optimal Periodate Method | 23.60 | 25.53 | 24.98 | 24.70 |

Example 18: Periodate Method Compared to Standard of Care Method for Molecular Detection of *Mycobacterium Tuberculosis*

The CDC recommends that clinical specimens be analyzed simultaneously by culture, acid-fast *bacillus* (AFB) staining, and nucleic acid amplification protocols (Anonymous, 2009). Culture is the "gold standard" for final determination of TB positivity, but it is slow and may take up to 8 weeks. AFB staining is rapid, but has a low sensitivity and low specificity, since it does not distinguish non-tuberculosis Mycobacteria (NTM) from members of the *M. tuberculosis* complex (MTBC). Thus, rapid identification, which is essential to control spread of disease, relies on nucleic acid amplification protocols, such as real-time PCR (qPCR) and sequencing.

The assessment of antibiotic resistance in *M. tuberculosis*-infected patients is critically important to patient management and controlling the spread of disease. Standard methods for drug susceptibility testing (DST) of *M. tuberculosis* can take weeks to months to provide results. Due to the emergence of multidrug-resistant tuberculosis (MDR-TB) and extensively drug-resistant tuberculosis (XDR-TB), rapid molecular approaches have been developed. Mutations within rpoB gene are associated with rifampin (RIF) resistance, while mutations with katG and inhA genes are associated with Isoniazid resistance. Halse et al. (2010) developed a two-step molecular approach which utilized antibiotic resistance gene pyrosequencing analysis directly with clinical specimens positive for *Mycobacterium tuberculosis* complex (MTBC) by real-time PCR.

In this example, a side-by-side comparison of the clinical evaluation of TB-positive sputum samples (kindly donated by the Foundation for Innovative Diagnostics (FIND) Tuberculosis Specimen Bank) treated by two distinct methods, was performed. Specifically, 1) the "Standard of Care" method, consisting of sodium hydroxide treatment followed by bead beating, and 2) the present invention were compared in terms of sensitivity in a CLIA/CLEP-approved qPCR assay (targeting the RD4 MTBC region of difference (RD)) (Halse et al., 2011) and antibiotic resistance gene pyrosequencing assay (Halse et al., 2010). In the present method, TB-positive sputum samples were treated with BD2 buffer and periodate to facilitate chemical lysis of cells in the specimen, prior to isolation of DNA and assay testing.

In contrast to the present invention, the "Standard of Care" includes bead beating, a mechanical method, to break open bacteria in sputum samples. While mechanical bead beating can be effective at breaking open organisms, it does create dangerous aerosols in the laboratory environment. Hence, it is highly desirable to develop an effective, non-mechanical, chemical method to safely release DNA from *Mycobacterium tuberculosis*, without negatively impacting the clinical sensitivity of the diagnostic tests.

Experimental Method

*Mycobacterium tuberculosis*-Positive Sputum Samples

For the present example, raw sputum samples from confirmed TB-positive patients were kindly donated by the Foundation for Innovative Diagnostics (FIND) Tuberculosis Specimen Bank. Using smear and culture analysis, FIND categorized these samples as 'low', 'mid' and 'high' TB-positive specimens. Duplicate 0.5 mL aliquots were provided from 30 patient samples and stored frozen. Aliquots were shipped frozen to Wadsworth Center Mycobacteriology Laboratory (New York State Department of Health, Albany, N.Y., U.S.A.), a CLIA/CLEP-approved Clinical Laboratory for further analysis.

Duplicate aliquots from 30 donors were thawed on ice; one set of aliquots was processed using the "Standard of Care" Method (Collaborator) and the second set was treated with BD2 buffer and periodate (Periodate), prior to isolation of DNA.

Treatment of TB-Positive Sputum Using the "Standard of Care" Method

1. Added 0.5 mL 3.5% NaOH to each 0.5 mL sputum aliquot (n=6); vortexed to mix.
2. Incubated at room temperature for 15 minutes.
3. Brought up to 10 mL with sterile phosphate-buffered saline (PBS).
4. Centrifuged at 5,000 rpm for 20 minutes to pellet bacteria. Discarded the supernatant.
5. Resuspended the pellet in 0.5 mL sterile PBS.
6. Set aside 300 µL of resuspended bacteria for culture to confirm viability of *M. tuberculosis*.
7. Lysed bacteria by adding 200 mg of 105-150 micron glass beads to remaining 200 µL of resuspended bacteria.
8. Bead beat for 2 cycles of 1 minute, followed by 1 minute on ice using a Mini-BeadBeater (BioSpec Products).

Treatment of TB-Positive Sputum Using the Periodate Method

1. Added 0.5 mL BD2 buffer (2% SDS, 12.5 mM CDTA, 250 mM LiCl, 50 mM glycine, pH 10.5) to each 0.5 mL sputum aliquot (n=6); vortexed to mix.
2. Added Proteinase K (400 g) and incubated at 50° C. in a water bath for 2 hours.
3. Added NPI to a final concentration of 30 mM, vortexed to mix.
4. Incubated at 70° C. in a water bath for 20 minutes.
5. Cooled samples at room temperature for 2 minutes.
6. Added 1 M Tris buffer (pH 7) to a final concentration of 50 mM.
7. Incubated at room temperature for 10 minutes.
8. Added 3M potassium acetate (pH 5.5) to a final concentration of 150 mM.
9. Incubated on ice for 10 minutes.
10. Centrifuged at 13,000 rpm for 5 minutes.
11. Transferred supernatant to a clean, labeled tube. Discarded pellet.
12. Added 2 volumes of room temperature 95% ethanol; inverted 20 times to mix.
13. Incubated samples at room temperature for 15 minutes to precipitate DNA.
14. Centrifuged at 15,000 rpm for 2 minutes to pellet DNA.
15. Gently removed and discarded supernatant taking care not to disturb the pellet.
16. Dissolved pellet in 200 µL TE.
17. Vortexed briefly to fully resuspend DNA and let stand at room temperature for a minimum of 30 minutes.

Real-Time PCR for *M. tuberculosis* and Pyrosequencing for Antibiotic Resistance Duplicate reactions of 5 µL 'neat' DNA and 5 µL diluted (1:10) DNA from each purified sputum sample (above) were amplified on an ABI 7500 real-time PCR instrument using a CLIA/CLEP-approved qPCR assay targeting the RD4 MTBC region of difference (RD) (Halse et al., 2011). Threshold cycle ($C_t$) values less than 37 were reported as positive, and samples with values greater than 37 were retested; if the results were the same, the result was reported as positive, and if they were not, they were reported as inconclusive.

Antibiotic resistance profiling was done using the previously published pyrosequencing method for rifampcin resistance (rpoB) (Halse et al, 2010) and additional targets for isonazid resistance (inhA and katG). DNA obtained from both methods was used in separate PCR reactions to amplify specific regions of the rpoB, inhA and katG genes. Mutations in these regions indicate probable resistance to either rifampcin and/or isonazid antibiotics.

Results and Discussion

Today, the standard of care method involves liquefaction of sputum with sodium hydroxide (or NaOH/NALC), followed by isolation of DNA from bacteria using mechanical bead beating. The present method is different in that a simple chemical treatment, including periodate, efficiently lyses bacteria. Importantly, the present composition and method appeared to be just as effective, if not more effective, compared to the standard of care methodology, in leading to the subsequent detection of *M. tuberculosis*-specific DNA and antibiotic resistance markers.

pyrosequencing data. The samples treated with periodate had DNA available in sufficient quantities to be tested for antibiotic resistance markers on day 0 of testing. In contrast, the standard of care method required an average of 14 days for MGIT cultures to become positive before pyrosequencing could be repeated on samples that were negative by PCR at day 0. The antibiotic profile of a patient is critical for case management and earlier intervention with the appropriate

TABLE 34

Pyrosequencing Results for Three Antibiotic Resistance Markers in *M. tuberculosis*.

| Study ID # | Method | Real-time PCR $C_t$ value (in duplicate) | rpoB gene | katG gene | inhA gene | MGIT Growth |
|---|---|---|---|---|---|---|
| FIND 01 01 2072 LOW | Collaborator | Negative (straight, 1:10) | Failed | Failed | Failed | NG |
|  | Periodate | 32/32 | WT | Failed | C(−15)T |  |
| FIND 01 01 2137 LOW | Collaborator | 34/34 (1:10) | Failed | Failed | WT | NG |
|  | Periodate | 41/33 | Asp516Val | Failed | WT |  |
| FIND 01 01 2166 MID | Collaborator | 26/26 (1:10) | Failed/WT(M) | WT | WT | Yes (12 d) |
|  | Periodate | 23/23 | WT | WT | WT |  |
| FIND 01 01 2287 MID | Collaborator | 34/34 (1:10) | Failed | Failed | G(−17)T | NG |
|  | Periodate | 33/33 | WT | WF | G(−17)T |  |
| FIND 10 01 0041 HIGH | Collaborator | 27/27 (1:10) | Failed/WT(M) | Failed/WT(M) | C(−15)T | Yes (10 d) |
|  | Periodate | 19/19 | WT | WT | C(−15)T |  |
| FIND 10 01 0042 HIGH | Collaborator | 31/31 (1:10) | Failed/WT(M) | Failed/WT(M) | Failed/WT(M) | Yes (19 d) |
|  | Periodate | 24/25 | WT | WT | WT |  |

WT, Wild type;
NG, no growth;
STC, sputum transport chemistry
M, Pyrosequencing was done using a HK made from the MGIT growth Compared to the conventional method ("Collaborator", Table 34), the present chemical method ("Periodate", Table 34) led to increased clinical sensitivity of *M. tuberculosis*-specific detection by qPCR in duplicate sputum samples categorized previously as 'low' and 'mid' TB-positive by culture and smear microscopy. In this example, not until DNA extracted using the "Standard of Care" method was diluted 10-fold was *M. tuberculosis* detected by qPCR in 'mid' and 'high' TB-positive sputum samples (Table 34). For all TB burden levels, Table 1 illustrates the significantly improved limit of detection (lower $C_t$ values by qPCR) of *M. tuberculosis* in all TB-positive sputum samples treated using the present method (Periodate), compared to the standard of care method (Collaborator). This lower limit of detection helps ensure an accurate diagnosis of *M. tuberculosis* from patient sputum samples.

Similarly, the present composition and method is compatible with industry standard testing to predict antibiotic resistance in *M. tuberculosis*-positive specimens. Pyrosequencing assay results obtained with the standard of care method and periodate method were 100% concordant for the 6 clinical TB-positive sputum specimens tested. Importantly, from these 6 patient sputum specimens, the present periodate method, but not the standard of care method, detected 2 patients (FIND 0101 2072 and FIND 01 01 2137) with antibiotic resistance markers (inhA and ropB genes) (Table 34). Even the gold standard culture test failed to show growth of Mycobacteria in these 2 patients' samples after 52 days in vitro.

The impact of the increased recovery of Mycobacteria DNA at the time of testing is best highlighted with the antibiotic therapy will decrease transmission rates and increase the chances of recovery. Hence, the present invention is valuable for rapid, same-day identification of MTBC by real-time PCR and sensitive enough to detect antibiotic resistance markers for *M. tuberculosis*, without waiting for the detection of Mycobacteria by culture.

Example 19: Detection of MTB from Sputum Swab Samples

For optimal control of tuberculosis, early diagnosis is essential. Several researchers have developed real-time PCR assays that provide rapid detection of various target sequences of *Mycobacterium tuberculosis* complex (MTBC) and drug resistance genes in patient samples. The ability of these assays to detect MTBC in clinical samples is dependent on both the target sequence selected and the efficiency of the DNA extraction procedure. Previous examples have demonstrated that the present invention substantially improves nucleic acid extraction from microorganisms, such as MTB, increasing the sensitivity of *M. tuberculosis* detection in human sputum.

Instead of processing entire sputum specimens, further efficiencies can be gained by extracting nucleic acids directly from a small fraction of each specimen in its raw or untreated state, i.e., prior to decontamination with sodium hydroxide and/or NALC. This example demonstrates that commercially available swabs can be used to successfully capture and transfer small aliquots (approximately 100-200 microliters per swab) of untreated sputum. Combined with the extraction efficiency gained with the present invention, processing of a small fraction of the entire specimen can greatly improve specimen handling in the lab, as well as time to diagnosis.

Materials and Methods

One 3 mL frozen, untreated sputum sample (Tissue Solutions Ltd.) was thawed and spiked with $9 \times 10^7$ CFU/mL attenuated MTB H37Ra (aMTB). One at a time, 8 FLOQ (Copan Diagnostics Inc.; Cat. No. 502CS01) and 8 Hydra Flock (Puritan Medical Products Co., LLC; Cat. No. 25-3406-H) swabs were dipped into aMTB-spiked sputum, swirled for 10 seconds, and then transferred into tubes containing 500 μL of BD2 buffer (50 mM glycine, 250 mM LiCl, 12.5 mM Li-CDTA, 2% SDS, pH 10.5). Following 2 hours at room temperature, the swabs were removed, the tubes were centrifuged at 3,500 g for 20 minutes, and the pellets were resuspended in 100 μL PBS. Two resuspended samples per swab were plated onto M7H10 agar plates and incubated at 35° C. for 21 days to confirm viability of aMTB; six resuspended samples per swab were mixed with 100 μL BD2 buffer prior to nucleic acid extraction with and without periodate (see below).

Extraction of DNA from aMTB-Positive Sputum Using the Periodate Method

1. Five 200 μL aliquots (swabs 1-5; above) were treated with NPI to a final concentration of 30 mM, vortexed to mix; one 200 μL aliquot (swab 6) was not treated with NPI.
2. Incubated at 70° C. in a water bath for 20 minutes.
3. Cooled aliquots at room temperature for 2 minutes.
4. Added 1 M Tris buffer (pH 7) to a final concentration of 50 mM.
5. Added 3M potassium acetate (pH 5.5) to a final concentration of 150 mM.
6. Incubated on ice for 10 minutes.
7. Centrifuged at 13,200 rpm for 5 minutes.
8. Transferred supernatant to a clean tube. Discarded pellet.
9. Added 400 μL room temperature 95% ethanol. Inverted 20 times to mix.
10. Incubated samples at room temperature for 15 minutes to precipitate DNA.
11. Centrifuged at 15,000 rpm for 2 minutes to pellet DNA.
12. Gently removed and discarded supernatant taking care not to disturb the pellet.
13. Dissolved pellet in 200 μL TE. Vortexed briefly to fully resuspend DNA.

rtPCR Conditions

In this example, DNA isolated from aMTB-spiked sputum samples (above) was subjected to an rtPCR assay specific for *Mycobacterium*, the RD4 Taqman Real-time PCR assay (see example 10).

Results and Conclusions aMTB-spiked sputum collected with swabs was viable in culture. After 21 days in culture, aMTB isolated from Copan swabs produced a lawn of bacteria, while aMTB recovered from Puritan swabs produced approximately 200 colonies per plate.

The amount of aMTB DNA collected with a single Copan or Puritan swab was readily detected using MTB-specific rtPCR (swab 6; see Table 35). When periodate was included in the DNA extraction protocol (swabs 1-5; Table 35), the Ct values decreased by more than 3 cycles from 27.75 to 24.02 for Copan swabs and 27.62 to 23.69 for Puritan swabs, corresponding to more than a 10-fold increase in the amount of aMTB-specific DNA recovered per swab. In addition, rtPCR using neat versus diluted DNA (1:10) demonstrated the expected 3 cycle difference, indicating that the extracted DNA contained little to no inhibitors of PCR.

Hence, dipping a swab into an untreated sputum specimen may provide sufficient sample (100-200 μL) to rapidly diagnose the presence of *M. tuberculosis* in mid- to high-positive specimens. Importantly, the inclusion of periodate in the DNA extraction protocol increased the sensitivity of this detection by at least 10-fold which has important ramifications for low- to mid-positive specimens.

TABLE 35

Real-time PCR analysis of DNA isolated from sputum using swabs and periodate.

| | | $C_t$ value (neat DNA) | | $C_t$ value (1:10 dilution of DNA) | |
|---|---|---|---|---|---|
| | | Copan | Puritan | Copan | Puritan |
| (+) periodate | Swab 1 | 30.09 | 23.93 | 33.99 | 27.29 |
| | Swab 2 | 22.93 | 24.36 | 26.47 | 27.67 |
| | Swab 3 | 22.99 | 22.67 | 26.49 | 26.24 |
| | Swab 4 | 24.60 | 24.19 | 28.11 | 27.74 |
| | Swab 5 | 25.55 | 23.28 | 29.12 | 26.60 |
| | Average: | 24.02 | 23.69 | 27.55 | 27.11 |
| (−) periodate | Swab 6 | 27.75 | 27.62 | 31.33 | 32.83 |
| Periodate efficiency ($Ct_{Swab\ 6}$ (−) $Ct_{average}$) | | 3.73 | 3.93 | 3.78 | 5.72 |

ADDITIONAL REFERENCES

"Report of an Expert Consultation on the Uses of Nucleic Acid Amplification Tests for the bDiagnosis of Tuberculosis," Centers for Disease Control and Prevention.

"Molecular genetic methods for diagnosis and antibiotic resistance detection of mycobacterial from clinical specimens," I. C. Shamputa, L. Rigouts, F. Portaels, APMIS (2004) 112: 728-752.

"Measurement of sputum *Mycobacterium tuberculosis* messenger RNA as a surrogate for response to chemotherapy" L. E. Desjardin, M. D. Perkins, K. Wolski, S. Haun, L. Teixeira, Y. Chen, J. L. Johnson, J. J. Ellner, R. Dietze, J. Bates, M. D. Cave, K. D. Eisenach (1999) Am J Respir Crit Care Med 160: 203-210.

N. N. Greenwood and A. Earnshaw, *Chemistry of the Elements*, $2^{nd}$ Edition, Butterworth Heinemann, Oxford, Chapter 17, pp. 872-875 (1998).

A. Afkhami, T. Madrakian, A. R. Zarei, "Spectrophotometric determination of periodate, iodate and bromate mixtures based on their reaction with iodide, Analytical Sciences (2001) 17: 1199-1202.

Wroblewski D, Hannett G E, Bopp D J, Dumyati G K, Halse T A, Dumas N B, Musser K S (2009) Rapid molecular characterization of *Clostridium* dfficile and assessment of populations of *C. difficile* in stool specimens. J Clin Microbiol 47(7): 242-2148.

Halse T A, Escuyer V E, Musser K A (2011) Evaluation of a Single-Tube Multiplex Real-time PCR for the Differentiation of Members of the *Mycobacterium tuberculosis* Complex in Clinical Specimens. J Clin Microbiol 49(7): 2562-5267.

Halse T A, Edwards J, Cunningham P L, Wolfgang W J, Dumas N B, Escuyer V E, Musser K A (2010) Combined real-time PCR and rpoB gene pyrosequencing for rapid identification of *Mycobacterium tuberculosis* and determination of rifampin resistance directly in clinical specimens. *J Clin Microbiol* 48:1182-1188.

Corbett E L, Watt C J, Walker N, Maher D, Williams B G, Raviglione M C, Dye C (2003) The growing burden of tuberculosis: global trends and interactions with the HIV epidemic. Arch Intern Med 163:1009-1021.

Diagnostic Standards and Classification of Tuberculosis in Adults and Children; American Thoracic Society and the Centers for Disease Control and Prevention (2000) Am J Respir Crit Care Med 161:1376-1395.

Hobby G L, Holman A P, Iseman M D, Jones J (1973) Enumeration of tubercle bacilli in sputum of patients with pulmonary tuberculosis. Antimicrob Agents Chemother 4:94-104.

Yeager H J Jr, Lacy J, Smith L, LeMaistre C (1967) Quantitative studies of mycobacterial populations in sputum and saliva. Am Rev Respir Dis 95:998-1004.

Ghandi N R, Moll A, Pawinski R, et al. (August 2006) High prevalence and mortality from extensively-drug resistant (XDR) TB in TB/HIV coinfected patients in rural South Africa. Toronto, Canada: Late Breaker Session, XVI International AIDS Conference, 13-18 [Abstract THLB0210].

Raviglione M (2006) XDR-TB: entering the post-antibiotic era? Int J Tuberc Lung Dis 10(11):1185-1187.

Davis J L, Huang L, Kovacs J A, Masur H, Murray P, Havlir D V, Worodria W O, Charlebois E D, Srikantiah P, Cattamanchi A, Huber C, Shea Y R, Chow Y, Fischer SH (2009) Polymerase chain reaction of secA1 on sputum or oral wash samples for the diagnosis of pulmonary tuberculosis. Clinical Infectious Diseases 48: 725-732.

Yassen G, Noori J, Yas N S (2012) Detection of acid fast bacilli in the saliva of patients having pulmonary tuberculosis. J Bagh College Dentistry 24(3): 59-62.

Anonymous (2009) Updated guidelines for the use of nucleic acid amplification tests in the diagnosis of tuberculosis. MMWR Morb Mortal Wkly Rep 58: 7-10.

Halse T A, Edwards J, Cunningham P L, Wolfgang W J, Dumas N B, Escuyer V E, Musser K A (2010) Combined real-time PCR and rpoB gene pyrosequencing for rapid identification of *Mycobacterium tuberculosis* and determination of rifampin resistance directly in clinical specimens. *J Clin Microbiol* 48(4): 1182-1188.

Halse T A, Escuyer V E, Musser K A (2011) Evaluation of a single-tube multiplex real-time PCR for differentiation of members of the *Mycobacterium tuberculosis* complex in clinical specimens. *J Clin Microbiol* 49(7): 2562-2567.

Scott II R D (2009) The Direct Medical Costs of Healthcare-associated Infections in U.S. Hospitals and the Benefits of Prevention. Centers for Disease Control and Prevention.

Fawley W N, Wilcox M H (2001) Molecular epidemiology of endemic *Clostridium difficile* infection. Epidemiology and Infection 126(3):343-350. ISSN 0950-2688.

Martinez, J. A., Ruthazer, R., Hansjosten, K., Barefoot, L., and Snydman, D. R. (2003 September). "Role of environmental contamination as a risk factor for acquisition of vancomycin-resistant enterococci in patients treated in a medical intensive care unit." *Archives of Internal Medicine Vol.* 163(16):1905-12.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A composition comprising an oxidizing agent, a buffer, a lithium salt, a chelator and a denaturing agent, wherein the oxidizing agent is periodic acid or periodate, wherein the oxidizing agent is present in an amount of from about 5 mM to about 300 mM, and wherein the composition is an aqueous solution having a pH of at least 8.9.

2. The composition of claim 1, wherein the lithium salt is LiCl.

3. The composition of claim 1, wherein the denaturing agent is an anionic detergent, a cationic detergent, or a nonionic detergent.

4. The composition of claim 3, wherein the anionic detergent is sodium dodecyl sulfate (SDS), lithium dodecyl sulphate (LDS) or sodium lauroyl sulfate (SLS); wherein the cationic detergent is cetyltrimethylammonium bromide, cetylpyridinium bromide or alkylbenzyldimethylammonium chloride; and wherein the nonionic detergent is Tween, Triton X, or Brij.

5. The composition of claim 1, wherein the chelator is ethylene glycol tetraacetic acid (EGTA), (2-Hydroxyethyl) ethylenediaminetriacetic acid (HEDTA), diethylene triamine pentaacetic acid (DTPA), NitriloTriAcetic Acid (NTA), ethylenediaminetriacetic acid (EDTA), cyclohexanediaminetetraacetic acid (CDTA), N,N-bis(carboxymethyl)glycine, citrate anhydrous, sodium citrate, calcium citrate, ammonium citrate, ammonium bicitrate, citric acid, diammonium citrate, ferric ammonium citrate, lithium citrate, or any combination thereof.

6. The composition of claim 1, further comprising nucleic acid extracted from a microorganism or mixture of microorganisms, said nucleic acid being stabilized by the composition.

7. The composition of claim 1, wherein the composition has a pH of from about 9.5 to about 10.5.

8. The composition of claim 1, wherein the periodate comprises metaperiodate, orthoperiodate or a mixture thereof.

9. The composition of claim 1, wherein the periodate is sodium periodate, potassium periodate or lithium periodate.

10. The composition of claim 1, wherein the buffer comprises glycine.

11. A method for extracting nucleic acid from a microorganism comprising mixing a sample suspected of containing the microorganism with a composition comprising an oxidizing agent, a buffer, a lithium salt, a chelator and a denaturing agent, wherein the oxidizing agent is periodic acid or periodate, wherein the oxidizing agent is present in an amount of from about 5 mM to about 300 mM, and wherein the composition is an aqueous solution having a pH of at least 8.9, and heating the resulting mixture.

12. The method of claim 11, wherein the composition has a pH of from about 9.5 to about 10.5.

13. The method of claim 11 wherein the mixture is heated to a temperature of about 50° C. or greater, or from about 50° C. to about 100° C., or from about 70° C. to about 80° C.

14. The method of claim 11, wherein the mixture is heated for at least 10 minutes, at least 15 minutes, at least 20 minutes, from about 15 minutes to about 60 minutes, or from about 15 minutes to about 20 minutes.

15. The method of claim 11, wherein the periodate comprises metaperiodate, orthoperiodate or a mixture thereof.

16. The method of claim 11, wherein the periodate is sodium periodate, potassium periodate or lithium periodate.

17. The method of claim 11, wherein the concentration of periodate in the final mixture is from about 5 mM to about 30 mM, or about 15 mM.

18. The method of claim 11, wherein the lithium salt is LiCl.

19. The method of claim 11, wherein the denaturing agent is an anionic detergent, a cationic detergent, or a nonionic detergent.

20. The method of claim 19, wherein the anionic detergent is sodium dodecyl sulfate (SDS), lithium dodecyl sulphate (LDS) or sodium lauroyl sulfate (SLS); wherein the cationic detergent is cetyltrimethylammonium bromide, cetylpyridinium bromide or alkylbenzyldimethylammonium chloride; and wherein the nonionic detergent is Tween, Triton X, or Brij.

21. The method of claim 11, wherein the microorganism is a bacteria or fungus.

22. The method of claim 21 wherein the bacteria is *Mycobacterium tuberculosis*, species of the *Mycobacterium tuberculosis* complex, *Mycobacterium smegmatis*, *Mycobacterium bovis*, *Mycobacterium africanum*, *Mycobacterium microti*, *Mycobacterium canetti*, *Mycobacterium caprae*, *Mycobacterium pinnipedi*, *Mycobacterium marinum*, *Mycobacterium leprae*, *Mycobacterium lepromatosis*, *Mycobacterium avium*, *Mycobacterium avium-intra-cellulare*, *Mycobacterium avium paratuberculosis*, *Mycobacterium ulcerans*, *Mycobacterium gordonae*, *Bacillus* species, *Bacillus subtilis*, *Helicobacter pylori*, *Chlamydia pneumoniae*, *Chlamydia trachomatis*, *Toxoplasma gondii*, *Streptococcus* species, *Staphylococcus* species, *Dientamoeba fragilis*, *Borrelia burgdorferi* and other species, *Clostridia* species, *Fusobacterium nucleatum*, *Salmonella* species, *Campylobacter* species, *Firmicutes* bacteria, *Bartonella* species, *Rickettsia* species, *Yersinia* species, *Francisella* species, *Brucella* species, *Bordetella* species, *Burkholderia* species, *Pseudomonas* species, *Shigella* species, *Chlamydophila* species, *Legionella* species, *Listeria* species, *Corynebacterium* species, *Enterococcus* species, *Escherichia* species, *Haemophilus* species, *Helicobacter* species, *Leptospira* species, *Mycoplasma* species, *Neisseria* species, *Treponema* species, or *Vibrio* species.

23. The method of claim 21, wherein the fungus is the genus *Saccharomyces, Candida, Aspergillus, Histoplasma, Pneumocystis, Stachybotrys* or *Cryptococcus*.

24. A kit for nucleic acid extraction, wherein the kit comprises (i) an extraction composition comprising an oxidizing agent, a buffer, a lithium salt, a chelator and a denaturing agent, wherein the oxidizing agent is periodic acid or periodate, wherein the oxidizing agent is present in an amount of from about 5 mM to about 300 mM, and wherein the composition is an aqueous solution having a pH of at least 8.9; and (ii) instructions for use.

25. The kit according to claim 24, wherein the kit further comprises a reagent container and/or a sample receiving container.

26. The kit according to claim 25, wherein the reagent container and/or sample receiving container includes a reservoir for receiving the extraction composition and a sample receiving portion.

27. The composition of claim 1, wherein the oxidizing agent is present in an amount of from about 5 mM to about 30 mM, the lithium salt is present in an amount of about 250 mM, the chelator is present in an amount of from about 5 mM to about 50 mM, and the denaturing agent is present in an amount of from about 2.0% to about 4.0%.

28. The composition of claim 1, wherein the oxidizing agent is present in an amount of from about 5 mM to about 30 mM, the lithium salt is present in an amount of about 250 mM, the chelator is present in an amount of from about 5 mM to about 50 mM, and the denaturing agent is present in an amount of from about 2.0% to about 4.0%;
wherein the lithium salt is lithium chloride, and the composition has a pH of from about 9.5 to about 10.5.

* * * * *